(12) United States Patent
Alpegiani et al.

(10) Patent No.: US 6,194,451 B1
(45) Date of Patent: Feb. 27, 2001

(54) MATRIX METALLOPROTEINASE INHIBITORS

(75) Inventors: Marco Alpegiani, Milan; Massimiliano Palladino, Legnano; Riccardo Corigli, Milan; Daniela Jabes, Milan; Ettore Perrone, Milan; Maria Francesca Abrate, Milan; Pierluigi Bissolino, Pavia; Marina Lombroso, Milan, all of (IT)

(73) Assignee: Pharmacia & Upjohn S.p.A., Milan (IT)

( * ) Notice: Subject to any disclaimer, the term of this patent is extended or adjusted under 35 U.S.C. 154(b) by 0 days.

(21) Appl. No.: 09/355,315

(22) PCT Filed: Jan. 23, 1998

(86) PCT No.: PCT/EP98/00531

§ 371 Date: Jul. 3, 1999

§ 102(e) Date: Jul. 30, 1999

(87) PCT Pub. No.: WO98/33788

PCT Pub. Date: Aug. 6, 1998

(30) Foreign Application Priority Data

Jan. 31, 1997 (GB) .................................................. 9702088

(51) Int. Cl.$^7$ .......................... A61K 31/35; C07D 315/00
(52) U.S. Cl. ............................................ 514/459; 549/419
(58) Field of Search .............................. 549/419; 514/459

(56) References Cited

U.S. PATENT DOCUMENTS

| | | |
|---|---|---|
| 5,594,006 | 1/1997 | Sakamoto et al. . |
| 5,712,300 | 1/1998 | Jacobsen . |
| 5,804,593 | 9/1998 | Warpehoski et al. . |
| 5,830,869 | 11/1998 | Mitchell et al. . |
| 5,847,148 | 12/1998 | Jacobsen et al. . |
| 5,847,153 | 12/1998 | Warpehoski et al. . |
| 5,859,061 | 1/1999 | Jacobsen et al. . |

FOREIGN PATENT DOCUMENTS

| | | |
|---|---|---|
| WO 95 19956 | 7/1995 | (WO) . |
| WO 95 29892 | 11/1995 | (WO) . |
| WO 96 331166 | 10/1996 | (WO) . |

*Primary Examiner*—Deborah C. Lambkin
(74) *Attorney, Agent, or Firm*—Oblon, Spivak, McClelland, Maier & Neustadt, P.C.

(57) ABSTRACT

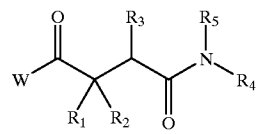

(I)

A compound of formula (I), wherein W is —NHOH or —OH, $R_1$ is either free or protected hydroxymethyl or mercaptomethyl or derivatives thereof, $R_2$ is free or protected hydroxy, $R_3$ and $R_4$ is an organic group, $R_5$ is hydrogen or methyl, or $R_4$ and $R_5$, together with the nitrogen atom to which they are attached, constitute an azaheterocyclyl group, and the solvates, hydrates and pharmaceutically acceptable salts thereof, can inhibit matrix metalloproteinases and the release of tumour necrosis factor (TNF). Processes for producing the compound, intermediates involved in the processes, and pharmaceutical compositions containing the compound are also described.

19 Claims, No Drawings

MATRIX METALLOPROTEINASE INHIBITORS

The present invention relates to new inhibitors of matrix metalloproteinases (hereinafter MMPs), to a process for their preparation, to pharmaceutical compositions containing them, and to the use of such compounds in the prevention, control and treatment of diseases in which the proteolytic action of MMPs is involved. Furthermore, since some of the compounds herein described potently inhibit the release of tumor necrosis factor-alpha (hereinafter TNF) from cells, another object of the present invention is the use of pharmaceutical compositions containing said compounds for the treatment or prophylaxis of inflammatory, immunological or infectious diseases promoted by the release of such cytokine.

Low molecular weight compounds able to inhibit one or more of the matrix metalloproteinases, in particular stromelysin-1 (MMP-3; EC 3.4.24.17), gelatinase A (MMP-2; EC 3.4.24.24), gelatinase B (MMP-9; EC 3.4.24.35), neutrophil collagenase (MMP-8; EC 3.4.24.34), interstitial collagenase (MMP-1; EC 3.4.24.7), matrilysin (MMP-7; EC 3.4.24.23), and collagenase-3 (MMP-13) are currently considered as promising therapeutic agents in degenerative, tumoral and autoimmune pathologies (e.g., P. D. Brown: "Matrix metalloproteinase inhibitors: A new class of anti-cancer agent", Curr. Opin. Invest. Drugs, 2:617–626, 1993; A. Krantz: "Proteinases in Inflammation", Annu. Rep. Med. Chem. 28:187–195, 1993). Many of such compounds described hitherto are peptide derivatives or pseudopeptides, bearing analogies to recognized peptide substrates of these enzymes, and characterized in addition by a functional group capable of binding the Zn (II) atom present in the catalytic site of said enzymes. Known classes of MMP inhibitors include those in which the Zn binding group is a hydroxamic acid, which is part of a (substituted) succinic moiety, in particular a succinic amide represented by the general formula (A)

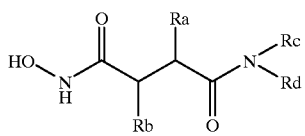

(A)

wherein $R_a$, $R_b$, $R_c$, and $R_d$ are hydrogen atoms or appropriate substituents (e.g., N. R. A. Beeley et al., "Inhibitors of matrix metalloproteinases (MMP's)", Curr. Opin. Ther. Patents 4:7–16, 1994; J. R. Porter et al., "Recent developments in matrix metalloproteinase inhibitors", Exp. Opin. Ther. Patents 5:1287–1296, 1995; J. R. Morphy et al., "Matrix metalloproteinase inhibitors: Current status", Curr. Med. Chem. 2:743–762, 1995; R. P. Beckett et al., "Recent advances in matrix metalloproteinase research", DDT 1:16–26, 1996).

Further, it is now recognized that some compounds of the same general formula (A) may be able to inhibit the release of TNF from the cell membrane anchored precursor, pro-TNF (e.g., G. M. McGeehan et al., "Regulation of tumour necrosis factor-alpha processing by a metalloproteinase inhibitor", Nature 370:558–561, 1994).

Although MMPs have been recognized as drug targets for at least 20 years, and MMP inhibitors encompassed by the general formula (A) have been disclosed since 1986 or before (e.g., see J. P. Dickens et al., U.S. Pat. No. 4,599,361), no drug of this type has arrived at the market yet. This is not because of questions about the therapeutic potential of MMP inhibitors, but because of problems of the "first generation" compounds, such as inhibitor potency, aqueous solubility, metabolic stability, and other desirable properties, oral bioavailability in particular (e.g., J. R. Porter, reference above; J. Hodgson, "Remodelling MMPIs", Biotechnology 13:554–557, 1995). For example, it is well known that most "first generation" hydroxamate MMP inhibitors are rapidly glucuronidated, oxidized to the carboxylic acid, and excreted in the bile (e.g., see J. Singh et al., Bioorg. Med. chem. Lett. 5:337–342, 1995, and reference above). Thus, there is a strong need for better and diversified molecules, especially as far as the properties referred to above are concerned. The present invention relates to a new class of carboxylic or hydroxamic acid derivatives, which are characterised by the presence of a 1,2-glycol, or a derivative thereof, next to the carbonyl group.

In particular, the present invention provides a compound of formula (I)

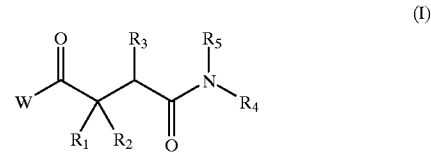

(I)

wherein

W is —NHOH or —OH;

$R_1$ is hydroxymethyl or a hydroxymethyl derivative which is an ether, an ester, a carbonate or a carbamate; or $R_1$ is mercaptomethyl or a mercaptomethyl derivative which is a sulfide (i.e., a thioether), a sulfoxide, a sulfone or a thioester;

$R_2$ is hydroxy or a protected derivate thereof; or $R_1$ and $R_2$, taken together with the carbon atom to which they are attached, represent an optionally substituted cyclopropane or oxirane, 1,3-dioxolane or 2-oxo-1,3-dioxolane ring of the following formulae (B1)–(B4):

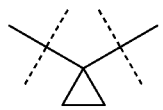

(B1)

(B2)

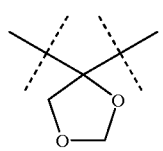

(B3)

(B4)

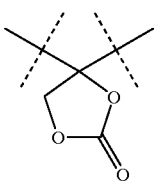

(D')

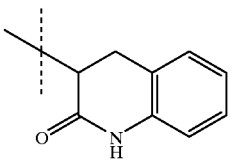

R₃ is a group —A'—X—(CH₂)ₙ—A, wherein A is $C_1$–$C_{10}$ alkyl, $C_2$–$C_{10}$ alkenyl, $C_3$–$C_7$ cycloalkyl, aryl, or heterocyclyl, the said alkyl, alkenyl, cycloalkyl, aryl and heterocyclyl groups being unsubstituted or substituted; n is either zero or an integer from 1 to 5; —X— is either a direct bond or a group —O—, —S—, —SO—, —SO₂—, —SO₂NH—, —CO—, —CONH—, —NHCO—, —OCONH—, NHCONH or —NHSO₂—, and —A'— is $C_1$–$C_{10}$ alkylene, $C_2$–$C_6$ alkenylene, or phenylene;

R₄ is either a group of formula (C):

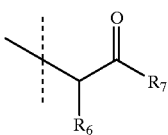

(C)

wherein R₆ is hydrogen or the side chain of a natural or non-natural alpha-amino acid, and R₇ is amino or a group —NH—A, —NH—CH₂—A or —NH—CH₂CH₂—A wherein A is as defined above; or R₄ is a group A as defined above or a group —A'—X—A wherein A, —X— and —A'— are as defined above; or R₄ is a group of formula (D):

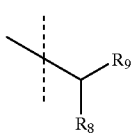

(D)

wherein R₈ is methyl, ethyl, phenyl, pyridyl, isopropyl, sec-butyl, tert-butyl, adamantyl, cylclopentyl, cyclohexyl, cyclohexylmethyl, phenylmethyl, 3,4-(methylenedioxy) phenyl, piperonyl, pyridylmethyl, thienylmethyl, 3-indolylmethyl, 3-(N-methyl)indolylmethyl, 1,1-diphenylmethyl, naphthyl, naphthylmethyl, quinolylmethyl, isoquinolylmethyl, thiazolyl, thiazolylmethyl, imidazolyl, imidazolylmethyl, or a derivative thereof optionally substituted, or R₈ is —C(CH₃)₂SCH₃ or a sulfoxide or sulfone thereof, —C(CH₃)₂OCH₃, —CH₂CH₂CH₂—OCH₃, or —CH(CH₃)OH or a tert-butyl ether thereof; R₉ is either hydrogen or a group selected from methyl, ethyl, phenyl, 3,4-(methylenedioxy)phenyl, piperonyl, pyridyl, benzimidazolyl and 4-tetrazolyl, which group is optionally substituted; or R₈ and R₉, taken together with the nitrogen atom to which they are attached, constitute a dihydrocarbostyril ring (D'):

wherein the nitrogen atom and the phenyl ring may be optionally substituted;

R₅ is hydrogen or methyl; or

R₄ and R₅, taken together with the nitrogen atom to which they are attached, form an optionally substituted azaheterocyclyl ring; and the solvates, hydrates and pharmaceutically acceptable salts thereof.

As used herein the term "alkyl" refers to a straight or branched chain alkyl moiety having from 1 to 10 carbon atoms, including for example, methyl, ethyl, propyl, isopropyl, n-butyl, i-butyl, sec-butyl, tert-butyl, n-pentyl, isopentyl, n-hexyl, n-heptyl and n-octyl. The term "alkylene" refers to an alkyl group as defined above, but connected to the rest of the molecule by two covalent bonds, either at the same or at different carbon atoms, including for example methylene (—CH₂—), 1,2-ethylene (—CH₂—CH₂—) and 1,1-ethylene (—CH(CH₃)—). The term "alkenyl" as used herein refers to a straight or branched chain alkenyl moiety having from 2 to 10 carbon atoms and having in addition one double bond of either E or Z stereochemistry where applicable. Examples of alkenyl groups include: vinyl, allyl, metallyl, butenyl and crotyl. The term "alkenylene" refers to an alkenyl group as defined above, but connected to the rest of the molecule by two covalent bonds, either at the same or at different carbon atoms, including for example 1,2-ethenylene (—CH=CH—) and 1,1-ethenylene (—C(=CH₂)—) and 1,3-propenylene (—CH=CH—CH₂—).

The term "aryl" as used herein refers to a monocyclic or bicyclic aromatic hydrocarbon group of 6 to 10 carbon atoms, such as phenyl, naphthyl, indanyl; furthermore, "aryl" as used herein may refer to a biphenyl group (—C₆H₄—C₆H₅). The term "phenylene" refers to a phenyl group connected to the rest of the molecule by two covalent bonds, i.e. 1,2-C₆H₄ (ortho-phenylene), 1,3-C₆H₄ (meta-phenylene), and 1,4-C₆H₄ (para-phenylene).

The term "cycloalkyl" as used herein refers to a saturated carbocyclic group of 3 to 7 carbon atoms, such as cyclopropyl, cyclobutyl, cyclopentyl, cyclohexyl and cycloheptyl.

The term "heterocyclyl" as used herein refers to a 3- to 7-membered, saturated or unsaturated heterocyclyl ring, containing at least one heteroatom selected from O, S and N, wherein any ring nitrogen may be oxidized as an N-oxide, any ring carbon may be oxidized as a carbonyl, and any ring sulfur may be oxidized as a sulfoxide or sulfone; and wherein said heterocyclyl ring may be optionally fused to a second 5- or 6-membered, saturated or unsaturated heterocyclyl ring, or to a $C_3$–$C_7$ cycloalkyl ring, or to a benzene or naphthalene ring.

Examples of heterocyclyl groups are pyrrolyl, pyrrolidinyl, pyrazolyl, imidazolyl, triazolyl, tetrazolyl, oxazolyl, isoxazolyl, thiazolyl, isothiazolyl, thiadiazolyl, thienyl, tetrahydrothienyl, furyl, tetrahydrofuryl, aziridinyl, oxiranyl, azetidinyl, succinimido, pyridyl, piperidinyl, pyrazinyl, piperazinyl, pyridazinyl, hexahydropyridazinyl, pyrimidinyl, pyranyl, tetrahydropyranyl, benzothienyl, benzothiazolyl, benzoxazolyl, isobenzofuranyl, benzofuranyl, benzimidazolyl, indazolyl, chromenyl, indolyl, oxindolyl, phthalimido, 1-oxo-2-isoindolyl, quinolyl, isoquinolyl, tetrahydroisoquinolyl, indolizinyl, isoindolyl, 2-oxoisoindolyl, 1,2-(methylenedioxy)phenyl, quinuclidinyl, hydantoinyl, saccarinyl, cinnolinyl, purinyl, morpholinyl, thiomorpholinyl, dioxanyl, dithianyl and azepinyl.

The term "azaheterocyclyl" as used herein includes any of the heterocyclyl groups as defined above which contain at least one nitrogen atom and which are linked to the rest of the molecule by a nitrogen atom.

The term "side chain of a naturally occurring α-amino acid" encompasses the side chains of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, and penicillamine, and derivatives thereof wherein any —OH, —SH, —NH, and —NH$_2$ may be alkylated by benzyl or $C_1$–$C_6$ linear or branched alkyl groups, or acylated by benzoyl or $C_2$–$C_7$ linear or branched alkanoyl groups.

The term "side chain of a non-natural a-amino acid" encompasses the side chain of known a-amino acids not belonging to the category of "naturally occurring α-amino acids", such as α-amino-n-butyric acid, α-amino-n-pentanoic acid, α-amino-n-hexanoic acid, α-amino-neohexanoic acid, α-amino-neoheptanoic acid, S-methyl penicillamine sulfoxides and sulfone, tert-butylglycine (alias tert-leucine), (2-methoxy-2-propyl)glycine, (3-methoxy-1-propyl)glycine, phenylglycine, (diphenylmethyl)-glycine, quinolylalanine, isoquinolylalanine, pyridylglycine, (2-pyridyl)alanine, (3-pyridyl)alanine, (4-pyridyl)alanine, adamantylglycine, cyclohexylalanine, cyclohexylglycine, homophenylalanine, naphthylalanine, thienylalanine, homocysteine, homoserine, alloisoleucine, allothreonine and ornithine. Included in this definition, as used herein, are also side chains of natural a-amino acids, as defined above, which are substituted at any carbon atom by one or more substituents selected from chloro, fluoro, hydroxy, methoxy and trifluoromethyl, such as, for example, 3,4-dihydroxyphenylalanine, 5-hydroxylysine and 4-fluorophenylalanine.

In the above definition of $R_1$, a "hydroxymethyl derivative" is an ether, an ester, a carbonate or a carbamate. More particularly, $R_1$ can be —CH$_2$—O—(CH$_2$)$_n$—A, —CH$_2$—O—C(O)—(CH$_2$)$_n$—A, —CH$_2$—O—C(O)—O—(CH$_2$)$_n$—A, —CH$_2$—O—C(O)—NH—(CH$_2$)$_n$—A, or —CH$_2$—O—C(O)—N(A)—(CH$_2$)$_n$—A', wherein n and A are as defined above, and A', being the same or different, is a group A as defined above, and wherein the residue —N(A)—(CH$_2$)$_n$—A' may constitute, in addition, a five- or six-membered azaheterocyclic ring selected from morpholine, pyrrolidine, piperidine, piperazine and hexahydropyridazine, optionally substituted by methyl, phenyl, benzyl, chloro, fluoro, methoxy and carbamoyl. Ether derivatives of such a hydroxymethyl group include the ether derivatives commonly used as hydroxy-protecting groups, such as methoxymethyl ethers and tetrahydropyranyl ethers.

In the above definition of $R_1$, a "mercaptomethyl derivative" is a sulfide, a sulfoxide, a sulfone or a thioester. More particularly $R_1$ can be —CH$_2$—S—(CH$_2$)$_n$—A, —CH$_2$—S(O)—(CH$_2$)$_n$—A, —CH$_2$—S(O)$_2$—(CH$_2$)$_n$—A, or —CH$_2$—S—C(O)—(CH$_2$)$_n$—A, wherein A and n are as defined above.

When $R_1$ and $R_2$, taken together with the carbon atom to which they are attached, form a substituted cyclopropane or oxirane ring, such rings are preferably substituted by one or two substituents selected from $C_1$–$C_3$ alkyl, phenyl and benzyl. When $R_1$ and $R_2$, taken together with the carbon atom to which they are attached, form a substituted 1,3-dioxolane ring, this ring is preferably substituted by one or two substituents selected from $C_1$–$C_3$ alkyl, $C_1$–$C_3$ alkoxy, phenyl and benzyl.

Substituents which may be present in the methyl, alkyl, alkenyl, aryl, cycloalkyl, heterocyclyl and azaheterocyclyl groups in any of the above definitions of $R_1$–$R_7$ include the following:

halo (i.e., fluoro, bromo, chloro or iodo);

hydroxy;

nitro;

azido;

mercapto (i.e., —SH), and acetyl or phenylacetyl esters thereof (i.e., —SCOCH$_3$ and —SCOCH$_2$C$_6$H$_5$);

amino (i.e., —NH$_2$ or —NHR$^I$ or —NR$^I$R$^{II}$ wherein R$^I$ and R$^{II}$, which are the same or different, are straight or branched $C_1$–$C_6$ alkyl, phenyl, biphenyl (i.e., —C$_6$H$_4$—C$_6$H$_5$), or benzyl groups, optionally substituted by hydroxy, methoxy, methyl, amino, methylamino, dimethylamino, chloro or fluoro; or R$^I$ and R$^{II}$ taken together with the nitrogen atom to which they are attached form a heterocyclic ring such as morpholino, pyrrolidino, piperidino, pyperazino or N-methylpyperazino;

guanidino, i.e., —NHC(=NH)NH$_2$;

formyl (i.e. —CHO);

cyano;

carboxy (i.e. —COOH), or esters thereof (i.e., —COOR$^I$), or amides thereof (i.e., —CONH$_2$, —CONHR$^I$ or —CONHR$^I$R$^{II}$), wherein R$^I$ and R$^{II}$ are as defined above, and including morpholino-amides, pyrrolidino-amides, and carboxymethylamides —CONHCH$_2$COOH;

sulfo (i.e., —SO$_3$H);

acyl, i.e., —C(O)R$^I$, wherein R$^I$ is as defined above, including monofluoroacetyl, difluoroacetyl, trifluoroacetyl;

carbamoyloxy (i.e., —OCONH$_2$) and N-methylcarbamoyloxy;

acyloxy, i.e., —OC(O)R$^I$ wherein R$^I$ is as defined above, or formyloxy;

acylamino, i.e., —NHC(O)R$^I$, or —NHC(O)OR$^I$, wherein R$^I$ is as defined above or is a group —(CH$_2$)$_t$COOH where t is 1, 2 or 3;

ureido, i.e., —NH(CO)NH$_2$, —NH(CO)NHR$^I$, —NH(CO)NR$^I$R$^{II}$, wherein R$^I$ and R$^{II}$ are as defined above, including —NH(CO)—(4-morpholino), —NH(CO)—(1-pyrrolidino), —NH(CO)—(1-piperazino), —NH(CO)—(4-methyl-1-piperazino);

sulfonamido, i.e., —NHSO$_2$R$^I$ wherein R$^I$ is as defined above;

a group —(CH$_2$)$_t$COOH, and esters and amides thereof, i.e., (CH$_2$)$_t$COOR$^I$ and —(CH$_2$)$_t$CONH$_2$, —(CH$_2$)$_t$CONHR$^I$, —(CH$_2$)$_t$CONR$^I$R$^{II}$, wherein t, R$^I$ and R$^{II}$ are as defined above;

a group —NH(SO$_2$)NH$_2$, —NH(SO$_2$)NHR$^I$, —NH(SO$_2$)NR$^I$R$^{II}$, wherein R$^I$ and R$^{II}$ are as defined above, including —NH(SO$_2$)—(4-morpholino), —NH(SO$_2$)—(1-pyrrolidino), —NH(SO$_2$)—(1-piperazino), —NH(SO$_2$)—(4-methyl-1-piperazino);

a group —OC(O)OR$^I$, wherein R$^I$ is as defined above;

a group —OR$^I$, wherein R$^I$ is as defined above, including —OCH$_2$COOH;

a group —SR$^I$, wherein R$^I$ is as defined above, including —SCH$_2$COOH;

a group —S(O)R$^I$, wherein R$^I$ is as defined above;

a group —S(O$_2$)R$^I$, wherein R$^I$ is as defined above;

a group —SO₂NH₂, —SO₂NHR', or —SO₂NR'R", wherein R' and R" are as defined above;

C₁–C₆ alkyl or C₂–C₆ alkenyl;

C₃–C₇ cycloalkyl;

substituted methyl selected from chloromethyl, fluoromethyl, difluoromethyl, trifluoromethyl, aminomethyl, N,N-dimethylaminomethyl, azidomethyl, cyanomethyl, carboxymethyl, sulfomethyl, carbamoylmethyl, carbamoyloxymethyl, hydroxymethyl, methoxycarbonylmethyl, ethoxycarbonylmethyl, tert-butoxycarbonylmethyl and guanidinomethyl.

When present, carboxy, hydroxy, mercapto and amino groups may be either free or in a protected form. Protected forms of said groups are any of those generally known in the art, as described, for example, by T. W. Greene in "Protective Groups in Organic Chemistry", Wiley Interscience. Preferably, carboxy groups are protected as esters thereof, in particular methyl, ethyl, tert-butyl, benzyl, and 4-nitrobenzyl esters. Preferably, hydroxy groups are protected as ethers or esters thereof, in particular methoxymethyl ethers, tetrahydropyranyl ethers, benzyl ethers, acetates or benzoates. Preferably, mercapto groups are protected as thioethers or thioesters, in particular tert-butyl thioethers, thioacetates or thiobenzoates. Preferably, amino groups are protected as carbamates, e.g. tert-butoxycarbonyl derivatives, or as amides, e.g. acetamides and benzamides.

The present invention provides the salts of those compounds of formula (I) that have salt-forming groups, especially the salts of the compounds having a carboxylic group, a N-hydroxycarbamoyl group, and a sulfo group, or the salts of the compounds having a basic group, especially an amino or guanidino group. The salts are especially physiologically tolerable salts, for example alkali metal and alkaline earth metal salts (e.g. sodium, potassium, lithium, calcium and magnesium salts), ammonium salts and salts with an appropriate organic amine or amino acid (e.g. arginine, procaine salts), and the addition salts formed with suitable inorganic acids (e.g. hydrochlorides, hydrobromides, sulfates, phosphates) or carboxylic and sulfonic organic acids (e.g. acetates, trifluoroacetates, citrates, succinates, malonates, lactates, tartrates, fumarates, maleates, methanesulfonates, p-toluenesulfonates). Some compounds of formula (I) which contain a carboxylate and an ammonium group may exist as zwitterions; such salts are also part of the present invention.

Furthermore, hydrates, solvates of compounds of formula (I), and physiologically hydrolyzable derivatives (i.e., prodrugs) of compounds of formula (I) are included within the scope of the present invention.

The present invention encompasses all the possible stereoisomers (e.g. diastereoisomers, epimers, geometrical isomers) of the compounds of formula (I), as well as their racemic or optically active mixtures related to the R₁–R₅ substituents.

The present invention also provides a pharmaceutical compositions which comprises, as active ingredient, an amide derivative of formula (I) or a solvate hydrate or pharmaceutically acceptable salt thereof and a pharmaceutically acceptable carrier, diluent or excipient.

Preferred compounds of the present invention are represented by the formula (I')

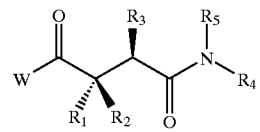

(I')

wherein:

W is —NHOH or —OH;

R₁ is hydroxymethyl or the ether, ester, carbonate and carbamate derivates thereof, as defined above; or R₁ is a mercaptomethyl or the sulfide, sulfone and thioester derivatives thereof, as defined above;

R₂ is hydroxy or a protected derivative thereof; or

R₁ and R₂, taken together with the carbon atom to which they are attached, form a cyclopropane or oxirane ring, optionally substituted by phenyl or benzyl;

R₃ is —CH₂-alkyl, —CH₂-cycloalkyl, —(CH₂)ₙ—O-alkyl, —(CH₂)ₙ—O—cycloalkyl, —(CH₂)ₙ—O—(CH₂)ₙ'—aryl, —(CH₂)ₙO—(CH₂)ₙ'—heterocyclyl, —(CH₂)ₙ—S-alkyl, —(CH₂)ₙ—S-cycloalkyl, —(CH₂)ₙ—S—(CH₂)ₙ'-aryl, —(CH₂)ₙ'—S—(CH₂)ₙ'-heterocyclyl, —(CH₂)ₙ—S(O)-alkyl, —(CH₂)ₙ—S(O)-cycloalkyl, —(CH₂)ₙ—SO₂-alkyl, —(CH₂)ₙ—SO₂-cycloalkyl, —(CH₂)ₙ—SO₂—(CH₂)ₙ'-aryl, —(CH₂)ₙ—SO₂—(CH₂)ₙ'-heterocyclyl, —(CH₂)ₙ—SO₂NH-alkyl, —(CH₂)ₙ—SO₂NH-cycloalkyl, —(CH₂)ₙ—SO₂NH—(CH₂)ₙ'-aryl, —(CH₂)ₙ—SO₂NH—(CH₂)ₙ'-heterocyclyl, —(CH₂)ₙ—CO-alkyl, —(CH₂)ₙ—CO-cycloalkyl, —(CH₂)ₙ—CO—(CH₂)ₙ'-aryl, —(CH₂)ₙ—CO—(CH₂)ₙ'-heterocyclyl, —(CH₂)ₙ—CONH-alkyl, —(CH₂)ₙ—CONH-cycloalkyl, —(CH₂)ₙ—CONH—(CH₂)ₙ'-aryl, —(CH₂)ₙ—CONH—(CH₂)ₙ'-heterocyclyl, —(CH₂)ₙ—NHCO-alkyl, —(CH₂)ₙ—NHCO-cycloalkyl, —(CH₂)ₙ—NHCO—(CH₂)ₙ'-aryl, —(CH₂)ₙ—NHCO—(CH₂)ₙ'-heterocyclyl, —(CH₂)ₙ—NHSO₂-alkyl, —(CH₂)ₙ—NHSO₂-cycloalkyl, —(CH₂)ₙ—NHSO₂—(CH₂)ₙ'-aryl or —(CH₂)ₙ—NHSO₂—(CH₂)ₙ'-heterocyclyl, wherein the said alkyl, cycloalkyl, aryl and heterocyclyl groups are unsubstituted or substituted by one to three substituents selected from chloro, fluoro, hydroxy, methoxy, and C₁–C₄ alkyl; and n and n', being the same or different, are zero or an integer from 1 to 5; more preferably, R₃ is selected from the group consisting of R₃ is isobutyl, cyclopentylmethyl, 3-(4-chlorophenyl) propyl, 3-(4-methoxyphenyl)propyl, 3-(4-biphenyl) propyl, 3-[4-(4-fluorophenyl)phenyl]propyl, 3-[4-(4-chlorophenyl)phenyl]propyl, 3-[4-(4-methoxyphenyl) phenyl]propyl, 3-(4-phenoxyphenyl)propyl, 3-(4-pyridoxyphenyl)propyl, (4-methoxybenzene) sulfonylmethyl, and (4-butoxybenzene)sulfonyl-methyl;

and R₄, R₅ are as defined above.

A first group of particularly preferred compound are those of the formula (I'), w herein W, R₁, of R₂ and R₃ are as defined above, and R₄ is a group of formula (C):

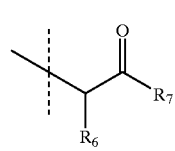

(C)

wherein R₆ is phenyl, pyridyl, isopropyl, sec-butyl, tert-butyl, adamantyl, cylclopentyl, cyclohexyl, cyclohexylmethyl, phenylmethyl, -pyridylmethyl, 3-pyridylmethyl , 4-pyridylmethyl, 2-thienylmethyl, 3-indolylmethyl, 3-(N-methyl)indolylmethyl, 1,1-diphenylmethyl, 1-naphthyl, 2-naphthyl, 1-naphthylmethyl, 2-naphthylmethyl, quinolylmethyl or isoquinolylmethyl, or a derivative thereof substituted by one to three substituents selected from chloro, fluoro, hydroxy, methoxy, carbamoyl and $C_1$–$C_4$ alkyl; or $R_6$ is —C(CH$_3$)$_2$SCH$_3$ or a sulfoxide or sulfone thereof, —C(CH$_3$)$_2$OCH$_3$, —CH$_2$CH$_2$CH$_2$—OCH$_3$, or —CH(CH$_3$)OH or the tert-butyl ether thereof; and wherein $R_7$ is —NH$_2$ or a group —NH—A—, NH—CH$_2$—A or NH—CH$_2$CH$_2$—A, wherein A, being as defined above, is selected from methyl, isopropyl, tert-butyl, phenyl, 4-methoxyphenyl, 4-fluorophenyl, 4-(aminosulfonyl)phenyl, 4-(dimethylaminosulfonylmethyl)phenyl, (3,4-methylenedioxy)phenyl, 2-pyridyl, 3-pyridyl, 4-pyridyl, 4-piperidyl, 2-thiazolyl, 1-naphthyl, 2-naphthyl, 3-quinolyl, 5-quinolyl, 3-isoquinolinyl, 5-isoquinolyl, 3-quinuclidinyl, 2-benzimidazolyl, 5-tetrazolyl, cyclopropyl, cyclobutyl, cyclopentyl, cyclohexyl, 1-morpholino, 1-piperidino, or 1-pyrrolidino; and $R_5$ is hydrogen or methyl.

A second group of particularly preferred compound are those of the formula (I'), wherein W, $R_1$, $R_2$ and $R_3$ are as defined above, and $R_4$ is a group of formula (D):

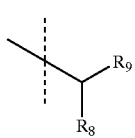

(D)

wherein $R_8$ is methyl, ethyl, phenyl, pyridyl, isopropyl, sec-butyl, tert-butyl, adamantyl, cyclopentyl, cyclohexyl, cyclohexylmethyl, phenylmethyl, 3,4-(methylenedioxy) phenyl, piperonyl, pyridylmethyl, thienylmethyl, 3-indolylmethyl, 3-(N-methyl)indolylmethyl, 1,1-diphenylmethyl, naphthyl, naphthylmethyl, quinolylmethyl, isoquinolylmethyl, thiazolyl, thiazolylmethyl, imidazolyl, imidazolylmethyl, or a derivative thereof substituted by one to three substituents selected from chloro, fluoro, hydroxy, methoxy, and $C_1$–$C_4$ alkyl, or $R_8$ is —C(CH$_3$)$_2$SCH$_3$ or a sulfoxide or sulfone thereof, —C(CH$_3$)$_2$OCH$_3$, —CH$_2$CH$_2$CH$_2$—OCH$_3$, or —CH(CH$_3$)OH or a tert-butyl ether thereof; $R_9$ is either hydrogen or a group selected from methyl, ethyl, phenyl, 3,4-(methylenedioxy)phenyl, piperonyl, pyridyl, benzimidazolyl and 4-tetrazolyl, which group is unsubstituted or substituted by one to three substituents selected from chloro, fluoro, hydroxy, methoxy, methoxy-carbonyl, ethoxycarbonyl and $C_1$–$C_4$ alkyl; or $R_8$ and $R_9$, taken together with the nitrogen atom to which they are attached, constitute a dihydrocarbostyril ring (D'):

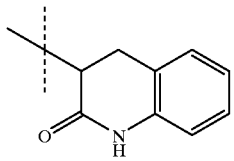

(D')

wherein the nitrogen atom may be substituted by methyl, ethyl, propyl, methoxycarbonyl or ethoxycarbonyl, and the phenyl ring may be substituted by one or two substituents selected from chloro, fluoro, methyl, methoxy or 3,4-methylenedioxy; and $R_5$ is hydrogen or methyl.

A third group of particularly preferred compound are those of the formula (I'), wherein W, $R_1$, $R_2$ and $R_3$ are as defined above, and $R_4$ and $R_5$, taken together with the nitrogen atom to which they are attached, constitute an azaheterocyclic ring selected from morpholine, thiomorpholine, pyrrolidine, piperidine, piperazine, pyridazine, thiazolidine, tetrahydroisoquinoline, hexamethyleneimmine and hexahydropyridazine, either unsubstituted or substituted by one or more substituents selected from methyl, ethyl, phenyl, 4-fluorophenyl, benzyl, alpha-methylbenzyl, hydroxy, hydroxymethyl, and carbamoyl, or by a group —CONH—A wherein A is selected from methyl, isopropyl, tert-butyl, cyclopropyl cyclobutyl, cyclopentyl, cyclohexyl, phenyl, 4-fluorophenyl, 4-chlorophenyl, 4-methoxyphenyl, 2-pyridyl, 3-pyridyl, 4-pyridyl, 4-piperidyl, 2-thiazolyl, 1-naphthyl, 2-naphthyl, 3-quinolyl, 5-quinolyl, 3-isoquinolinyl, 5-isoquinolyl, 3-quinuclidinyl, 3,4-(methylenedioxy)phenyl and piperonyl.

When $R_1$ is a hydroxymethyl derivative, it is preferably —CH$_2$OCH$_3$, —CH$_2$—O—(tetrahydropyranyl), —CH$_2$OCOCH$_3$, —CH$_2$OCOC(CH$_3$)$_3$, —CH$_2$OCONH$_2$, —CH$_2$OCONHCH$_3$, —CH$_2$OCON(CH$_3$)$_2$, —CH$_2$OCONH-cyclohexyl, —CH$_2$OCON(CH$_3$)-cyclohexyl, —CH$_2$—O—CO-morpholino, —CH$_2$—O—CO-pyrrolidino, —CH$_2$—O—CO-piperidino; or it is —CH$_2$OCH$_2$Ph, —CH$_2$OCOPh, —CH$_2$OCOCH$_2$Ph, —CH$_2$OCONHCH$_2$Ph or a derivative thereof wherein the Ph group is substituted by one, two or three substituents selected from chloro, fluoro, hydroxy, $C_1$–$C_4$ alkoxy, methyl and carbamoyl, or by 3,4-dioxymethylene.

When $R_1$ is a mercaptomethyl derivative, it is preferably a group —CH$_2$S—COCH$_3$, —CH$_2$S—COPh, —CH$_2$S—CH$_3$, —CH$_2$S—Ph, —CH$_2$S—CH$_2$Ph, —CH$_2$SO$_2$—CH$_3$, —CH$_2$SO$_2$—Ph, —CH$_2$SO$_2$—CH$_2$Ph, —CH$_2$S-thienyl, —CH$_2$S—(1-methyl-1,2,3,4-tetrazol-5-yl), or a derivative thereof wherein the Ph group is substituted by one or two substituents selected from chloro, fluoro, hydroxy, $C_1$–$C_4$ alkoxy, methyl and carbamoyl, or by 3,4-dioxymethylene. Preferred compound are also those of the formula (I'), wherein W is either —NHOH or OH; $R_1$ is either hydroxymethyl or mercaptomethyl, or it is a hydroxymethyl derivative as defined above, or it is a mercaptomethyl derivative as defined above;

$R_2$ is hydroxy; $R_3$ is isobutyl, cyclopentylmethyl, 3-(4-chlorophenyl)propyl, 3-(4-methoxyphenyl)propyl, 3-(4-biphenyl)propyl, 3-[4-(4-fluorophenyl)phenyl]propyl, 3-[4-(4-chlorophenyl)phenyl]propyl, 3-[4-(4-methoxyphenyl)phenyl]propyl, 3-(4-phenoxyphenyl)propyl, 3-(4-pyridoxyphenyl)propyl, (4-methoxybenzene)sulfonylmethyl, and (4-butoxybenzene)sulfonylmethyl; and $R_4$ and $R_5$ are as defined above.

Compounds of the general formula (I) and their salts may be prepared by any suitable method known in the art, or by the following process which forms another aspect of the present invention. In the description and formulae below, the groups $R_1$, $R_2$, $R_3$, $R_4$ and $R_5$ are as defined above. It is understood that in the processes below any functional group (e.g. carboxyl, hydroxyl, mercapto or amino), if needed or desired, can be masked by conventional methods and unmasked at the end or when convenient. Suitable protecting groups for such functionalities will be apparent to those skilled in the art and are well described in the chemical literature (see, for example: "Protective Groups in Organic Synthesis" by T. W. Greene, Wiley Interscience). It is also understood that the groups $R_1$, $R_2$, $R_3$, $R_4$ and $R_5$ may be converted by conventional methods into different groups included within those previously defined, if desired, at the end or at any stage of the process below. These conversions are known or will be apparent to those skilled in the art and are well described in the chemical literature (see, for example: "Comprehensive Organic Transformation" by R. C. Larock, VCH Publishers). Accordingly, the present invention provides a process for producing a compound of the invention as defined above, which process comprises:

(a) coupling an acid of formula (II), or a salt thereof,

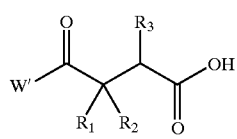

(II)

wherein $R_1$, $R_2$ and $R_3$ are as defined in claim 1 and W' is protected —OH or protected —NHOH, with an amine of formula (III) or a salt thereof

(III)

wherein $R_4$ and $R_5$ are as defined above, to obtain a compound of formula (Ia)

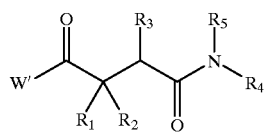

(Ia)

wherein $R_1$, $R_2$, $R_3$, $R_4$, $R_5$ and W' are as defined above, and then removing the protecting group from this compound to yield a compound of formula (I) wherein W is —OH or —NHOH or a salt thereof; or (b) converting a compound of formula (IV)

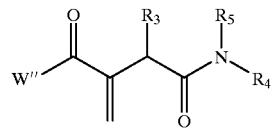

(IV)

wherein W" is OH or W', and $R_3$, $R_4$, $R_5$ and W' are as defined above, into a compound of formula (IV or (Ia) as defined above, and then, when a compound of formula (Ia) is obtained, removing the protecting group from this compound to yield a compound of formula (I) wherein W is —OH or —NHOH, or a salt thereof; or (c) condensing a lactone of formula (V)

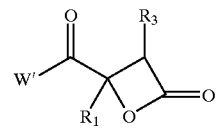

(V)

wherein W', $R_1$ and $R_3$ are as defined above, with an amine of formula (III) as defined above, to obtain a compound of formula (Ia) as defined above wherein $R_2$ is hydroxy, and then removing the protecting group from this compound to yield a compound of formula (I) wherein W is —OH or —NHOH and $R_2$ is hydroxy; or (d) condensing a lactone of formula (VI):

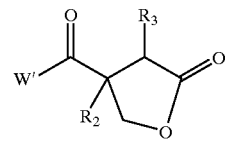

(VI)

wherein W', $R_2$ and $R_3$ are as defined above, with an amine of formula (III) as defined above, to obtain a compound of formula (Ia) above wherein $R_1$ is hydroxymethyl, and then removing the protecting group from this compound to yield a compound of formula (I) wherein W is —OH or —NHOH and $R_1$ is hydroxymethyl and, if desired, (e) converting one compound of formula (I) or (Ia) into another compound of formula (I) or (Ia) and/or converting a compound of formula (I) into a pharmaceutically acceptable salt thereof, and/or converting a salt of a compound of formula (I) into the free compound.

When in compounds of formula (Ia), (II), (IV), (V) and (VI) above W' is protected —OH, it is preferably benzyloxy, p-nitrobenzyloxy, p-methoxybenzyloxy, tert-butoxy, benzhydryloxy, trityloxy, trimethylsilyloxy, tert-butyldimethylsilyloxy, tert-butyldiphenylsilyloxy, phenyldimethylsilyloxy, allyloxy, methoxy and ethoxy. Conversion of compounds of formula (Ia) wherein W' is protected —OH, obtained by process variants (a)–(d) above, into compounds of formula (I) wherein W is —OH or salts thereof, entails deprotection of said protected —OH groups. This conversion is carried out by methodologies well known in the art, as generally referred to above, for the removal of protecting groups from protected carboxylic acids. A preferred conversion of this type is hydrogenolysis, especially in the presence of a palladium catalyst, in an inert organic solvent such as ethanol or DMF or the like, especially at room temperature and under atmospheric pressure or moderate pressure, which is suitable for the conversion, e.g., of benzyl and p-nitrobenzyl esters into the parent carboxylic acids. Another preferred conversion of this type is acid hydrolysis, especially by hydrochloric acid or trifluoroacetic acid, in inert organic solvents such as dichloromethane, THF, acetonitrile and the like, optionally in admixture with water, methanol or ethanol, at temperatures ranging from from −20 to +40° C. Hydrolysis by trifluoroacetic acid, in particular, is suitable for the conversion of tert-butyl esters and p-methoxybenzyl esters into the parent carboxylic acids, and may be carried out in the presence of scavangers of the tert-butyl cation, such as anisole, methanol, ethanol and water. A third preferred conversion of this type, suitable for the deprotection of allyl esters, is treatment with a palladium (0) compound such as tetrakis-(triphenylphosphine)-palladium(0). A fourth preferred conversion of this type, suitable for the conversion of alkyl esters, e.g. methyl, ethyl, propyl, i-propyl, n-butyl esters, into the parent carboxylic acids, is saponification in an alkaline medium, e.g. by NaOH or LiOH in a mixture of water and methanol.

When in compounds of formula (Ia), (II), (IV), (V) and (VI) above W' is protected —NHOH, it is either a group —NH—O—$R_{10}$, or a group —N($R_{11}$)—O—$R_{10}$, wherein $R_{10}$ and $R_{11}$ are, respectively, hydroxy and amino protecting groups known in the art. Such groups are removed, by conventional methods known in the art, from a compound of formula (Ia) obtained by process variants (a)–(d) above, to obtain the desired final compound of formula (I) wherein W is —NH—OH. Preferred $R_{10}$ and $R_{11}$ groups, which may be the same or different, are those removable by hydrogenolysis or by mild hydrolysis, including, in particular, benzyl, 4-methoxybenzyl, 4-nitrobenzyl, tert-butyl, tert-butoxycarbonyl, tetrahydropyranyl, trityl, trimethylsilyl and tert-butyldimethylsilyl. Removal of such $R_{10}$ and $R_{11}$ groups from compounds of formula (Ia) wherein W' is either —NH—O—$R_{10}$ or —N($R_{11}$)—O—$R_{10}$ to obtain compounds of formula (I) wherein W is —NH—OH is performed under conditions generally known in the art for obtaining hydroxamic acids, or salts thereof, from N-protected, O-protected, or N,O-diprotected hydroxamic acid derivatives. For example, benzyl, 4-methoxybenzyl and 4-nitrobenzyl groups may be removed, preferably, by catalytic hydrogenation, preferably in the presence of a palladium catalyst such as palladium on charcoal or palladium hydroxide; 4-methoxybenzyl, trityl, tert-butyl, tert-butoxycarbonyl and tetrahydropyranyl groups may be removed, preferably, by mild acid hydrolysis; trimethylsilyl and tert-butyldimethylsilyl groups may be removed by aqueous workup or by mild acid treatment. In addition, a 4-nitrobenzyl group may be removed by dissolving metal reduction, preferably by zinc or iron powder, and a tert-butyldimethylsilyl group may be removed by a fluoride reagent, preferably by tetrabutylammonium fluoride.

In process variant (a), the coupling between an acid of formula (II) or a salt thereof with an amine of formula (III) or a salt thereof to give a compound of formula (Ia) as defined above is carried out in a manner which is known per se in peptide chemistry. Thus, for example, the condensation can be carried out according to the well-known acid halide, acid anhydride, activated amide, mixed anhydride, or activated ester method.

In a preferred procedure, the condensation is carried out according to the acide chloride method, in particular by converting the acid of formula (II) into the corresponding acid chloride by the action of oxalyl chloride or thionyl chloride. In another preferred procedure, the condensation is carried out by the activated ester method. Particularly preferred activated esters are the hydroxybenzotriazolyl, hydroxysuccinyl and pentafluorophenyl esters, which are obtained by reaction of the acid with the corresponding alcohol in the presence of a dehydrating agent, for example N,N'-dicyclohexyl carbodiimide (hereinafter DCC), N,N-dimethylaminopropyl-N'-ethyl carbodiimide hydrochloride (EDC), bis(2-oxo-3-oxazolidinyl)phosphinic chloride (BOP-Cl), or 2-ethoxy-1-ethoxycarbonyl-1,2-dihydroquinoline (EEDQ). Activated esters with 1-hydroxybenzotriazole (HOBT) can be obtained and reacted in situ by use, as the condensing agent, of benzotriazolyl-1-yloxy-tris(dimethylamino)phosphonium hexafluorophosphate (BOP reagent), Q-benzotriazol-yl-N, N,N',N'-tetramethyluronium hexafluorophosphate (HBTU), and O-benzotriazol-yl—N,N,N',N'-tetramethyluronium tetrafluoroborate (TBTU). Preferred mixed anhydrides are those obtained by reacting the acid or a salt thereof with a chlorocarbonate, such as ethyl chlorocarbonate, or with an acid halide, such as pivaloyl chloride. In a still another preferred procedure, the condensation between the acid of formula (II) or a salt thereof and the amine of formula (III) or a salt thereof is carried out directly in the presence of a known peptide coupling reagent, such as DDC, EDC, BOP-Cl or EEDQ, as mentioned before. Preferred conditions for the condensation in the presence of DCC are illustrated in example 13, in the presence of DCC and HOBT in examples 4 and 9, in the presence of DCC and EDC in examples 16, 22 and 25. The amines of formula (III) are known compounds, or can be obtained from known compounds by known procedures. The succinic acid derivatives of formula (II) are novel compounds and are therefore a further object of the present invention. They can be obtained by reacting known compounds of formula (VII) or a derivative thereof protected at the terminal carboxy group, i.e. that in allylic position to the double bond:

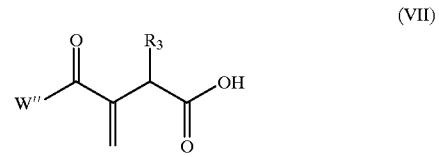

(VII)

wherein W" and $R_3$ are as defined above, with appropriate reagents followed by removal and/or introduction of the appropriate protecting groups and/or conversion into different compounds of the formula (II).

For example, the acids of formula (II) wherein W' and $R_3$ are as defined above, and $R_1$ and $R_2$, together with the carbon atom to which they are attached, constitute a cyclopropyl or substituted cyclopropyl ring (formula B1 above), are obtained by cycloaddition of diazomethane, or a substituted derivative thereof, to a vinylene compound of formula (VII) as above defined, or a derivative thereof protected at the terminal carboxy group, followed by extrusion of nitrogen and removal of the protecting group, if present. This reaction can be performed by any of the conditions known in the art for the cyclopropanation of double C—C bonds. Particularly preferred conditions are treatment of a protected derivative of the vinylene compound of formula (VII), especially a benzyl or tert-butyl ester thereof, with diazomethane, in an inert organic solvent, such as dichloromethane, at temperatures ranging from 0 to +40° C., followed by irradiation (300 nm or above) until extrusion of nitrogen is complete.

The acids of formula (II) wherein W' and $R_3$ are as defined above, $R_1$ is —$CH_2OH$ and $R_2$ is —OH, can be prepared by reacting a vinylene compound of formula (VII) above, or a derivative thereof protected at the terminal carboxy group, with an oxidizing agent, known per se as a conventional reagent in the transformation of vinylene groups (>C=$CH_2$) into glycols (>COH—$CH_2OH$), followed by removal of protecting groups, if present.

A particularly preferred oxidizing agent for such conversion is N-methylmorpholine-N-oxide, in the presence of a catalytic amount of osmium tetroxide, in an inert organic solvent, or in a mixture of an inert organic solvent and water, which is preferably aqueous acetone, at a temperatures from 0° C. to reflux.

The acids of formula (II), or esters thereof, wherein W' and $R_3$ are as described above, $R_2$ is hydroxy or a protected derivative thereof, and $R_1$ is a hydroxymethyl derivative, that is an ester, an ether, a carbonate or a carbamate, can be obtained from the corresponding compounds of formula (II) wherein $R_1$ is hydroxymethyl, or derivatives thereof protected at the terminal carboxy group, by conditions known in the art for the conversion of primary carbinols into esters, ethers, carbonates and carbamates, followed by removal of the protecting group, if present. Specific examples are given in Preparations 4 and 5. The acids of formula (II), or esters thereof, wherein W' and $R_3$ are as described above, $R_2$ is hydroxy or a protected derivative thereof, and $R_1$ is a mercaptomethyl or a mercaptomethyl derivative, that is a sulfide (i.e., a thioether), a thioester, a sulfoxide or a sulfone, can be obtained from the corresponding compounds of formula (II) wherein $R_1$ is hydroxymethyl, by conditions known in the art for the conversion of primary carbinols into the corresponding primary mercaptanes, thioesters or sulfides. A preferred condition for the conversion of compounds of formula (II) wherein $R_1$ is hydroxymethyl into corresponding thioethers, that is compounds of formula (II) wherein $R_1$ is —$CH_2$—S—A, being A as described above, comprises protection of the carboxy group, followed by reaction with a mercaptane of formula A—SH under Mitsunobu conditions, that is in the presence of a phosphine (expecially, triphenylphosphine) and an azodicarboxylate (expecially, diethyl azodicarboxylate), and removal of the carboxy protecting group. Sulfone and sulfoxide derivatives are preferably obtained by oxidation of the above intermediates wherein $R_1$ is —$CH_2$—S—A with an oxidizing agent, known in the art for converting sulfides into sulfoxides and sulfones. Similarly, a preferred condition for the conversion of compounds of formula (II) wherein $R_1$ is hydroxymethyl into corresponding thioesters, that is compounds of formula (II) wherein $R_1$ is —$CH_2$—S(CO)—A, being A as described above, comprises protection of the carboxy group, followed by reaction with a thioacid of formula A-COSH under Mitsunobu conditions, and removal of the carboxy protecting group. A preferred condition for the conversion of compounds of formula (II) wherein $R_1$ is hydroxymethyl into corresponding mercaptanes, that is compounds of formula (II) wherein $R_1$ is —$CH_2$—SH, comprises hydrolysis of the acetic thioesters thereof, that is compounds of formula (II) wherein $R_1$ is —$CH_2$—$SCOCH_3$, in turn prepared as described above, under general conditions known in the art.

The acids of formula (II) wherein W' and $R_3$ are as defined above, and $R_1$ and $R_2$, together with the carbon atom to which they are attached, constitute an oxyrane or substituted oxyrane ring (formula B2 above), are obtained by reacting a vinylene compound of formula (VII) above, or a derivative thereof protected at the terminal carboxy group, with a peroxide, known per se as a conventional reagent for the epoxidation of vinylene groups (>C=$CH_2$), followed by removal of protecting groups, if present. Alternatively, these epoxides can be obtained from compounds of formula (II) wherein $R_1$ is hydroxymethyl and $R_2$ is hydroxy, protected at the terminal carboxy group, by intramolecular condensation under Mitsunobu conditions, that is in the presence of a phosphine (expecially, triphenylphosphine) and an azodicarboxylate (expecially, diethyl azodicarboxylate), followed by removal of the carboxy protecting group.

The vinylene intermediates of formula (VII) are either known compounds, or can be obtained from known compounds by known methods, as evident to the one skilled in the art and as illustrated herebelow. A preferred method for obtaining intermediate compounds of formula (VII) is decar boxylative methylenation, for example by reacting malonic acids of formula (VIII), or derivatives thereof protected at the terminal carboxy group:

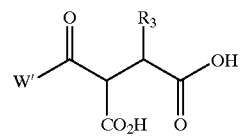

(VIII)

wherein W' and $R_3$ are as defined above, with formaldehyde, preferably in the presence of piperidine, followed by optional removal of protecting groups, if present; this reaction is illustrated in preparation 2. The intermediates of formula (VIII) are known compounds, or can be prepared from known compounds by procedures well known per se. Particularly preferred compounds of formula (VIII), for use in the preparation of the preferred compounds of formula (I) wherein the stereochemistry of the carbon atom bearing the $R_3$ group is the one described in formula (I'), are compounds of formula (VIII'):

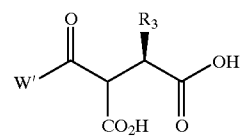

(VIII')

wherein W' and $R_3$ are as defined above, which can be prepared from their carboxy-protected derivates of formula (IX):

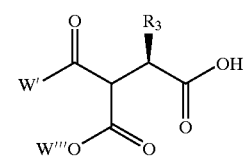

(IX)

wherein W' and $R_3$ are as defined above, and W'" is a carboxy-protecting group, preferably benzyl, 4-methoxybenzyl, 4-nitrobenzyl, benzhydryl, tert-butyl and methyl, by removal of said carboxy-protecting group by known methods, that is by acid or alkaline hydrolysis, or by hydrogenolysis. Intermediates of formula (IX) wherein $R_3$ is isobutyl are known compounds; analogs wherein $R_3$, being as described above, is different from isobutyl can be prepared by the same described procedures, or by methods known in the art. In particular, intermediate compounds of formula (IX) wherein W' and W'" are benzyl are prepared starting from a (D)-aminoacid of formula $H_2N$—$CH(R_3)$—COOH, by a process comprising deaminative bromination, protection of the carboxy group, condensation with dibenzyl malonate, and removal of the protecting group. Alternatively, intermediates of formula (IX) are obtained as the racemates, starting from racemic natural or non-natural aminoacids, by the same procedure detailed above, and at the end the obtained racemates are optically resolved by crystallization with S-(−)-1-phenylethylamine, as illustrated in Preparation 1, to provide compounds of formula (IX) as the pure stereoisomers (that is, in the R configuration).

In process variant (b), the conversion of a vinylene compound of formula (IV) as described above into a compound of formula (I) or (Ia) is carried out according to the same procedures described above for the conversion of an intermediate of formula (VII) into the corresponding intermediate of formula (II); that is, the vinylene group (>C=CH$_2$) is, by use of the appropriate reagent, converted either into a cyclopropane ring, an oxirane ring, a group >C(OH)—CH$_2$OH and ether, ester, carbonate or carbamate derivatives thereof, or a group >C(OH)—CH$_2$SH and sulfide, sulfoxide, sulfone and thioester derivatives thereof. Some of the preferred conditions are illustrated in the Examples. Thus, the conversion of a compound of formula (IV) into a compound of formula (I) wherein R$_1$ and R$_2$, taken together with the carbon atom to which they are attached, constitute a cyclopropane ring is illustrated in Example 20. The conversion of a compound of formula (IV) into a compound of formula (I) wherein R$_1$ and R$_2$, taken together with the carbon atom to which they are attached, constitute an oxyrane ring is illustrated in Example 21. The conversion of a compound of formula (IV) into a compound of formula (I) wherein R$_1$ is hydroxymethyl or protected hydroxymethyl, and R$_2$ is hydroxy or protected hydroxy, is illustrated in examples 1 and 4. The conversion of a compound of formula (IV) into a compound of formula (I) wherein R$_1$ is a thioether derivative of —CH$_2$—SH (i.e., a sulfide) and R$_2$ is hydroxy is illustrated in Example 18.

In process variant (c), condensation of a lactone of formula (V) with an amine of formula (III) to afford a compound of formula (I) or (Ia) wherein R$_2$ is hydroxy is carried out in an inert organic solvent, optionally in the presence of an inorganic or organic base, at a temperature from 0° C. to reflux temperature, optionally in the presence of a catalytic amount of a reagent used in peptice chemistry for the formation of activated esters, preferably HOBT. The inert organic solvent is typically tetrahydrofuran, acetonitrile, DMF, DMSO, dichloromethane, ethanol or mixtures thereof, and the optional inorganic or organic base is typically potassium carbonate, cesium carbonate, triethylamine or dimethylaminopyridine. Typical conditions of process variant (c) are illustrated in Example 14. The lactones of formula (V) are novel compounds and are part of the present invention. Accordingly, the present invention further provides a compound of formula (V):

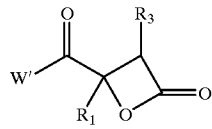

(V)

wherein W', R$_1$ and R$_3$ are as defined above, for use in the preparation of a compound of formula (I) according to process variant (c) described above. The lactones of formula (V) are prepared from compounds of formula (II) as defined above wherein R$_2$ is hydroxy and W', R$_1$ and R$_3$ are as defined above, by intramolecular condensation (dehydration) between the hydroxy group represented by R$_2$ and the terminal carboxy group, such condensation being carried out in an inert organic solvent such as acetonitrile or dichloromethane, in the presence of a dehydrating agent such as dicyclohexyl carbodiimide or a water-soluble carbodiimide, for instance as described in Preparation 9, or by treating said compound of formula (II) wherein R$_2$ is hydroxy with hydroxybenzotriazole or TBTU or with carbonyldiimidazole, or by exposing said compounds of formula (II) under Mitsunobu conditions, that is with triphenylphosphine and diethyl azodicarboxylate.

In process variant (d), condensation of a lactone of formula (VI) and an amine of formula (III) is accomplished by mixing the reagents in an inert organic solvent, optionally in the presence of an inorganic or organic base, at a temperature from 0° C. to reflux temperature. The inert organic solvent is typically tetrahydrofuran, acetonitrile, DMF, DMSO, dichloromethane, ethanol or mixtures thereof. The optional inorganic or organic base is typically potassium carbonate, cesium carbonate, triethylamine or dimethylaminopyridine. Example 24, Route B, typically illustrates process variant (d).

The lactones of formula (VI) are novel compounds and are part of the present invention. Accordingly, the present invention further provides a compound of formula (VI):

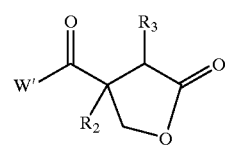

(VI)

wherein W', R$_2$ and R$_3$ are as defined above, for use in the preparation of compounds of formula (I) according to process variant (d) detailed above. The lactones of formula (VI) are prepared from compounds of formula (IIa), or an ester thereof:

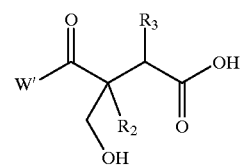

(IIa)

wherein W', R$_2$ and R$_3$ are as defined above, by intramolecular condensation between the hydroxymethyl group and the terminal carboxy group, or an ester thereof. This condensation is usually spontaneous at room temperature, that is the lactones of formula (VI) are directly obtained from ester derivatives of compounds of formula (IIa) under conventional conditions of ester hydrolysis, as detailed above. Alternatively, such intramolecular condensation can be aided by exposing the compounds of formula (IIa) to dehydrating agents, or to Mitsunobu conditions, or under conventional conditions for converting a carboxylic acid into an "activated ester" thereof, as defined above. It is to be noted that the compounds of the formula (II) the present invention also encompasses the acids of formula (IIa) and the esters thereof, in particular the tert-butyl, benzyl, p-nitrobenzyl and p-methoxybenzyl esters, which may be prepared as described above. Specific examples of the preparation of said lactones are given in Preparations 6–8.

Part of the process of the present invention is also the conversion of one compound of formula (I) into another compound of formula (I), for instance the conversion of a compound of formula (I) wherein W is —OH or a salt thereof, obtained by any of the process variants (a)–(d), into a compound of formula (I) wherein W is —NHOH or a salt thereof. This conversion is carried out by methodologies well known in the art for the general conversion of carboxylic acids or salts thereof into hydroxamic acids or salts thereof. Typically, a compound of formula (I) wherein W is —OH, or a salt thereof, and wherein any reactive functional group which may be present in substituents R$_1$–R$_4$ is protected if necessary or convenient, is condensed with hydroxylamine or a salt thereof, or with an O-protected hydroxylamine of formula $R_{10}$—O—$NH_2$ or a salt thereof, or with an N,O-diprotected hydroxylamine of formula $R_{10}$—O—NH—$R_{11}$ or a salt thereof, wherein $R_{10}$ and $R_{11}$, as stated above, are, respectively, hydroxy- and amino-protecting groups known in the art, to obtain a compound of formula (Ia) wherein W' is either —NH—OH, —NH—$OR_{10}$ or —N($R_{11}$)—$OR_{10}$, and $R_1$-$R_5$ are as detailed above, and wherein any reactive functional group which may be present in substituents $R_1$-$R_5$ is protected if necessary or convenient. The obtained compounds of formula (Ia) specified above are then converted into the desired compounds of formula (I) by removal of said protecting groups $R_{10}$ and $R_{11}$, if present, and of any protecting group which may be present on the substituents $R_1$-$R_5$. Preferred $R_{10}$ and $R_{11}$ groups, which may be the same or different, are those removable by hydrogenolysis or by mild hydrolysis, including, in particular, benzyl, 4-methoxybenzyl, 4-nitrobenzyl, tert-butyl, tert-butoxycarbonyl, tetrahydropyranyl, trityl, trimethylsilyl and tert-butyldimethylsilyl. Thus, an O-protected hydroxylamine is, typically, O-benzyl-hydroxylamine, O-(4-methoxybenzyl) hydroxylamine, O-(4-nitrobenzyl)-hydroxylamine, O-trimethylsilyl-hydroxylamine, O-(tert-butyldimethylsilyl)-hydroxylamine, O-(tert-butyl)-hydroxylamine, O-(tert-butoxycarbonyl)-hydroxylamine, O-trityl-hydroxylamine, or O-tetrahydropyranyl-hydroxylamine. An N,O-diprotected hydroxylamine is, preferably, N,O-bis(benzyl)-hydroxylamine, N,O-bis(4-methoxybenzyl)-hydroxylamine, N,O-bis(tert-butoxycarbonyl)-hydroxylamine, N-(tert-butoxycarbonyl)—O—(tert-butyl-dimethylsilyl)-hydroxylamine, and N-(tert-butoxycarbonyl)—O—(tetrahydropyranyl)-hydroxylamine. Condensation between a compound of formula (I) wherein W is —OH or a salt thereof and hydroxylamine or a protected hydroxylamine or salts thereof can be carried out in a variety of conditions. Thus, the carboxyl group of the compounds of formula (I) wherein W is —OH or a salt thereof may be converted, either in situ or in a distinct step, into an "activated derivative" thereof, which then reacts with the hydroxylamine, protected hydroxylamines or salts thereof which are either added or already present in the reaction mixture. "Activated derivatives" of carboxylic acids of formula (I) wherein W is —OH are the acid chloride, mixed anhydrides, and esters thereof. In particular, the acid chloride is obtained by reacting the acid or a salt thereof with a reagent such as oxalyl chloride or thionyl chloride; mixed anhydrides are obtained by reacting the acid or a salt thereof with a chlorocarbonate, such as ethyl chlorocarbonate, or with an acid halide, such as pivaloyl chloride; esters, which are, preferably, the methyl, ethyl, pentafluorophenyl, hydroxysuccinyl, or hydroxybenzotriazolyl esters, are obtained by reaction of the acid with the corresponding alcohol in the presence of a dehydrating agent, for example DCC, EDC, BOP reagent, HBTU, TBTU, EEDQ. Alternatively, carboxylic acids of formula (I) wherein W is —OH, or salts thereof, are directly condensed with hydroxylamine, protected hydroxylamines or salts thereof, in the presence of condensing agents known in the art and used for peptide coupling, preferably BOP reagent, BOP-Cl, HBTU, TBTU, DCC and EDC. Preferably, the condensation reaction is carried out in an inert organic solvent, such as DMF, THF, acetonitrile, dichloromethane or toluene at a temperature from −20 to +60° C., optionally in the presence of a tertiary organic base. When protected hydroxylamines are employed, the reaction affords compounds of formula (Ia) above, wherein W' is protected —NHOH. These compounds of formula (Ia) wherein W' is protected —NHOH are then converted into compounds of formula (I) wherein W is —NHOH, or salts thereof, by removing such protecting groups, as detailed above. For example, benzyl, 4-methoxybenzyl and 4-nitrobenzyl groups may be removed, preferably, by catalytic hydrogenation, preferably in the presence of a palladium catalyst such as palladium on charcoal or palladium hydroxide; 4-methoxybenzyl, trityl, tert-butyl, tert-butoxycarbonyl and tetrahydropyranyl groups may be removed, preferably, by mild acid hydrolysis; trimethylsilyl and tert-butyldimethylsilyl groups may be removed by aqueous workup or by mild acid treatment. In addition, a 4-nitrobenzyl group may be removed by dissolving metal reduction, preferably by zinc or iron powder, and a tert-butyldimethylsilyl group may be removed by a fluoride reagent, preferably by tetrabutylammonium fluoride.

Compounds of formula (I) and intermediates of formula (Ia) or (II) wherein $R_2$ is —OH and $R_1$ is —$CH_2OH$ also serve as useful intermediates in the preparation of compounds of formula (I) wherein $R_2$ is —OH and $R_1$ is either a hydroxymethyl derivative, that is an ether, an ester, a carbonate or a carbamate thereof, or it is mercaptomethyl or a mercaptomethyl derivative, that is a thioether, a thioester, a sulfide, a sulfoxide or a sulfone thereof. This conversion can be achieved by a method comprising (i) optional protection of reactive functional groups anywhere in the molecule; (ii) conversion of the hydroxymethyl group $R_1$ into a new group $R_1$ to be selected among those defined above, or a protected derivative thereof, by methodologies known per se in the general chemistry of primary carbinols; (iii) optional removal of protecting groups, when present. More in particular, the selected class of compounds of formula (I) wherein $R_1$ is a hydroxymethyl derivative can be obtained by using in step (ii) above reagents and conditions known per se to afford ethers, esters, carbonates and carbamates from primary carbinols, for example, by methods described in "Comprehensive Organic Transformation" by R. C. Larock, VCH Publishers. Similarly, the selected class of compounds of formula (I) wherein $R_1$ is either mercaptomethyl or a mercaptomethyl derivative can be obtained by using in step (ii) above reagents and conditions known per se to afford mercaptanes, thioethers, thioesters, sulfoxides and sulfones from primary carbinols, either directly of by the intermediacy of first-obtained mercaptanes or thioethers.

As mentioned above, although low molecular weight MMP inhibitors, including hydroxamates of general formula (A), are already known, there is a strong need for better and diversified molecules for their use in medicine, that is in particular in the control or prevention of degenerative joint diseases such as rheumatoid arthritis and osteoarthritis, or in the management of multiple sclerosis, or in the treatment of invasive tumors. We found that the compounds of formula (I) provided by the present invention, and in particular the compounds having the preferred stereochemistry represented in formula (I'), are characterized by high inhibitory activity on the matrix metalloproteinases, especially collagenases, gelatinases and stromelysins. For example, the following protocol was used to assess the biochemical activity of compounds of formula (I) against MMP-1, MMP-2, and MMP-3 (respectively, human interstitial collagenase, gelatinase A, and stromelysin-1).

Biochemical Assay (Protocol A)

The in vitro potency of the compounds of the present invention as competitive inhibitors of selected matrix metalloproteinases was determined as described below. Human collagenase (MMP-1) was obtained as truncated recombinant enzyme encompassing residues 101–269 and did not require activation. Human gelatinase-A (MMP-2) was obtained as pro-enzyme (72 kDa) and was activated with 1 mM 4-aminophenylmercuric acetate for 30 min at 37° C. immediately prior to use. Human stromelysin-1 (MMP-3) was obtained as a recombinant pro-enzyme isolated either from E. coli or from baculovirus infected Sf9 insect cells and activated either by heat (1 h, 55° C.) or by 5 mg/l trypsin (30 min, 37° C.) before addition of soybean trypsin inhibitor, finally removed by centrifugation.

All enzyme assays to determine values of the enzyme-inhibitor dissociation constants were performed using the peptide substrate (7-methoxycoumarin-4-yl)Acetyl-Pro-Leu-Gly-Leu-(3-[2,4-dinitrophenyl]-L-2,3-diaminopropionyl)-Ala-Arg-NH$_2$ (Mca-Pro-Leu-Gly-Leu-Dpa-Ala-Arg—NH$_2$) (C. G. Knight et al., FEBS Lett. 296:263–266, 1992). The enzymes cleave at the Gly-Leu bond removing the internally quenching Dpa group. The release of the highly fluorescent peptide Mca-Pro-Leu was followed fluorimetrically setting the excitation wavelength at 326 nm (bandwidth 5 nm) and the emission at 392 nm (bandwidth 20 nm).

Continuous fluorescence assay was carried out using a Perkin Elmer LS-50 Fluorescence Spectrophotometer fitted with a thermostatted four position stirring cell changer. Inhibitors were dissolved in the assay buffer (50 nM Tris/HCl pH 7.4 containing 0.15 M NaCl, 10 mM CaCl$_2$, 0.01 mM ZnCl$_2$ and 0.05% Brij 35) thermostatted at 37° C. The reaction was started by the addition of substrate (2 mM), followed by the addition of the enzyme (e.g. 1.0 nM collagenase, 0.04 nM gelatinase, or 3.0 nM stromelysin) and the increase in fluorescence was monitored over 30 min. The run was repeated at different concentrations of inhibitors in the range 0.1–10000 nM and data at inhibitor concentration in the region if their enzyme-inhibitor dissociation constants were used for calculation.

Substrate consumption was within 5% of the initial concentration and data outside this range were discarded. The Michaelis constants (Km) for the enzyme-substrate complexes is 70 mM or greater (C. G. Knight et al., reference above), so that the factor (1+S/Km) can be approximated to unity without appreciable error.

For example, the following results were obtained for some of the compounds described in Examples below:
Compound of Example 3: MMP-1, $K_i$=2.3 nM; MMP-2, $K_i$=9.2 nM; MMP-3, $K_i$=150 nM.
Compound of Example 5: MMP-1, $K_i$=2.7 nM; MMP-2, $K_i$=0.62 nM; MMP-3, $K_i$=15.0 nM.
Compound of Example 6: MMP-1, $K_i$=67 nM; MMP-2, $K_i$=23 nM; MMP-3, $K_i$=430 nM.
Compound of Example 7: MMP-1, $K_i$=1.5 nM; MMP-2, $K_i$=3.1 nM; MMP-3, $K_i$=32 nM.
Compound of Example 8: MMP-1, $K_i$=45 nM; MMP-2, $K_i$=40 nM; MMP-3, $K_i$=1100 nM.
Compound of Example 9: MMP-1, $K_i$=2.2 nM; MMP-2, $K_i$=1.7 nM; MMP-3, $K_i$=110 nM.
Compound of Example 11: MMP-1, $K_i$=7.3 nM; MMP-2, $K_i$=4.7 nM; MMP-3, $K_i$=4.9 nM.
Compound of Example 12: MMP-1, $K_i$=6.8 nM; MMP-2, $K_i$=9.5 nM; MMP-3, $K_i$=10.0 nM.
Compound of Example 13: MMP-1, $K_i$=3.4 nM; MMP-2, $K_i$=6.5 nM; MMP-3, $K_i$=71 nM.
Compound of Example 16: MMP-1, $K_i$=1.5 nM; MMP-2, $K_i$=3.2 nM; MMP-3, $K_i$=23 nM.
Compound of Example 20: MMP-1, $K_i$=25 nM; MMP-2, $K_i$=19 nM; MMP-3, $K_i$=880 nM.

Some of the compounds of formula (I) were also shown to possess high activity at inhibiting the release of TNF from several different cell lines, under different stimulation conditions. For example, the following cell-based assay was used to assess such activity:

Cellular Assay (Protocol B)

The in vitro potency of the compounds of the present invention as inhibitors of the release of TNF from cells was determined as described below. THP-1 cells, cultured in RPMI 1640 supplemented with 10% FCS, were distributed into 24-well plates, 1 mL of a suspension of 1×10$^6$ cells/mL in each well. Compounds to be tested, dissolved in DMSO and diluted with the culture medium (1% final DMSO concentration) were added. Plates were incubated for 30 min at 37° C. in 5% CO$_2$, and lipopolisaccharide (LPS 0111:B4, 5 microg/mL) was added as a stimulant. After a further 4 h incubation, cells were harvested, centrifuged (2,000 rpm, 7 min), and the surnatant was collected and freezed (−20° C.) until analysis. Analysis was run by classical ELISA methodology (monoclonal anti-TNF-a antibody, rabbit capture policlonal antibody, and peroxidated anti-rabbit antibody). For example, the following results were obtained for some of the compounds described in Examples below:
Compound of Example 2: IC$_{50}$=5.2 mM
Compound of Example 3: IC$_{50}$=8.1 mM
Compound of Example 5: IC$_{50}$=1.49 mM
Compound of Example 6: IC$_{50}$=65.4 mM
Compound of Example 7: 90% inhibition at 100 microM.

Further, several compounds of formula (I), in particular when R$_2$ is hydroxy, and when R$_1$ is hydroxymethyl, have enhanced water solubility as compared to the vast majority of MMP inhibitors of the prior art. An aqueous solubility threshold, which may vary widely but can be roughly set in the range of 1–10 mg/mL, makes systemic administration easy, and more than often is essential to good oral bioavailability. For example, aqueous solubility (at pH 7.0, 25° C. ) of some of the preferred compound were as follows:
Compound of Example 3: >15 mg/mL
Compound of Example 7: 6 mg/mL
Compound of Example 8: 10 mg/mL
Compound of Example 9: >9 mg/mL
Compound of Example 11: 3.4 mg/mL
Compound of Example 12: >10 mg/mL
Compound of Example 13: 1.3 mg/mL
Compound of Example 20: 5.8 mg/mL
Compound of Example 22: 1.9 mg/mL
Compound of Example 23: 5 mg/mL
Compound of Example 24: >6 mg/mL
Compound of Example 25: >8 mg/mL The enhanced metabolic stability of the compounds of the present invention, observed in vitro toward hepatocyte suspensions, is reflected in superior pharmacokinetic properties, as determined by observation of plasma levels achievable after i.v. and oral administration to rats of compounds of formula (I) wherein W is —NHOH (Protocol C).

Pharmacokinetic Assay (Protocol C)

Male rats (Sprague-Dawley; body weight about 250–300 g) were acclimatized for about one week before the start of the study. Approximately one week before dosing and while under anasthesia, rats were fitted with a cannula implanted in the superior vena cava via the jugular vein. Before treatment, rats were overnight fasted. For each compound to be assessed, three rats were treated intravenously (injection in the tail vein as a bolus) with a single dose of 15 mg/kg (as free base or free acid if needed) body weight. Other three rats were treated orally (single bolus dose by gastric gavage) with 15 mg/kg of the same compound. In same cases, according to the detection limit of each particular compound, and its availability in stock, these standard doses were modified as needed.

Blood samples were collected into syringes especially prepared for use with the cannulated animals via the SCV cannula. Under standard conditions, blood samples (0.2 mL) were transferred into heparinized tubes at the following times: 0 (pre-dose), 2, 4, 8, 16, 30, 45, 60, 90 min, 2, 4, 6, 8 and 24 h after iv administration; 0 (pre-dose), 5, 10, 30, 45, 60, 90 min, 2, 4, 6, 8, and 24 h after oral administration. Plasma was obtained immediately by centrifugation (about 10,000 rpm for 3 min) and stored at −80° C. till analysis. Plasma samples were assayed for parent drug concentrations using an appropriate analytical method. Under standard conditions, liquid chromatography—tandem mass spectrometry (LC/MS-MS) was used.

Non-compartmental pharmacokinetic calculations were performed with the aid of Pharm-NCA package (SIMED, France). Maximum plasma concentration, $C_{max}$, and the corresponding time, $t_{max}$, were read as the coordinates of the highest raw-data point for individual plasma profiles. Terminal phase was evaluated by graphic judgement by eye; terminal rate constant, was calculated as the slope of the terminal linear portion of natural log-transformed plasma concentrations vs. time curve, obtained using linear regression. Terminal half-life, $t_{1/2},z$, was calculated as $\ln(2)/l_z$. The area under the plasma concentration-time curve was estimated by the linear trapezoidal rule up to the last measured concentration (AUC(0–$t_z$)) and extrapolated to infinity assuming monoexponential decay, using the formula AUC=AUC(0–$t_z$)+C($t_z$)/$l_z$, where C($t_z$) is the measured concentration of the last point with detectable concentration. Following iv dosing, systemic clearance was obtained using the formula Cl=Dose/AUC. According to Protocol C, the pharmacokinetic in rats of some representative compounds within the present invention was evaluated. Significant pharmacokinetic data obtained in rats at a 15 mg/kg dose were as follows:

Compound of Example 3: Clearance, 9.89 mL/min/kg; AUC iv, 1.53 mg×min/mL; $t_{1/2}$,z, 5.4 hr; AUC os, 66 μg×min/mL.

Compound of Example 16: Clearance, 11 mL/min/kg; AUC iv, 1.35 mg×min/mL; $t_{1/2}$, z, 2.3 hr; AUC os, 80 μg×min/mL.

In particular, the plasma clearance of the compounds of Example 3 and Example 16 is inferior to that reported for any hydroxamic acid MMP inhibitor disclosed in the literature, to our best knowledge.

The novel compounds of formula (I) can be used in a method of treatment of the human or animal body by therapy. The condition of a human or animal patient may thus be improved. In particular, compounds of the present invention can be used to limit the local growth of established tumors, and to limit growth of secondary metastases. The following protocol was used to evaluate the antitumoral efficacy in vivo of the compounds of the present invention:

Antitumor Efficacy Assay (Protocol D):

Human DU145 Prostatic Carcinoma cells (2×10$^6$) were injected subcutaneously at day 0 in Balb nu/nu mice. Treatment with inhibitor (i.p. injection) started at day +1 and terminated at day +20. Animal were sacrificed at day +21, and the tumors exised and weighted. Percent tumor growth inhibition vs. control mice (% TGI) was calculated as follows:

%  *TGI*=100−(Mean Tumor Weight in treated group)/(Mean Tumor Weight in control group)×100

For example, the TGI determined after 100 mg/kg b.i.d. treatment with the compound of Example 16, was 83% (p<0.01, Dunnett method).

The compounds of the present invention are typically administered in the form of pharmaceutical preparations which contain them in association with a compatible pharmaceutical carrier material. Thus, a distinct aspect of the present invention is the preparation of pharmaceutical compositions carrying a compound of formula (I) as active ingredient, and a method of management (i.e. treatment or prophylaxis) of diseases or conditions mediated in humans and warm blood animals by MMPs, which method comprises administering to the mammal an effective amount of a compound of formula (I) above, or a pharmaceutically acceptable salt thereof.

The present invention therefore further provides a compound of the invention as defined above for use in a method of treatment or prophylaxis of a disease mediated in a mammal by a matrix metalloproteinase, and in a method of treatment or prophylaxis of an inflammatory, infectious or immunological disease prompted by the release of TNF.

In particular, the compounds of formula (I) can be administered:

A) Orally, for example, as tablets, coated tablets, dragees, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatin or acacia, and lubricating agents, for example magnesium stearate, stearic acid or talc. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyoxyethylene sorbitan monooleate. The said aqueous suspensions may also contain one or more preservatives, for example, ethyl or n-propyl p-hydroxybenzoate, one or more coloring agents, one or more flavoring agents, or one or more sweetening agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents, such as those set forth above, and flavouring agents may be added to provide a palatable oral preparation. These compositions may be preserved by the addition of an antioxidant such as ascorbic acid.

Dispersible powders and granules suitable for peparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan mono-oleate, and condensation products of the said partial esters with ethylene oxide, for example polyoxyethylene sorbitan monooleate. The emulsion may also contain sweetening and flavoring agents. Syrups and elixirs may be formulated with sweetening agents, for example glycerol, sorbitol or sucrose. Such formulations may also contain a demulcent, a preservative and flavoring and coloring agents;

B) Parenterally, either subcutaneously, or intravenously, or intramuscularly, or intrasternally, or by infusion techniques, in the form of sterile injectable aqueous or olagenous suspensions. This suspension may be formulated according to the known art using those suitable dispersing of wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irratating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspensions.

Daily dosages can vary within wide limits and will be adjusted to the individual requirements in each particular case. In general, for administration to adults, an appropriate daily dosage is in the range of about 5 mg to about 500 mg, although the upper limit may be exceeded if expedient. The daily dosage can be administered as a single dosage or in divided dosages.

The following Examples are meant to illustrate the present invention in more detail.

EXAMPLE 1

[(2R,3S)-3,4-Dihydroxy-2-isobutyl-3-(tetrahydropyran-2-yloxymethyl)succinyl]-L-tert-leucine-N-methylamide

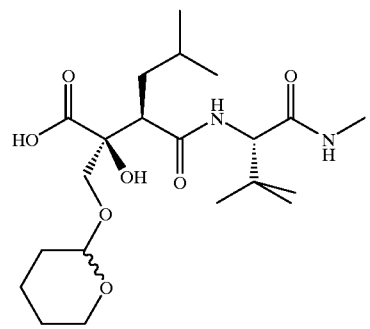

Step 1: [(2R)-4-Benzyloxy-3-benzyloxycarbonyl-2-isobutyl-succinyl]-L-tert-leucine-N-methylamide Benzyl (3R)-(2-benzyloxycarbonyl-3-carboxy-5-methyl) hexanoate (6.0 g, 15 mmol), obtained as described in Preparation 1, was dissolved in DMF (12 mL). To this solution, L-tert-leucine-N-methylamide (2.15 g, 15 mmol) and HOBT (1-hydroxybenzotriazole hydrate; 2.03 g, 15 mmol) were added at room temperature, followed by dropwise addition at 0C of a solution of DCC (dicyclohexylcarbodiimide; 7.85 g, 15 mmol) in THF (12 mL). The mixture was kept at 0° C. for 30 min, then kept under stirring for 5 h at room temperature. Dicyclohexylurea was filtered off, the solvent was removed in vacuo, the residue was taken up in ethyl acetate, and the solution was sequentially washed with 10% aqueous citric acid (100 mL), saturated aqueous sodium bicarbonate (100 mL), and brine (100 mL). After drying over $Na_2SO_4$, the solvent was removed to give an oil. Purification by flash chromatography over silica (n-hexane and ethyl acetate gradient elution) afforded the title compound as a white foam (6.6 g, 13 mmol; 86.6%). $^1$H NMR (200 MHz, DMSO-$d_6$): 0.66 and 0.71 (each d, J=6.4 Hz, 6H, 2×Me), 0.82 (s, 9H, t-Bu), 0.9–1.4 (m, 3H, C$\underline{H}_2$C$\underline{H}$Me$_2$), 2.49 (d, J=4.6 Hz, 3H, CONHC$\underline{H}_3$), 3.15 (m, 1H, C$\underline{H}$-iBu), 3.65 (d, J=9.9 Hz, 1H, C$\underline{H}$(CO$_2$Bn)$_2$), 4.09 (d, J=9.4 Hz, 1H, CONHC$\underline{H}$), 5.02 (m, 4H, 2×CO$_2$C$\underline{H}_2$Ph), 7.28 (m, 10H, 2×Ph), 7.76 (q, J=4.6 Hz, 1H, CON$\underline{H}$CH$_3$), and 7.82 ppm (d, J=9.4 Hz, 1H, CON$\underline{H}$CH).

Step 2: [(2R)-4-Hydroxy-2-isobutyl-3-methylenesuccinyl]-L-tert-leucine-N-methylamide A solution of the compound from Step 1 above (6.6 g, 13 mmol) in ethanol (100 mL) was treated with 10% Pd on charcoal (0.6 g) and exposed to a hydrogen atmosphere for 3 h. The catalyst was removed by filtration (Celite$^R$ filter aid), washed with additional ethanol (50 mL), and the resulting solution of crude (2R)-(4-hydroxy-3-hydroxycarbonyl-2-isobutylsuccinyl)-L-tert-leucine-N-methylamide was treated with piperidine (1.5 mL, 15 mmol) and 37% aqueous formaldehyde (10.1 mL, 0.136 mol). After 20 h at room temperature, the mixture was evaporated under reduced pressure and the residue partitioned between ethyl acetate and 4% aqueous HCl. The organic layer was sequentially washed with brine and water, then dried over $Na_2SO_4$ and evaporated, to afford the title compound as a white solid (3.16 g, 10 mmol; 80.3%). $^1$H NMR (400 MHz, DMSO-$d_6$): 0.75 and 0.80 (each d, J=6.4 Hz, 6H, 2×Me), 0.78 (s, 9H, t-Bu), 1.3–1.6 (m, 3H, CH$_2$CHMe$_2$), 2.51 (d, J=4.7 Hz, 3H, CONHCH$_3$), 3.54 (m, 1H, CH-iBu), 4.10 (d, J=9.4 Hz, 1H, CONHCH), 5.65 and 6.10 (each s, 2H, C=CH$_2$), 7.36 (d, J=9.4 Hz, 1H, CONHCH), 7.87 (q, J=9.4 Hz, 1H, CONHCH$_3$), and 12.7 ppm (broad s, 1H, CO$_2$H).

Step 3: [(2R, 3S)-4-Benzhydryloxy-3-hydroxy-3-hydroxymethyl-2-isobutylsuccinyl]-L-text-leucine-N-methylamide A solution of the compound from Step 2 above (3.16 g, 10 mmol) in tert-butanol (35 mL) was added to a mixture of N-methylmorpholine-N-oxide (60% in water; 3.32 g, 17 mmol), osmium tetroxide (2.5% in tert-butanol; 0.813 mL, 0.08 mmol), acetone (1 mL) and water (2 mL). After stirring for 20 h at room temperature, the solution was evaporated to dryness to leave crude (3S,2R)-(3,4-dihyroxy-3-hydroxymethyl-2-isobutyl-succinyl)-L-tert-leucine-N-methylamide as a light tan foam. This material was dissolved in acetonitrile, and diphenyl diazomethane (DDM; 1.95 g, 10 mmol) was added portionwise. After 2 h at room temperature, glacial acetic acid was added dropwise until the colour of excess DDM was discharged. Removal of the solvent and flash chromatography over silica (n-hexane and ethyl acetate gradient elution) afforded the title compound as the major pure diastereoisomer (2.7 g, 5.3 mmol; 52.7%) as a white solid. $^1$H NMR (400 MHz, DMSO-$d_6$): 0.54 and 0.61 (each d, J=6.4 Hz, 6H, 2×Me), 0.60 and 1.61 (each m, 2H, CH$_2$CHMe$_2$), 0.88 (s, 9H, t-Bu), 1.22 (m, 1H, CHMe$_2$), 2.54 (d, J=4.7 Hz, 3H, CONHCH$_3$), 2.88 (dd, J=3.5 and 12.0 Hz, 1H, CH-iBu), 3.42 and 3.78 (each m, 2H, CH$_2$OH), 4.13 (d, J=9.1 Hz, 1H, CONHCH), 4.93 (dd, J=4.4 and 7.3 Hz, 1H, CH$_2$OH), 5.41 (s, 1H, tertiary OH), 6.83 (s, 1H, CHPh$_2$), 7.2–7.4 (m, 10H, 2×Ph), 7.86 (d, J=9.1 Hz, 1H, CONHCH), and 7.94 ppm (q, J=4.7 Hz, 1H, CONHCH$_3$).

Step 4: [(2R,3S)-4-Benzhydryloxy-3-hydroxy-2-isobutyl-3-(tetrahydropyran-2-yloxymethyl)succinyl]-L-tert-leucine-N-methylamide A solution of the compound from Step 3 above (2.7 g, 5.3 mmol) in dichloromethane (50 mL) was treated at 0° C. with pyridinium-p-toluenesulfonate (150 mg) and 3,4-dihydro-2H-pyran (4.8 mL, 5.3 mmol). The mixture was kept in a cold room (4° C.) for 3 days, then diluted with ethyl acetate (150 mL) and sequentially washed with 4% aqueous HCl, saturated aqueous sodium bicarbonate, and water. After drying over $Na_2SO_4$ and evaporation, a colourless oil was obtained, which was treated with petroleum ether (150 mL) and kept at 4° C. overnight. A white precipitate formed, which was recovered by filtration, thereby obtaining the title compound (2.1 g, 3.5 mmol; 66%) as a diatereoisomeric mixture at the 2-tetrahydropyran carbon atom. $^1$H NMR (400 MHz, DMSO-$d_6$): 0.59 and 0.65 (each d, J=6.7 Hz, 6H, 2×Me), 0.7–1.7 (m, 9H, CH$_2$CHMe$_2$ and pyran 3,4,5-methylene), 0.87 (s, 9H, t-Bu), 2.53 (d, J=4.4 Hz, 3H, CONHCH$_3$), 2.90 (m, 1H, CH-iBu), 3.1–3.7 (m, 2H, pyran 6-methylene), 3.30 and 3.98 (each d, J=10.2 Hz, CH$_2$O-pyran of pyran isomer A), 3.60 and 3.98 (each d, J=10.0 Hz, CH$_2$O-pyran of pyran isomer B), 4.13 and 4.15 (each d, J=9.4 Hz, 1H, CONHCH of the two isomers at pyran), 4.26 and 4.47 (each m, 1 H, anomeric CH of two pyran isomers), 5.63 and 5.72 (each s, 1H, tertiary OH of the two isomers at pyran), 6.87 (s, 1H, CHPh$_2$), 7.2–7.4 (m, 10H, 2×Ph), 7.84 and 7.85 (each d, J=9.4 Hz, 1H, CONHCH of the two isomers at pyran), and 7.95 ppm (q, J=4.4 Hz, 1H, CONHCH$_3$).

Step 5: [(2R,3S)-3,4-Dihydroxy-2-isobutyl-3-(tetrahydropyran-2-yloxymethyl)-succinyl]-L-tert-leucine-N-methylamide The compound from Step 4 above (2.1 g, 3.5 mmol) was taken up in ethanol (50 mL) and exposed to a hydrogen atmosphere in the presence of 10% Pd on charcoal (0.2 g) overnight. The catalyst was removed by filtration (Celite$^R$ filter aid), washed with additional ethanol, and the combined ethanol solution was evaporated to dryness. The residue was taken up with n-hexane, stirred for 30 min, and the resulting white powder was collected by filtration, thereby obtaining the title compound (diastereomeric mixture at the anomeric tetrahydropyran carbon atom; 1.39 g, 3.2 mmol; 92%). $^1$H NMR (400 MHz, DMSO-$d_6$): 0.80 (d, J=6.5 Hz, 6H, 2×Me), 0.87 (s, 9H, t-Bu), 0.9–1.7 (m, 9H, CH$_2$CHMe$_2$ and pyran 3,4,5-methylene), 2.53 (d, J=4.7 Hz, 3H, CONHCH$_3$), 2.71 (m, 1H, CH-iBu), 3.21 and 3.80 (each d, J=10 Hz, CH$_2$O-pyran of pyran isomer A), 3.52 (m, CH$_2$O-pyran of pyran isomer B), 3.30 and 3.70 (each m, 2H, pyran 6-methylene), 4.10 and 4.11 (each d, J=9.4 Hz, 1H, CONHCH of the two isomers at pyran), 4.45 and 4.49 (each m, 1H, anomeric CH of two pyran isomers), 5.40 (broad s, 1H, tertiary OH), 7.66 and 7.67 (each d, J=9.4 Hz, 1H, CONHCH of the two isomers at pyran), and 7.90 ppm (q, J=4.7 Hz, 1H, CONHCH$_3$).

EXAMPLE 2

[(2R,3S)-3-Hydroxy-4-hydroxyamino-2-isobutyl-3-(tetrahydro-pyran-2-yloxymethyl)succinyl]-L-tert-leucine-N-methylamide

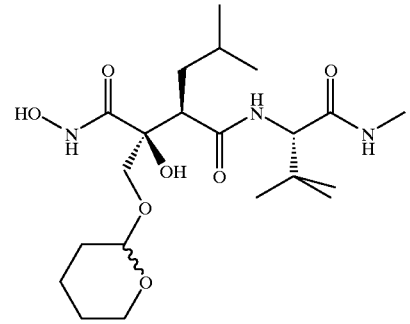

Step 1: [(2R,3S)-4-Benzyloxyamino-3-hydroxy-2-isobutyl-3-(tetrahydropyran-2-yloxymethyl)succinyl]-L-tert-leucine-N-methylamide The compound described in Example 1 above (1.39 g, 3.2 mmol) was dissolved in acetonitrile (50 mL). To this solution, O-benzylhydroxylamine hydrochloride (0.59 g, 3.63 mmol), N-methylmorpholine (0.8 mL, 7.35 mmol), and 0-benzotriazol-yl-N,N,N',N'-tetramethyluronium tetrafluoroborate (TBTU; 1.29 g, 4.01 mmol) were added in this order. After stirring for 20 h at room temperature, the solvent was removed under reduced pressure and the residue was taken up in ethyl acetate. Sequential washing with 2N aqueous HCl, saturated aqueous sodium bicarbonate and water, followed by drying over $Na_2SO_4$ and evaporation, left a residue which was purified by flash chromatography over silica (n-hexane and ethyl acetate gradient elution), thereby affording the two isomers (at the pyran anomeric C) of the title product as white solids (sum of the two 740 mg, 1.38 mmol; 42%). Isomer A, $^1$H NMR (400 MHz, DMSO-$d_6$): 0.73 and 0.76 (each d, J=6.7 Hz, 6H, 2×Me), 0.89 (s, 9H, t-Bu), 0.9–1.6 (m, 9H, CH$_2$CHMe$_2$ and pyran 3,4,5-methylene), 2.53 (d, J=4.7 Hz, 3H, CONHCH$_3$), 2.89 (m, 1H, CH-iBu), 3.11 and 3.91 (each d, J=10.3 Hz, 2H, C H₂O-pyran), 3.30 and 3.65 (each m, 2H, pyran 6-methylene), 4.12 (d, J=9.1 Hz, 1H, CONHCH), 4.52 (m, 1H, anomeric CH of pyran), 4.78 (m, 2H, Ph—CH₂O), 5.33 (s, 1H, tertiary OH), 7.35 (m, 5 H, Ph), 7.84 (q, J=4.7 Hz, 1H, CONHCH₃), 8.06 (d, J=9.1 Hz, 1H, CONHCH), and 11.20 ppm (s, 1H, CONHO). Isomer B, ¹H NMR (400 MHz, DMSO-d₆): 1.17 and 1.20 (each d, J=6.7 Hz, 6H, 2×Me), 1.32 (s, 9H, t-Bu), 1.1–2.1 (m, 9H, CH₂CHMe₂ and pyran 3,4,5-methylene), 2.97 (d, J=4.7 Hz, 3H, CONHCH₃), 3.27 (dd, J=3.5 and 11.7 Hz, 1H, CH-iBu), 3.80 and 4.10 (each m, 2H, pyran 6-methylene), 3.87 and 4.12 (each d, J=10.2 Hz, 2H, CH₂O-pyran), 4.57 (d, J=9.1 Hz, 1H, CONHCH), 4.87 (m, 1H, anomeric CH of pyran), 5.20 (s, 2H, Ph—CH₂O), 5.79 (s, 1H, tertiary OH), 7.78 (m, 5H, Ph), 8.31 (q, J=4.7 Hz, 1H, CONHCH₃), 8.46 (d, J=9.1 Hz, 1H, CONHCH), and 11.43 ppm (s, 1H, CONHO).

Step 2: [(2R,3S)-3-Hydroxy-4-hydroxyamino-2-isobutyl-3-(tetrahydropyran-2-yloxymethyl)succinyl]-L-tert-leucine-N-methylamide A solution of the compound from Step 1 above (combined mixture of isomers A and B; 740 mg, 1.38 mmol) in ethanol (40 mL) was exposed to a hydrogen atmosphere in the presence of 10% Pd on charcoal (74 mg) for 2 h. The catalyst was removed by filtration (Celite^R filter aid), washed with additional ethanol, and the combined ethanol solution was evaporated to dryness. The residue was taken up with n-hexane, stirred for 30 min, and the resulting white powder was collected by filtration, thereby obtaining the title compound (diasteromeric mixture at the 2-tetrahydropyran carbon atom; 565 mg, 1.27 mmol; 92%). 1H NMR (400 MHz, DMSO-d₆): 0.78 (m, 6 H, 2×Me), 0.89 (s, 9H, t-Bu), 0.9–1.8 (m, 9H, CH₂CHMe₂ and pyran 3,4,5-methylene), 2.54 (d, J=4.7 Hz, 3H, CONHCH₃), 2.80 and 2.86 (each dd, J=3.5 and 11.7 Hz, 1H, CH-iBu of two pyran isomers), 3.12 and 3.89 (each d, J=10.2 Hz, CH₂O-pyran of pyran isomer A), 3.41 and 3.68 (each d, J=10.2 Hz, CH₂O-pyran of pyran isomer B), 3.30–3.60 (two m, 2H, pyran 6-methylene), 4.12 (d, J=9.1 Hz, 1H, CONHCH), 4.41 and 4.50 (each m, 1H, anomeric CH of two pyran isomers), 5.23 and 5.29 (each s, 1H, tertiary OH of two pyran isomers), 7.85 and 7.88 (each q, J=4.7 Hz, 1H, CONHCH₃ of two pyran isomers), 7.94 and 7.99 (each d, J=9.1 Hz, 1H, CONHCH of two pyran isomers), 8.72 and 8.72–8.73 (each s, 1H, NHOH of two pyran isomers), and 10.27 and 10.39 ppm (each s, 1H, NHOH of two pyran isomers).

By the same procedure, applied to each separate isomer (A and B) of the compound of Step 1 above, the separate isomers (A and B) of the title compound were obtained.

EXAMPLE 3
[(2R,3S)-3-Hydroxy-4-hydroxyamino-3-hydroxymethyl-2-isobutyl)-succinyl]-L-tert-leucine-N-methylamide

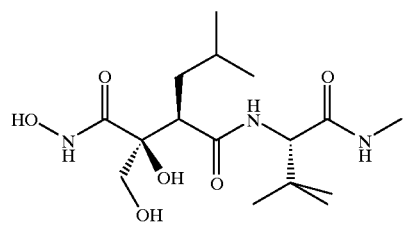

The compound described in Example 2 above (570 mg, 1.28 mmol) was dissolved in 80% aqueous ethanol (40 mL), and pyridinium p-toluenesulfonate (306 mg, 1.22 mmol) was added. The solution was heated to 50° C. for 3 h, the solvent was removed under reduced pressure and the residue was purified by reverse phase chromatography over silica (water and ethanol gradient elution) to afford the title product as a white solid (372 mg, 1.03 mmol; 85%). ¹H NMR (400 MHz, DMSO-d₆): 0.76 and 0.78 (each d, J=6.4 Hz, 6H, 2×Me), 0.89 (s, 9H, t-Bu), 0.97 and 1.62 (each m, 2H, CH₂CHMe₂), 1.30 (m, 1H, CH₂CHMe₂), 2.53 (d, J=4.4 Hz, 3H, CONHCH₃), 2.81 (dd, J=3.2 and 11.7 Hz, 1H, CH-iBu), 3.12 and 3.62 (each m, 2H, CH₂OH), 4.11 (d, J=9.4 Hz, 1H, CONHCH), 4.65 (dd, J=4.7 and 7.3 Hz, 1H, CH₂OH), 5.12 (s, 1H, tertiary OH), 7.87 (m, 2H, CONHCH₃ and CONHCH), 8.70 (s, 1H, NHOH), and 10.21 ppm (s, 1H, NHOH).

EXAMPLE 4
[(2R,3S)-3,4-Dihydroxy-2-isobutyl-3-(tetrahydropyran-2-yloxymethyl)-succinyl]-L-phenylalanine-N-methylamide

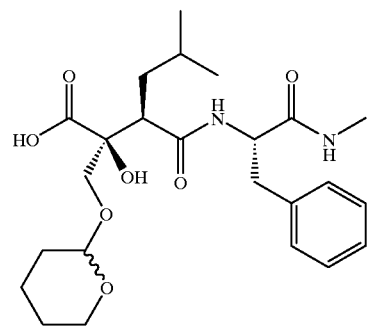

Step 1: [(2R)-4-Benzyloxy-3-benzyloxycarbonyl-2-isobutyl-succinyl]-L-phenylalanine-N-methylamide Benzyl (3R)-(2-benzyloxycarbonyl-3-carboxy-5-methyl)hexanoate (33.5 g, 84 mmol), obtained as described in Preparation 1, was dissolved in DMF (100 mL). To this solution, L-phenylalanine-N-methylamide hydrochloride (21.1 g, 84 mmol), HOBT (1-hydroxybenzotriazole hydrate; 11 g, 81 mmol) and triethylamine (11.7 mL, 84 mmol) were added at room temperature, followed by dropwise addition at 0° C. of a solution of DCC (dicyclohexylcarbodiimide; 17.33 g, 84 mmol) in THF (100 mL). The mixture was kept at 0° C. for 30 min, then kept under stirring for 5 h at room temperature. Dicyclohexylurea was filtered off, the solvent was removed in vacuo, the residue was taken up in ethyl acetate, and the solution was sequentially washed with 10% aqueous citric acid (800 mL), saturated aqueous sodium bicarbonate (800 mL), and brine (800 mL). After drying over Na₂SO₄, the solvent was removed to give an oil, which was taken up in diisopropyl ether (200 mL). After stirring for 20 h, the title compound was collected by filtration as a white solid (38.0 g, 68 mmol; 81%). ¹H NMR (400 MHz, CDCl₃): 0.74 and 0.75 (each d, J=6.4 Hz, 6H, 2×Me), 1.01 and 1.53 (each m, 2H, CH₂CHMe₂), 1.32 (m, 1H, CHMe₂), 2.65 (d, J=4.7 Hz, 3H, CONHCH₃), 2.92 (m, 1H, CH-iBu), 2.99 (m, 2H, Phe methylene), 3.79 (d, J=9.1 Hz, 1H, CH(CO₂Bn)₂), 4.48 (m, 1H, CONHCH), 5.10 (m, 4H, 2×CO₂CH2Ph), 5.70 (m, 1H, CONHCH₃), 6.56 (d, J=7.6 Hz, 1H, CONHCH), and 7.2–7.4 ppm (m, 15H, 3×Ph).

Step 2: [(2R)-4-Hydroxy-2-isobutyl-3-methylenesuccinyl]-L-phenylalanine-N-methylamide A solution of the compound from Step 1 above (8.7 g, 14.6 mmol) in ethanol (100 mL) was treated with 10% Pd on charcoal (0.8 g) and exposed to a hydrogen atmosphere for 3 h. The catalyst was removed by filtration (Celite^R filter aid), washed with additional ethanol (50 mL), and the resulting solution of crude (2R)-(4-hydroxy-3-hydroxycarbonyl-2-isobutylsuccinyl)-L-phenylalanine-N-methylamide was treated with piperidine (1.7 mL, 17.5 mmol) and 37% aqueous formaldehyde (11.7 mL, 156 mmol). After 20 h at room temperature, the mixture was evaporated under reduced pressure and the residue partitioned between ethyl acetate and 4% aqueous HCl. The organic layer was sequentially washed with brine and water, then dried over $Na_2SO_4$ and evaporated, to leave a residue which was treated with diisopropyl ether (50 mL). Filtration afforded the title compound as a white solid (4.7 g, 12.4 mmol; 85%). $^1$H NMR (200 MHz, DMSO-$d_6$): 0.80 (d, J=6.7 Hz, 6H, 2×Me), 1.2–1.8 (m, 3H, C$\underline{H}_2$C$\underline{H}$Me$_2$), 2.55 (d, J=4.5 Hz, 3H, CONHC$\underline{H}_3$), 2.83 (m, 2H, Phe methylene), 3.45 (dd, J=5.8 and 8.4 Hz, 1H, C$\underline{H}$-iBu), 4.41 (m, 1H, CONHC$\underline{H}$), 5.44 and 5.98 (each m, 2H, C=C$\underline{H}_2$), 7.20 (m, 5H, Ph), 7.76 (q, J=4.5 Hz, 1H, CON$\underline{H}$CH$_3$), and 7.85 ppm (d, J=8.4 Hz, 1H, CON$\underline{H}$CH).

Step 3: [(2R,3S)-4-Benzhydryloxy-3-hydroxy-3-hydroxymethyl-2-isobutylsuccinyl]-L-phenylalanine-N-methylamide, and [(2R,3R)-4-Benzhydryloxy-3-hydroxy-3-hydroxymethyl-2-isobutylsuccinyl]-L-phenylalanine-N-methylamide A solution of the compound from Step 2 above (2.0 g, 5.77 mmol) in tert-butanol (20 mL) was added to a mixture of N-methylmorpholine-N-oxide (60% in water; 1.96 g, 9.8 mmol), osmium tetroxide (2.5% in tert-butanol; 0.521 mL, 0.05 mmol), acetone (1 mL) and water (2 mL). After stirring for 20 h at room temperature, the solution was evaporated to dryness to leave crude (3,4-dihyroxy-3-hydroxymethyl-2-isobutyl-succinyl)-L-phenylalanine-N-methylamide as a light tan foam. This material was dissolved in acetonitrile, and diphenyl diazomethane (DDM; 1.12 g, 5.77 mmol) was added portionwise. After 2 h at room temperature, glacial acetic acid was added dropwise until the colour of excess DDM was discharged. Removal of the solvent left a residue, which was collected as a white solid after trituration with diisopropyl ether, filtration, and washing with ethyl ether, thereby obtaining the title product, (2R,3S) isomer (1.75 g, 3 mmol; 52.8%). $^1$H NMR (400 MHz, DMSO-$d_6$): 0.45 and 0.51 (each d, J=6.7 Hz, 6H, 2×Me), 0.44 and 1.56 (each m, 2H C$\underline{H}_2$CHMe$_2$), 0.98 (m, 1H, C$\underline{H}$Me$_2$), 2.54 (d, J=4.4 Hz, 3H, CONHC$\underline{H}_3$), 2.67 (dd, J=3.2 and 12.3 Hz, 1H, C$\underline{H}$-iBu), 2.77 and 2.95 (each m, 2H, Phe -methylene), 3.23 and 3.64 (each m, 2H, C$\underline{H}_2$OH), 4.46 (m, 1H, CONHC$\underline{H}$), 4.82 (dd, J=4.4 and 7.8 Hz, 1H, CH$_2$O$\underline{H}$), 5.32 (s, 1H, tertiary OH), 6.81 (s, 1H, C$\underline{H}$Ph$_2$), 7.0–7.4 (m, 15H, 3×Ph), 7.87 (q, J=4.4 Hz, 1H, CON$\underline{H}$CH$_3$), and 7.96 ppm (d, J=8.5 Hz, 1H, CON$\underline{H}$CH).

The mother liquors were evaporated, and the residue purified by flash chromatography over silica (n-hexane and ethyl acetate gradient elution) to afford the title product, (2R,3R) isomer (495 mg, 0.86 mmol; 14.9%). $^1$H NMR (400 MHz, DMSO-$d_6$): 0.60 and 0.64 (each d, J=6.0 Hz, 6H, 2×Me), 1.0–1.5 (m, 3 H, C$\underline{H}_2$C$\underline{H}$Me$_2$), 2.43 (d, J=4.7 Hz, 3H, CONHC$\underline{H}_3$), 2.64 (m, 1H, C$\underline{H}$-iBu), 2.75 and 2.92 (each m, 2H, Phe methylene), 3.55 (m, 2H, C$\underline{H}_2$OH), 4.36 (m, 1H, CONHC$\underline{H}$), 4.82 (t, J=5.5 Hz, 1H, CH$_2$O$\underline{H}$), 5.53 (s, 1H, tertiary OH), 6.63 (s, 1H, C$\underline{H}$Ph$_2$), 7.0–7.4 (m, 15H, 3×Ph), 7.57 (q, J=4.7 Hz, 1H, CON$\underline{H}$CH$_3$), and 7.89 ppm (d, J=8.5 Hz, 1H, CON$\underline{H}$CH).

Step 4: [(2R,3S)-4-Benzhydryloxy-3-hydroxy-2-isobutyl-3-(tetrahydropyran-2-yloxymethyl)succinyl]-L-phenylalanine-N-methylamide A solution of the compound from Step 3 above ((2R,3S) isomer; 820 mg, 1.43 mmol) in dichloromethane (25 mL) was treated at 0° C. with pyridinium-p-toluenesulfonate (50 mg) and 3,4-dihydro-2H-pyran (1.3 mL, 14.3 mmol). The reaction was complete after stirring for 20 h at room temperature. The mixture was concentrated under reduced pressure, then taken up in ethyl acetate (100 mL) and sequentially washed with 2N aqueous HCl, saturated aqueous sodium bicarbonate, and water. After drying over $Na_2SO_4$ and evaporation, a solid was obtained, which was treated with petroleum ether (50 mL) and and stirred for 30 min. A white precipitate formed, which was recovered by filtration, thereby obtaining the title compound (0.7 g, 1.06 mmol; 74.3%) in the absolute (2R,3S) configuration and as a diastereomeric mixture at the anomeric tetrahydropyran carbon atom.

Step 5: [(2R,3S)-3,4-Dihydroxy-2-isobutyl-3-(tetrahydropyran-2-yloxymethyl)-succinyl]-L-phenylalanine-N-methylamide The compound from Step 4 above (700 mg, 1.06 mmol) was taken up in ethanol (25 mL) and exposed to a hydrogen atmosphere in the presence of 10% Pd on charcoal (70 mg) for 2 h. The catalyst was removed by filtration (Celite$^R$ filter aid), washed with additional ethanol, and the combined ethanol solution was evaporated to dryness. The residue was taken up with n-hexane, stirred for 30 min, and the resulting white powder was collected by filtration, thereby obtaining the title compound (diastereomeric mixture at the anomeric tetrahydropyran carbon atom; 470 mg, 1.0 mmol; 94.3%). $^1$H NMR _(400 MHz, DMSO-$d_6$): 0.65 (m, 6H, 2×Me), 0.8–1.8 (m, 9H, C$\underline{H}_2$C$\underline{H}$Me$_2$ and pyran 3,4,5-methylene), 2.50 (m, 1H, C$\underline{H}$-iBu), 2.53 (d, J=4.7 Hz, 3H, CONHC$\underline{H}_3$), 2.76 and 2.93 (each m, 2H, Phe methylene), 2.98 and 3.69 (each d, J=10.0 Hz, C$\underline{H}_2$O-pyran of pyran isomer A), 3.36 and 3.42 (each d, J=10.0 Hz, C$\underline{H}_2$O-pyran of pyran isomer B), 3.30 and 3.60 (each m, 2H, pyran 6-methylene), 4.34 and 4.40 (each m, 1H, anomeric CH of two pyran isomers), 4.43 (m, 1H, CONHC$\underline{H}$ of the two isomers at pyran), 5.83 (broad s, 1H, tertiary OH), 7.20 (m, 5H, Ph), 7.83 (m, 2H, CON$\underline{H}$CH and CON$\underline{H}$CH$_3$), and 12.0 ppm (broad s, 1H, COOH).

EXAMPLE 5

[(2R,3S)-3-Hydroxy-4-hydroxyamino-2-isobutyl-3-(tetrahydro-pyran-2-yloxymethyl)succinyl]-L-phenylalanine-N-methylamide

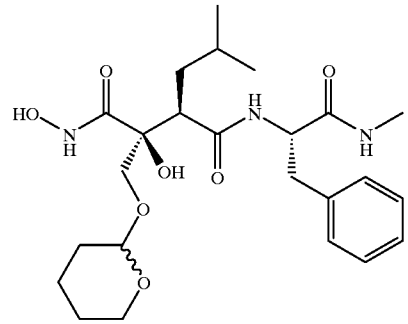

Step 1: [(2R,3S)-4-Benzyloxyamino-3-hydroxy-2-isobutyl-3-tetrahydropyran-2-yloxymethyl)succinyl]-L-phenylalanine-N-methylamide The compound described in Example 4 above (430 mg, 0.92 mmol) was dissolved in acetonitrile (20 mL). To this solution, O-benzylhydroxylamine hydrochloride (161 mg, 1.01 mmol), N-methylmorpholine (0.222 mL, 2.02 mmol), and 0-benzotriazol-yl-N,N,N',N'-tetramethyl-uronium tetrafluoroborate (TBTU; 354 mg, 1.1 mmol) were added in this order. After stirring for 20 h at room temperature, the solvent was removed under reduced pressure and the residue was taken up in ethyl acetate. Sequential washing with 2N aqueous HCl, saturated aqueous sodium bicarbonate and water, followed by drying over $Na_2SO_4$ and evaporation, left a residue which was purified by flash chromatography over silica (n-hexane and ethyl acetate gradient elution), thereby obtaining the title product (diastereomeric mixture at the pyran anomeric C) as a white solid.

Step 2: [(2R,3S)-3-Hydroxy-4-hydroxyamino-2-isobutyl-3-(tetrahydro-pyran-2-yloxymethyl)succinyl]-L-phenylalanine-N-methylamide A solution of the compound from Step 1 above (100 mg, 0.17 mmol) in ethanol (5 mL) was exposed to a hydrogen atmosphere in the presence of 10% Pd on charcoal (10 mg) for 2 h. The catalyst was removed by filtration (Celite$^R$ filter aid), washed with additional ethanol, and the combined ethanol solution was evaporated to dryness. The residue was taken up with n-hexane, stirred for 30 min, and the resulting white powder was collected by filtration, thereby obtaining the title compound (diastereomeric mixture at the anomeric tetrahydropyran carbon atom; 77 mg, 0.16 mmol; 94%). For analytical purpose, the two diastereoisomers were separated by reverse phase chromatography. ISOMER A, $^1$H NMR (400 MHz, DMSO-d$_6$): 0.73 and 0.74 (each d, J=7.0 Hz, 6H, 2×Me), 0.90 and 1.50 (each m, 2H, C$\underline{H}_2$CHMe$_2$), 1.20 (m, 1H, CH$_2$C$\underline{H}$Me$_2$), 1.2–1.7 (m, 6H, pyran 3,4,5 methylene), 2.55 (d, J=4.4 Hz, 3H, CONHC$\underline{H}_3$), 2.60 (m, 1H, C$\underline{H}$-iBu), 2.80 and 2.95 (each m, 2H, Phe methylene), 3.20 and 3.53 (each d, J=10.6 Hz, C$\underline{H}_2$O-pyran), 3.35 and 3.72 (two m, 2 H, pyran 6-methylene), 4.34 (m, 1H, anomeric pyran CH), 4.50 (m, 1H, CONHC$\underline{H}$), 5.06 (broad s, 1H, tertiary OH), 7.1–7.3 (m, 5H, Ph), 7.74 (broad s, 1H, CON$\underline{H}$CH$_3$), 8.05 (broad s, 1H, CON$\underline{H}$CH), 8.60 (broad s, 1H, CONHO$\underline{H}$), and 10.10 ppm (broad s, 1H, CON$\underline{H}$OH). ISOMER B, $^1$H NMR (400 MHz, DMSO-d$_6$): 0.72 and 0.74 (each d, J=6.7 Hz, 6H, 2×Me), 0.80 and 1.50 (each m, 2H, C$\underline{H}_2$CHMe$_2$), 1.20 (m, 1H, CH$_2$C$\underline{H}$Me$_2$), 1.3–1.7 (m, 6H, pyran 3,4,5 methylene), 2.55 (d, J=4.4 Hz, 3H, CONHC$\underline{H}_3$), 2.60 (m, 1H, C$\underline{H}$-iBu), 2.80 and 2.92 (each m, 2H, Phe methylene), 2.67 and 3.67 (each d, J=10.0 Hz, C$\underline{H}_2$O-pyran), 3.30 and 3.70 (two m, 2H, pyran 6-methylene), 4.35 (m, 1H, anomeric pyran CH), 4.49 (m, 1H, CONHC$\underline{H}$), 5.09 (broad s, 1H, tertiary OH), 7.1–7.3 (m, 5H, Ph), 7.88 (q, J=4.4 Hz, 1H, CON$\underline{H}$CH$_3$), 8.31 (d, J=8.0 Hz, 1H, CON$\underline{H}$CH), 8.65 (broad s, 1H, CONHO$\underline{H}$), and 10.22 ppm (broad s, 1H, CON$\underline{H}$OH).

EXAMPLE 6

[(2R,3R)-3-Hydroxy-4-hydroxyamino-2-isobutyl-3-(tetrahydro-pyran-2-yloxymethyl)succinyl]-L-phenylalanine-N-methylamide

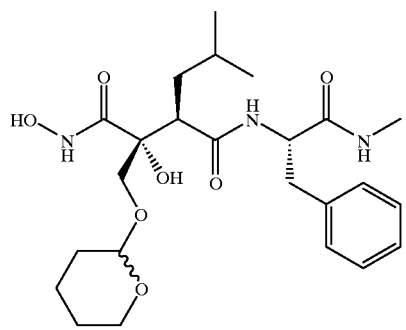

Starting from the (2R,3R) isomer of the compound described in Example 4 above, Step 3, and by identical procedures as those described in the Step 4, Step 5 of the same Example 4, and Step 1, Step 2 of Example 5, the title compound was obtained as a white powder. $^1$H NMR (400 MHz, DMSO-d$_6$): 0.65 (d, J=6.4 Hz, 6H, 2×Me), 0.9–1.8 (m, 9H, C$\underline{H}_2$C$\underline{H}$Me$_2$ and pyran 3,4,5-methylene), 2.50 (m, 1H, C$\underline{H}$-iBu), 2.51 (d, J=4.7 Hz, 3H, CONHC$\underline{H}_3$), 2.80 and 2.96 (each m, 2H, Phe methylene of two pyran isomers), 3.23 and 3.61 (each d, J=10.7 Hz, C$\underline{H}_2$O-pyran of pyran isomer A), 3.40 and 3.55 (each d, J=10.7 Hz, C$\underline{H}_2$O-pyran of pyran isomer B), 3.32 and 3.70 (two m, 2H, pyran 6-methylene), 4.36 (m, 1H, CONHC$\underline{H}$), 4.36 and 4.46 (each m, 1H, anomeric CH of two pyran isomers), 5.16 and 5.19 (each s, 1H, tertiary OH of two pyran isomers), 7.0–7.2 (m, 5H, Ph), 7.91 (broad s, 1H, CON$\underline{H}$CH$_3$), 8.23 and 8.25 (each d, J=7.5 Hz, 1H, CON$\underline{H}$CH of two pyran isomers), 8.81 (broad s, 1H, NHO$\underline{H}$), and 10.60 ppm (broad s, 1H, N$\underline{H}$OH).

EXAMPLE 7

[(2R,3S)-3-Hydroxy-4-hydroxyamino-3-hydroxymethyl-2-isobutyl-succinyl]-L-phenylalanine-N-methylamide

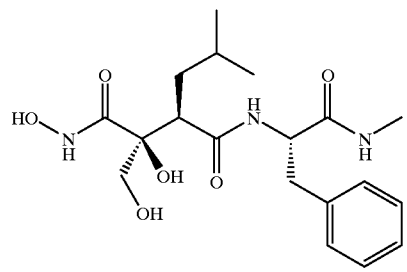

The compound described in Example 5 above (64 mg, 0.133 mmol) was dissolved in 80% aqueous ethanol (5 mL), and pyridinium p-toluenesulfonate (64 mg, 0.127 mmol) was added. The solution was heated to 50° C. for 3 h, the solvent was removed under reduced pressure and the residue was purified by reverse phase chromatography over silica (water and ethanol gradient elution) to afford the title product as a white solid (45.8 mg, 0.116 mmol; 87%). $^1$H NMR (600 MHz, DMSO-d$_6$): 0.70 and 0.73 (each d, J=6.6 Hz, 6H, 2×Me), 0.85 and 1.55 (each m, 2H, C$\underline{H}_2$CHMe$_2$), 1.15 (m, 1H, CH$_2$C$\underline{H}$Me$_2$), 2.54 (d, J=4.4 Hz, 3H, CONHC$\underline{H}_3$), 2.55 (m, 1H, C$\underline{H}$-iBu), 2.80 and 2.92 (each m, 2H, Phe methylene), 2.90 and 3.40 (each m, 2H, C$\underline{H}_2$OH), 4.45 (m, 2 H, CONHC$\underline{H}$ and CH$_2$O$\underline{H}$), 4.95 (s, 1H, tertiary OH), 7.1–7.3 (m, 5H, Ph), 7.83 (broad s, 1H, CON$\underline{H}$CH$_3$), 8.12 (broas s, 1H, CON$\underline{H}$CH), 8.65 (broad s, 1H, NHO$\underline{H}$), and 10.14 ppm (broad s, 1 H, N$\underline{H}$OH).

EXAMPLE 8

[(2R,3S)-4-Hydroxyamino-2-isobutyl-3-(2-tetrahydropyranyl)oxy-3-(2-tetrahydropyranyl)oxymethylsuccinyl]-L-tert-leucine-N-methylamide

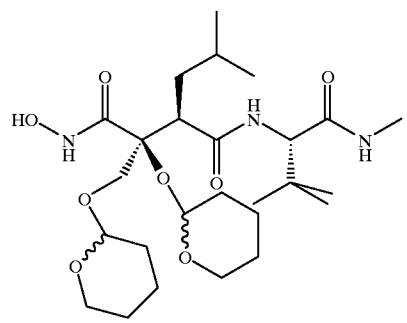

Step 1: [(2R,3S)-4-Benzhydryloxy-2-isobutyl-3-(2-tetrahydro-pyranyl)oxy-3-(2-tetrahydropyranyl)oxyethylsuccinyl]-L-tert-leucine-N-methylamide A solution of the compound from Example 1, Step 3 2.7 g, 5.3 1 mmol) in dichloromethane (50 mL) was treated at 0° C. with pyridinium-p-toluenesulfonate (150 mg) and 3,4-dihydro-2H-pyran (10 mL, 11 mmol). The mixture was kept in a cold room (4° C.) for 3 days, then diluted with ethyl acetate (150 mL) and sequentially washed with 4% aqueous HCl, saturated aqueous sodium bicarbonate, and water. After drying over Na$_2$SO$_4$ and evaporation, a colourless oil was obtained, which was treated with petroleum ether (150 mL) and kept at 4° C. overnight. Fractionation by silica gel chromatography from the mono-pyranyl adduct (Example 1, Step 4) afforded the title compound.

Step 2: [(2R,3S)-4-Hydroxy-2-isobutyl-3-(2-tetrahydropyranyl)-oxy-3-(2-tetrahydropyranyl) oxymethylsuccinyl]-L-tert-leucine-N-methylamide The compound from Step 1 above (0.9 g) was taken up in ethanol (35 mL) and exposed to a hydrogen atmosphere in the presence of 10% Pd on charcoal (0.43 g) overnight. The catalyst was removed by filtration (Celite$^R$ filter aid), washed with additional ethanol, and the combined ethanol solution was evaporated to dryness. The residue was taken up with n-hexane, stirred for 30 min, and the resulting white powder was collected by filtration, thereby obtaining the title compound (620 mg).

Step 3: [(2R,3S)-2-Isobutyl-4-(4-nitrobenzyloxyamino)-3-(2-tetrahydropyranyl)oxy-3-(2-tetrahydropyranyl) oxymethyl-succinyl]-L-tert-leucine-N-methylamide A solution of the compound from Step 2 above (620 mg) in acetonitrile (35 mL) was treated with O-(4-nitrobenzyl)-hydroxylamine hydrochloride (324 mg), N-methylmorpholine (0.35 mL) and TBTU (555 mg) for 20 hr at room temperature. The mixture was taken up in ethyl acetate, and sequentially washed with 4% HCl and 4% sodium hydrogen carbonate. Evaporation and flash-chromatography over silica (EtOAc/hexane) afforded the title compound as a white solid (385 mg).

Step 4: [(2R,3S)-4-Hydroxyamino-2-isobutyl-3-(2-tetrahydro-pyranyl)oxy-3-(2-tetrahydropyranyl) oxymethylsuccinyl]-L-tert-leucine-N-methylamide The compound from Step 3 above (100 mg) was taken up in ethanol (15 mL) and exposed to a hydrogen atmosphere in the presence of 10% Pd on charcoal (20 mg) for 12 hr. The catalyst was removed by filtration (Celite$^R$ filter aid), washed with additional ethanol, and the combined ethanol solution was evaporated to dryness. The residue was taken up with n-hexane, stirred for 30 min, and the resulting white powder was collected by filtration, thereby obtaining the title compound (diastereomeric mixture at the anomeric tetrahydropyran carbon atom; 27 mg). $^1$H NMR (400 MHz, DMSO-d$_6$): 0.75 (d, J=6.8 Hz, 6 H, 2×Me), 0.87 (s, 9H, t-Bu), 1.0–1.8 (m, 15H, CH$_2$CHMe$_2$ and pyran 3,4,5-methylene), 2.51 (d, J=4.7 Hz, 3H, CONHCH$_3$), 2.80 (m, 1H, CH-iBu), 3.3–3.9 (m, 6H, CH$_2$O-pyran and pyran 6-methylene), 4.03 (d, J=9.0 Hz, 1H, CONHCH), 4.46 and 5.20 (each m, 1H, anomeric CH of two pyrans), 7.40 (broad s, 1H, CONHCH$_3$), 7.70 (m, 1H, CONHCH), 8.78 (broad s, 1H, NHOH), and 10.31 ppm (broad s, 1H, NHOH).

EXAMPLE 9

[(2R,3S)-3-Acetoxymethyl-3-hydroxy-4-hydroxyamino-2-isobutyl-succinyl]-L-tert-leucine-N-methylamide

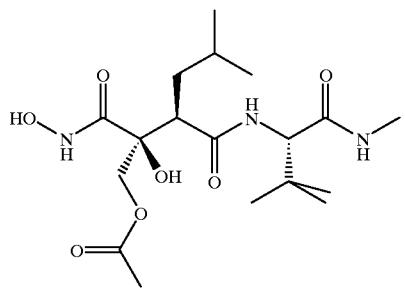

Step 1: [(2R,3S)-3-Acetoxymethyl-4-benzyloxy-3-hydroxy-2-isobutylsuccinyl]-L-tert-leucine-N-methylamide A crude sample of (2R,3S)-(3-acetoxymethyl-4-benzyloxy-3-hydroxy-2-isobutyl)succinic acid (1.77 g, 5.02 mmol), obtained as described in Preparation 4, was dissolved in dry DMF (10 mL). To this solution, L-tert-leucine-N-methylamide (0.72 g, 5.02 mmol) and HOBT (1-hydroxybenzotriazole hydrate; 658 mg, 4.87 mmol) were added at room temperature, followed by dropwise addition at 0° C. of a solution of DCC (dicyclohexylcarbodiimide; 1.04 g, 5.02 mmol) in THF (10 mL). The mixture was kept at 0° C. for 30 min, then kept under stirring for 5 h at room temperature, and finally allowed to stand overnight at 0° C. Dicyclohexylurea was filtered off, the solvent was removed in vacuo, the residue was taken up in ethyl acetate, and the solution was sequentially washed with 10% aqueous citric acid (50 mL), saturated aqueous sodium bicarbonate (50 mL), and brine (50 mL). After drying over Na$_2$SO$_4$, the solvent was removed to give an oil. This residue was taken up in ethyl acetate and left aside to allow for separation of a further amount of dicyclohexylurea. After filtration and evaporation, the residue was tritured with isopropyl ether, thereby obtaining a first crop of the title product (0.95 g). Examination of the mother liquors revealed the presence of the benzotriazolyl ester ("active ester") of the starting material. After evaporation, this material was allowed to react with a further amount of L-tert-butyl-glycine-N-methylamide (0.3 g) in dry DMF (5 mL) for 65 hr at room temperature. Work-up as before gave a second crop of the title product, crystallizing from ethyl ether (280 mg). Flash chromatography over silica of the mother liquors gave a third crop (230 mg). The three crops were combined (1.46 g, 3.06 mmol; 61%).

Step 2: [(2R,3S)-3-Acetoxymethyl-3,4-dihydroxy-2-isobutyl-succinyl]-L-tert-leucine-N-methylamide The compound from Step 1 above (0.9 g, 1.88 mmol) was taken up in ethanol (50 mL) and exposed to a hydrogen atmosphere in the presence of 5% Pd on charcoal (0.35 g) for 7 hr. A further amount of the catalyst (0.15 g) was added, and hydrogenation was continued for 16 hr. The catalyst was removed by filtration (Celite$^R$ filter aid), washed with additional ethanol, and the combined ethanol solution was evaporated to dryness, thereby obtaining the title product (essentially pure by HPLC) as a white solid (0.73 g, 1.88 mmol; quantitative yield).

Step 3: [(2R,3S)-3-Acetoxymethyl-4-benzyloxyamino-3-hydroxy-2-isobutylsuccinyl]-L-tert-leucine-N-methylamide The compound from Step 2 above (720 mg, 1.86 mmol) was dissolved in acetonitrile (25 mL). To this solution, O-benzylhydroxylamine hydrochloride (326 mg, 2.05 mmol), N-methylmorpholine (0.45 mL, 4.09 mmol), and O-benzotriazol-yl-N,N,N',N'-tetramethyluronium tetrafluoroborate (TBTU; 717 mg, 2.23 mmol) were added in this order. After stirring for 26 h at room temperature, the solvent was removed under reduced pressure and the residue was taken up in ethyl acetate. Sequential washing with saturated aqueous sodium bicarbonate, 2N aqueous HCl and water, followed by drying over Na$_2$SO$_4$ and evaporation, left a residue which was purified by flash chromatography over silica (n-hexane and ethyl acetate gradient elution), thereby obtaining the title product (230 mg, 0.46 mmol; 25%).

Step 4: [(2R,3S)-3-Acetoxymethyl-3-hydroxy-4-hydroxyamino-2-isobutylsuccinyl]-L-tert-leucine-N-methylamide A solution of the compound from Step 3 above (230 mg, 0.46 mmol) in ethanol (20 mL) was exposed to a hydrogen atmosphere in the presence of 5% Pd on charcoal (74 mg) for 90 min. The catalyst was removed by filtration (Celite$^R$ filter aid), washed with additional ethanol, and the combined ethanol solution was evaporated to dryness. The residue was taken up with isopropyl ether, stirred for 15 min, and the resulting white powder was collected by filtration, thereby obtaining the title compound as a white solid (135 mg, 0.335 mmol; 73%). $^1$H NMR (400 MHz, DMSO-d$_6$): 0.77 and 0.80 (each d, J=6.7 Hz, 6 H, 2×Me), 0.91 (s, 9H, t-Bu), 0.96 and 1.63 (each m, 2H, C$\underline{H}_2$CHMe$_2$), 1.28 (m, 1H, CH$_2$CH$\underline{H}$Me$_2$), 1.94 (s, 3H, COCH$_3$), 2.54 (d, J=4.7 Hz, 3H, CONHC$\underline{H}_3$), 2.97 (dd, J=3.5 and 11.7 Hz, 1H, C$\underline{H}$-iBu), 3.99 (d, J=10.0 Hz, 1H, CONHC$\underline{H}$), 4.15 (m, 2H, C$\underline{H}_2$OAc), 5.40 (s, 1H, tertiary OH), 7.88 (q, J=4.7 Hz, 1H, CON$\underline{H}$CH$_3$), 8.19 (d, J=10.0 Hz, 1H, CON$\underline{H}$CH), 8.80 (s, 1H, NHO$\underline{H}$), and 10.42 ppm (broad s, 1H, N$\underline{H}$OH).

EXAMPLE 10

[(2R,3S)-3-Acetoxymethyl-3-hydroxy-4-hydroxyamino-2-isobutyl-succinyl]-L-phenylalanine-N-methylamide

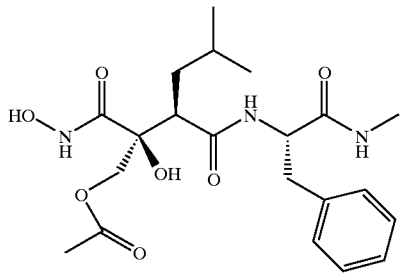

Starting from (2R,3S)-(3-Acetoxymethyl-4-benzyloxy-3-hydroxy-2-isobutyl)succinic acid (Preparation 4), but substituting L-phenylalanine-N-methylamide for L-tert-leucine-N-methylamide, and following a procedure analogous to that described in Example 9, the title product was obtained. $^1$H NMR (400 MHz, DMSO-d$_6$): 0.70 and 0.720 (each d, J=6.5 Hz, 6H, 2×Me), 0.80 and 1.70 (each m, 2H, C$\underline{H}_2$CHMe$_2$), 1.20 (m, 1H, CH$_2$C$\underline{H}$Me$_2$), 1.88 (s, 3H, COCH$_3$), 2.50 (d, J=4.7 Hz, 3H, CONHC$\underline{H}_3$), 2.62 (m, 1H, C$\underline{H}$-iBu), 2.77 and 2.89 (each m, 1H, C$\underline{H}_2$Ph), 3.48 and 3.95 (each d, J=11.1 Hz, C$\underline{H}_2$OAc), 4.48 (m, 1H, CONHC$\underline{H}$), 5.20 (s, 1H, tertiary OH), 7.0–7.2 (m, 5H, Ph), 7.82 (broad s, 1H, CON$\underline{H}$CH$_3$), 8.42 (broad s, 1H, CON$\underline{H}$CH), 8.65 (broad s, 1H, NHO$\underline{H}$), and 10.37 ppm (broad s, 1H, N$\underline{H}$OH).

EXAMPLE 11

[(2R,3S)-3-Acetoxymethyl-3-hydroxy-4-hydroxyamino-2-isobutyl-succinyl]-L-tert-leucine-N-(4-pyridyl)amide

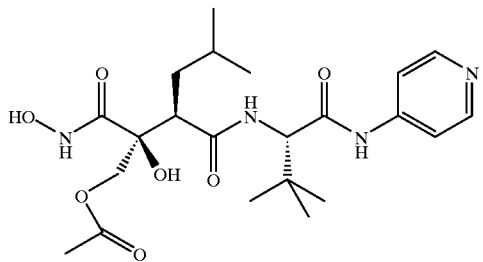

Starting from (2R,3S)-(3-Acetoxymethyl-4-benzyloxy-3-hydroxy-2-isobutyl)succinic acid (Preparation 4), but substituting L-phenylalanine-N-methylamide for L-tert-leucine-N-(4-pyridyl)-amide, and following a procedure analogous to that described in Example 9, the title product was obtained. $^1$H NMR (400 MHz, DMSO-d$_6$): 0.73 and 0.80 (each d, J=6.4 Hz, 6H, 2×Me), 0.90 and 1.65 (each m, 2H, C$\underline{H}_2$CHMe$_2$), 0.99 (S, 9H, t-Bu), 1.30 (m, 1H, CH$_2$CH$\underline{H}$Me$_2$), 1.94 (s, 3H, COCH$_3$), 3.05 (dd, J=3.6 and 11.5 Hz, 1H, C$\underline{H}$-iBu), 4.03 and 4.17 (each d, J=11.1 Hz, 1H, C$\underline{H}_2$OAc), 4.35 (d, J=8.1 Hz, 1H, CONHC$\underline{H}$), 5.24 (s, 1H, tertiary OH), 7.52 (d, J=6.4 Hz, 2H, 2,6-pyridyl protons), 8.40 (d, J=6.4 Hz, 2H, 3,5-pyridyl protons), 8.40 (s, 1H, CON$\underline{H}$CH), 8.82 (broad s, 1H, NHO$\underline{H}$), 10.48 (s, 1H, CON$\underline{H}$-pyr), and 10.50 ppm (broad s, 1H, N$\underline{H}$OH).

EXAMPLE 12

[(2R,3S)-3-Hydroxy-4-hydroxyamino-3-hydroxymethyl-2-isobutyl-succinyl]-L-tert-leucine-N-(4-pyridyl)amide

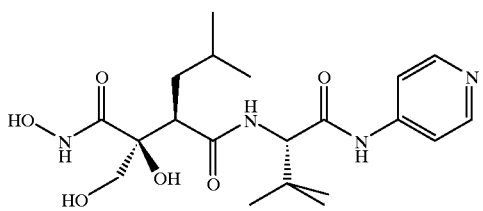

A solution of [(2R,3S)-3-Acetoxymethyl-3-hydroxy-4-hydroxy-amino-2-isobutyl-succinyl]-L-tert-leucine-N-(4-pyridyl)amide (Example 11; 10.5 mg) in methanol (2 mL) was treated with sodium methoxide (2.45 mg) for 1 hr at room temperature. After addition of acetic acid (0.025 mL), the solution was passed trough a reverse-phase (RP-C-18) column, eluting with EtOH/H$_2$O 3:1. Pooled fractions were liophilized, to afford the title compound as a white liophile, 8 mg. $^1$H NMR (400 MHz, DMSO-d$_6$): 0.74 and 0.80 (each d, J=6.4 Hz, 6H, 2×Me), 0.90 and 1.65 (each m, 2H, C$\underline{H}_2$CHMe$_2$), 0.99 (s, 9H, t-Bu), 1.30 (m, 1H, CH$_2$C$\underline{H}$Me$_2$), 2.90 (dd, J=3.6 and 11.7 Hz, 1H, C$\underline{H}$-iBu), 3.20 and 3.65 (each m, 1H, C$\underline{H}_2$OH), 4.32 (d, J=8.2 Hz, 1H, CONHC$\underline{H}$), 4.68 (dd, J=4.4 and 7.0 Hz, CH$_2$O$\underline{H}$9, 5.04 (s, 1H, tertiary OH), 7.53 (d, J=6.1 Hz, 2H, 2,6-pyridyl protons), 8.12 (d, J=8.2 Hz, 1H, CON$\underline{H}$CH), 8.40 (d, J=6.1 Hz, 2H, 3,5-pyridyl protons), 8.72 (d, J=2.0 Hz, 1H, NHO$\underline{H}$), 10.22 (d, J=2.0 Hz, 1H, N$\underline{H}$OH), and 10.45 ppm (s, 1H, CON$\underline{H}$-pyr).

EXAMPLE 13

[(2R,3S)-3-Hydroxy-4-hydroxyamino-2-isobutyl-3-(trimethyl-acetoxy)methyl-succinyl]-L-text-leucine-M-methylamide

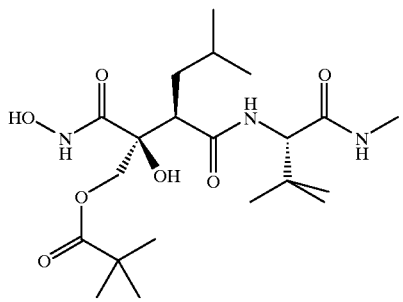

Step 1: (2R,3S)-[4-Benzyloxy-3-hydroxy-2-isobutyl-3-(trimethyl-acetoxy)methyl]succinic acid A solution in dichloromethane (40 mL) of tert-butyl (2R,3S)-(4-benzyloxy-3-hydroxy-3-hydroxymethyl-2-isobutyl)succinate (1.83 g), obtained as described in Preparation 3, was treated at 0° C. with pivaloyl chloride (0.74 mL) and triethylamine (0.84 mL). After standing for 48 hr at room temperature, the solution was sequentially washed with water, 4% HCl, and 4% sodium hydrogen carbonate. Evaporation in vacuo left a residue, which was taken up in dichloromethane (5 mL) and treated at room temperature for 2 hr with trifluoroacetic acid (4 mL) and anisole (0.5 mL). Concentration and flash-chromatography gave the title product as a waxy solid (1.55 g)

Step 2: [(2R,3S)-4-Benzyloxy-3-hydroxy-2-isobutyl-3-(trimethyl-acetoxy)methyl-succinyl]-L-tert-leucine-N-methylamide A solution of the compound from Step 1 above (925 mg) in dry DMF (5 mL) was treated with L-tert-leucine-N-methylamide (375 mg) and triethylamine (0.3 mL). After cooling to 0° C., a solution of DCC (540 mg) in dry DMF (3 mL) was added. The mixture was let rise to room temperature, left aside for 6 days, and finally stirred at 50° C. for 24 hr. Partitioning between EtOAc and 4% HCl, followed by washing with 4% sodium hydrogen carbonate and evaporation of the solvent, afforded the crude title product (800 mg).

Step 3: [(2R,3S)-3,4-Dihydroxy-2-isobutyl-3-(trimethylacetoxy)-methyl-succinyl]-L-tert-leucine-N-methylamide The compound from Step 2 above (700 mg) in ethanol (50 mL) was exposed to a hydrogen atmosphere in the presence of 5% Pd/C (330 mg) at room temperature for 30 hr. Filtration of the catalyst and evaporation in vacuo left the crude title product (465 mg).

Step 4: [(2R,3S)-4-Benzyloxyamino-3-hydroxy-2-isobutyl-3-(trimethylacetoxy)methyl-succinyl]-L-tert-leucine-N-methylamide The compound from Step 3 above (450 mg) in acetonitrile (30 mL) was treated with O-(benzyl)hydroxylamine hydrochloride (188 mg), N-methylmorpholine (0.258 mL), and TBTU (412 mg) at room temperature for 18 hr. Work-up (EtOAc/water, 4% HCl, saturated sodium hydrogen carbonate) and flash-chromatography afforded the title product as a white solid (103 mg).

Step 5: [(2R,3S)-3-Hydroxy-4-hydroxyamino-2-isobutyl-3-(tri-methylacetoxy)methyl-succinyl]-L-tert-leucine-N-methylamide The compound from Step 4 above (100 mg) in ethanol (10 mL) was exposed to a hydrogen atmosphere in the presence of 5% Pd/C (35 mg) at room temperature for 2 hr. Filtration of the catalyst and evaporation in vacuo afforded the title product as a white solid (77 mg). $^1$H NMR (400 MHz, DMSO-$d_6$): 0.73 and 0.77 (each d, J=6.4 Hz, 6H, 2×Me), 0.88 (s, 9H, t-Bu of t-leucine), 1.05 (s, 9H, t-Bu of pivalate), 0.90 and 1.60 (each m, 2H, C$\underline{H}_2$CHMe$_2$), 1.23 (m, 1H, CH$_2$C$\underline{H}$Me$_2$), 2.50 (d, J=4.7 Hz, 3H, CONHC$\underline{H}_3$), 2.98 (dd, J=3.4 and 11.9 Hz, 1H, C$\underline{H}$-iBu), 3.98 and 4.09 (each d, J=11.1 Hz, 2H, C$\underline{H}_2$OCO), 4.12 (d, J=8.9 Hz, 1H, CONHC$\underline{H}$), 5.26 (s, 1H, tertiary OH), 7.85 (q, J=4.7 Hz, 1H, CON$\underline{H}$CH$_3$), 8.20 (d, J=8.9 Hz, 1H, CON$\underline{H}$CH), 8.72 (s, 1H, NHO$\underline{H}$), and 10.35 ppm (broad s, 1H, N$\underline{H}$OH).

EXAMPLE 14
[(2R,3S)-3-Hydroxy-4-hydroxyamino-3-hydroxymethyl-2-isobutyl-succinyl]-L-tert-leucine-N-tert-butylamide

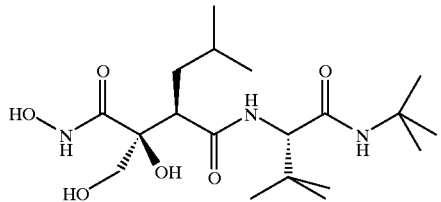

Step 1: [(2R,3S)-3-Acetoxymethyl-4-benzyloxy-3-hydroxy-2-isobutylsuccinyl]-L-tert-leucine-N-tert-butylamide (2R,3S)-(3-Acetoxymethyl-3-benzyloxycarbonyl-2-isobutyl)-propiolactone (1.6 g), obtained as described in Preparation 9, was dissolved in dry DMF (10 mL). To this solution, L-tert-leucine-N-tert-butylamide (0.85 g) and a catalytic amount of HOBT (1-hydroxybenzotriazole hydrate; 80 mg) were added at room temperature. After stirring overnight at room temperature, the solvent was removed in vacuo, the residue was taken up in ethyl acetate, and the solution was sequentially washed with 10% aqueous citric acid (50 mL), saturated aqueous sodium bicarbonate (50 mL), and brine (50 mL). Drying over Na$_2$SO$_4$ and evaporation in vacuo afforded the crude title product as a syrup.

Step 2: [(2R,3S)-3-Acetoxymethyl-3,4-dihydroxy-2-isobutyl-succinyl]-L-text-leucine-N-tert-butylamide The crude compound from Step 1 above was taken up in ethanol (100 mL) and exposed to a hydrogen atmosphere in the presence of 5% Pd on charcoal (0.7 g) for 7 hr. A further amount of the catalyst (0.3 g) was added, and hydrogenation was continued for 16 hr. The catalyst was removed by filtration (Celite$^R$ filter aid), washed with additional ethanol, and the combined ethanol solution was evaporated to dryness, thereby obtaining the title product (1.5 g).

Step 3: [(2R,3S)-3-Acetoxymethyl-4-benzyloxyamino-3-hydroxy-2-isobutylsuccinyl]-L-tert-leucine-N-tert-butylamide The compound from Step 2 above was dissolved in acetonitrile (50 mL). To this solution, O-benzylhydroxylamine hydrochloride (660 mg), N-methylmorpholine (0.9 mL), and O-benzotriazol-yl-N,N,N',N'-tetramethyluronium tetrafluoroborate (TBTU; 1.5 g) were added in this order. After stirring for 24 h at room temperature, the solvent was removed under reduced pressure and the residue was taken up in ethyl acetate. Sequential washing with saturated aqueous sodium bicarbonate, 2N aqueous HCl and water, followed by drying over Na$_2$SO$_4$ and evaporation, left a residue which was purified by flash chromatography over silica (n-hexane and ethyl acetate gradient elution), thereby obtaining the title product (0.7 g).

Step 4: [(2R,3S)-3-Acetoxymethyl-3-hydroxy-4-hydroxyamino-2-isobutylsuccinyl]-L-tert-leucine-N-tert-butylamide A solution of the compound from Step 3 above in ethanol (60 mL) was exposed to a hydrogen atmosphere in the presence of 5% Pd on charcoal (200 mg) for 90 min. The catalyst was removed by filtration (Celite^R filter aid), washed with additional ethanol, and the combined ethanol solution was evaporated to dryness. The residue was taken up with isopropyl ether, stirred for 15 min, and the resulting white powder was collected by filtration, thereby obtaining the title compound as a white solid (400 mg).

Step 5: [(2R,3S)-3-Hydroxy-4-hydroxyamino-3-hydroxymethyl-2-isobutyl-succinyl]-L-tert-leucine-N-tert-butylamide A solution of the compound from Step 4 above in methanol (50 mL) was treated with sodium methoxide (100 mg) for 1 hr at room temperature. After addition of acetic acid (0.1 mL), the solution was passed trough a reverse-phase (RP-C-18) column, eluting with EtOH/H$_2$O 3:1. Pooled fractions were liophilized, to afford the title compound as a white liophile, 320 mg. $^1$H NMR (400 MHz, DMSO-d$_6$): 0.76 and 0.79 (each d, J=6.8 Hz, 6H, 2×Me), 0.90 (s, 9H, t-Bu of t-leucine), 1.21 (s, 9H, CONH-t-Bu), 0.90 and 1.65 (each m, 2H, CH$_2$CHMe$_2$), 1.30 (m, 1H, CH$_2$CHMe$_2$), 2.85 (dd, J=3.4 and 11.9 Hz, 1H, CH-iBu), 3.22 (dd, J=4.7 and 10.7 Hz, 1H, CH(H)OH), 3.63 (dd, J=7.3 and 10.7 Hz, 1H, CH(H)OH), 4.18 (d, J=9.8 Hz, 1H, CONHCH), 4.59 (dd, J=4.7 and 7.3 Hz, 1H, CH$_2$OH), 5.14 (s, 1H, tertiary OH), 7.50 (s, 1H, CONH-tBu), 7.94 (d, J=9.8 Hz, 1H, CONHCH), 8.68 (d, J=2.1 Hz, 1H, NHOH), and 10.17 ppm (d, J=2.1 Hz, 1H, NHOH).

EXAMPLE 15

[(2R,3S)-3-Hydroxy-4-hydroxyamino-3-hydroxymethyl-2-isobutyl-succinyl]-L-cyclohexylglycine-N-tert-butylamide

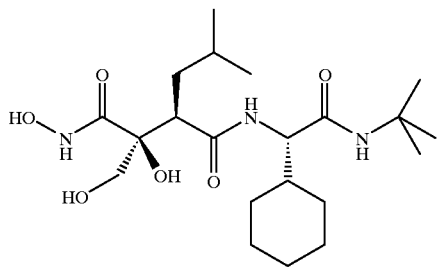

Starting from (2R,3S)-(3-acetoxymethyl-3-benzyloxycarbonyl-2-isobutyl)-propiolactone, obtained as described in Preparation 9, and by the same procedure as that described in Example 14, but replacing L-tert-leucine-N-tert-butylamide with L-cyclohexylglycine-N-tert-butylamide, the title compound was obtained. $^1$H NMR (400 MHz, DMSO-d$_6$): 0.76 and 0.79 (each d, J=6.4 Hz, 6H, 2×Me), 1.20 (s, 9H, CONH-t-Bu), 0.8–1.7 (m, 14 H, CH$_2$C HMe$_2$ and cyclohexyl protons), 2.73 (dd, J=3.4 and 11.9 Hz, 1H, CH-iBu), 3.20 (dd, J=4.7 and 10.8 Hz, 1H, CH(H)OH), 3.59 (dd, J=7.3 and 10.8 Hz, 1H, CH(H)OH), 4.05 (d, J=8.5 Hz, 1H, CONHCH), 4.60 (dd, J=4.7 and 7.3 Hz, 1H, CH$_2$O H), 5.12 (s, 1H, tertiary OH), 7.38 (s, 1H, CONH-tBu), 8.16 (d, J=8.5 Hz, 1H, CONHCH), 8.67 (broad s, 1H, NHOH), and 10.17 ppm (broad s, 1H, NHOH).

EXAMPLE 16

[(2R,3S)-3-(N-Cyclohexylaminocarbonyl)oxymethyl-3-hydroxy-4-hydroxyamino-2-isobutylsuccinyl]-L-tert-leucine-N-methylamide

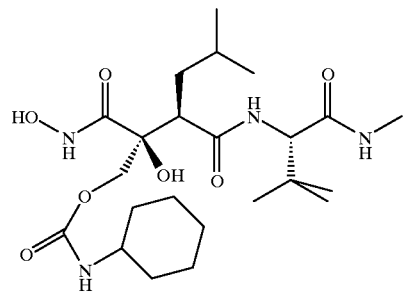

Step 1: (2R,3S)-4-Benzyloxy-3-(N-cyclohexylaminocarbonyl)-oxymethyl-3-hydroxy-2-isobutylsuccinic acid 4-Dimethylaminopyridine (200 mg) and cyclohexylisocyanate (5 mL) were added to a solution in dichloromethane (30 mL) of tert-butyl (2R,3S)-(4-benzyloxy-3-hydroxy—3-hydroxymethyl -2-isobutyl) succinate (6.5 g), obtained as described in Preparation 3. After stirring for 16 hr at room temperature, the reaction mixture was quenched with methanol (20 mL) and the solvent removed in vacuo. Cold (−20° C.) 95% aqueous trifluoroacetic acid (30 mL) was added to the residue, and the solution was let standing for 4 hr at room temperature. Concentration and flash-chromatography over silica (hexane/EtOAc gradient elution, from 80:20 to 0:100) and evaporation of pooled fractions left a waxy residue, which was triturated with isopropyl ether to give the title product as a white powder (5.9 g).

Step 2: [(2R,3S)-4-Benzyloxy-3-(N-cyclohexylaminocarbonyl)-oxymethyl-3-hydroxy-2-isobutylsuccinyl]-L-tert-leucine-N-methylamide The compound from Step 1 above (5.9 g) was dissolved in a mixture of DMF (45 mL) and dichloromethane (30 mL). After cooling to 0° C., HOBT (2.03 g), N,N-dimethylaminopropyl-N'-ethyl carbodiimide hydrochloride (2.88 g) and N-methylmorpholine (1.76 mL) were added, followed, after 1 hr at 0° C., by tert-leucine-N-methylamide (2.88 g). The reaction was let standing for 2 days at room temperature, then heated at 65° C. for 3 hr. Partitioning beween ethyl acetate and water, followed by sequential washing with 40 HCl and saturated sodiun hydrogen carbonate, drying (Na$_2$SO$_4$) and evaporation, left the crude title product. Flash-chromatography over silica afforded the pure compound as a white foam, 6.3 g.

Step 3: [(2R,3S)-3-(N-Cyclohexylaminocarbonyl)oxymethyl-3,4-dihydroxy-2-isobutylsuccinyl]-L-tert-leucine-N-methylamide The compound from Step 2 above (6.3 g) in ethanol (400 mL) was exposed to a hydrogen atmosphere for 2 hr in the presence of 5% Pd/C (1.5 g). Filtration of the catalyst and evaporation gave the title compound as a white foam (5.1 g).

Step 4: [(2R,3S)-4-Benzyloxyamino-3-(N-cyclohexylamino-carbonyl)oxymethyl-3-hydroxy-2-isobutylsuccinyl]-L-tert-leucine-N-methylamide The compound from Step 3 above (4.15 g) in acetonitrile (150 mL) was treated with O-(benzyl)hydroxylamine hydrochloride (1.67 g), N-methylmorpholine (2.14 mL) and TBTU (3.37 g). After 20 hr at room temperature, aqueous work-up and flash-chromatography gave the title product as a white foam (1.8 g).

Step 5: [(2R,3S)-3-(N-Cyclohexylaminocarbonyl)oxymethyl-3-hydroxy-4-hydroxyamino-2-isobutylsuccinyl]-L-tert-leucine-N-methylamide The compound from Step 4 above (1.8 g) in ethanol (150 mL) was exposed to a hydrogen atmosphere for 5 hr in the presence of 5% Pd/C (150 mg). Filtration of the catalyst and evaporation left a waxy solid, which was tritured with ethyl ether (3×50 mL) to afford the title compound as a white powder (1.25 g). $^1$H NMR (400 MHz, DMSO-$d_6$): 0.76 and 0.80 (each d, J=6.4 Hz, 6H, 2×Me), 0.90 (s, 9H, t-Bu), 0.9–1.7 (m, 13H, C$\underline{H}_2$C$\underline{H}$Me$_2$ and cyclohexyl methylene protons), 2.97 (m, 1H, C$\underline{H}$-iBu), 3.17 (m, 1H, cyclohexyl methine proton), 3.91 and 4.06 (each d, J=11.7 Hz, 2H, C$\underline{H}_2$OCO), 4.14 (d, J=9.4 Hz, 1H, CONHC$\underline{H}$), 5.32 (s, 1H, tertiary OH), 6.89 (d, J=7.7 Hz, 1H, CON$\underline{H}$-cyclohexyl), 7.87 (q, J=4.3 Hz, 1H, CON$\underline{H}$-Me), 8.12 (d, J=9.4 Hz, 1H, CON$\underline{H}$CH), 8.75 (broad s, 1H, NHO$\underline{H}$), and 10.34 ppm (broad s, 1H, N$\underline{H}$OH).

EXAMPLE 17

By procedures similar to those described in Examples 1–16 above, the following compounds may be prepared:

17.1: [(2R,3S)-3-Hydroxy-4-hydroxyamino-3-hydroxymethyl-2-isobutylsuccinyl]-L-phenylalanine-N-tert-butylamide;

17.2: [(2R,3S)-3-Hydroxy-4-hydroxyamino-3-hydroxymethyl-2-isobutylsuccinyl]-L-phenylalanine-N-2-(morpholino)ethylamide;

17.3: [(2R,3S)-3-Hydroxy-4-hydroxyamino-3-hydroxymethyl-2-isobutylsuccinyl]-L-(O-tert-butyl)threonine-N-methylamide;

17.4: [(2R,3S)-3-Hydroxy-4-hydroxyamino-3-hydroxymethyl-2-isobutylsuccinyl]-L-tert-leucine-amide;

17.5: [(2R,3S)-3-Hydroxy-4-hydroxyamino-3-hydroxymethyl-2-isobutylsuccinyl]-L-tert-leucine-N-cyclopropylamide;

17.6: [(2R,3)-3-Hydroxy-4-hydroxyamino-3-hydroxymethyl-2-isobutylsuccinyl]-L-tert-leucine-N-cyclopentylamide;

17.7: [(2R,3S)-3-Hydroxy-4-hydroxyamino-3-hydroxymethyl-2-isobutylsuccinyl]-L-tert-leucine-N-(3-quinolyl)amide;

17.8: [(2R,3S)-3-Hydroxy-4-hydroxyamino-3-hydroxymethyl-2-isobutylsuccinyl]-L-tert-leucine-N-(5-quinolyl)amide;

17.9: [(2R,3S)-3-Hydroxy-4-hydroxyamino-3-hydroxymethyl-2-isobutylsuccinyl]-L-tert-leucine-N-(3-isoquinolyl)amide;

17.10: [(2R,3S)-3-Hydroxy-4-hydroxyamino-3-hydroxymethyl-2-isobutylsuccinyl]-L-tert-leucine-N-(3-quinuclidinyl)amide;

17.11: [(2R,3S)-3-Hydroxy-4-hydroxyamino-3-hydroxymethyl-2-isobutylsuccinyl]-L-tert-leucine-N-(3,4-methylenedioxy)anilide;

17.12: [(2R,3S)-3-Hydroxy-4-hydroxyamino-3-hydroxymethyl-2-isobutylsuccinyl]-L-(S-methyl)penicillamine-N-methylamide;

17.13: [(2R,3S)-3-Hydroxy-4-hydroxyamino-3-hydroxymethyl-2-isobutylsuccinyl]-L-[(S-methyl)penicillamine-sulfoxide]-N-methylamide;

17.14: [(2R,3S)-3-Hydroxy-4-hydroxyamino-3-hydroxymethyl-2-isobutylsuccinyl]-L-[(S-methyl)penicillamine-sulfone]-N-methylamide;

17.15: [(2R,3S)-3-Hydroxy-4-hydroxyamino-3-hydroxymethyl-2-isobutylsuccinyl]-L-cyclohexylalanine-N-methylamide;

17.16: [(2R,3S)-3-Hydroxy-4-hydroxyamino-3-hydroxymethyl-2-isobutylsuccinyl]-L-cyclohexylalanine-N-tert-butylamide;

17.17: [(2R,3S)-3-Hydroxy-4-hydroxyamino-3-hydroxymethyl-2-isobutylsuccinyl]-L-cyclohexylalanine-N-2-(1-morpholino)-methylamide;

17.18: [(2-R,3S)-3-Hydroxy-4-hydroxyamino-3-hydroxymethyl-2-isobutylsuccinyl]-L-cyclohexylalanine-N-2-(4-aminosulfonyl-phenyl)ethylamide;

17.19: [(2R,3S)-3-Hydroxy-4-hydroxyamino-3-hydroxymethyl-2-isabutylsuccinyl]-L-phenylalanine-N-2-(4-aminosulfonyl-phenyl)ethylamide;

17.20: [(2R,3S)-3-Hydroxy-4-hydroxyamino-3-hydroxymethyl-2-isobutylsuccinyl]-L-tert-leucine-N-2-(4-aminosulfonyl-phenyl)ethylamide;

17.21: [(2R,3S)-3-Hydroxy-4-hydroxyamino-3-hydroxymethyl-2-isobutylsuccinyl]-L-tert-leucine-N-(4-piperidyl)amide;

17.22: [(2R,3S)-3-Hydroxy-4-hydroxyamino-3-hydroxymethyl-2-isobutylsuccinyl]-L-cyclohexylglycine-N-(4-piperidyl)amide;

17.23: [(2R,3S)-3-Hydroxy-4-hydroxyamino-3-hydroxymethyl-2-isobutylsuccinyl]-L-cyclohexylglycine-N-(4-pyridyl)amide;

17.24: [(2R,3S)-3-Hydroxy-4-hydroxyamino-3-hydroxymethyl-2-isobutylsuccinyl]-L-2-pyridylalanine-N-tert-butylamide;

17.25: [(2R,3S)-3-Hydroxy-4-hydroxyamino-3-hydroxymethyl-2-isobutylsuccinyl]-L-3-pyridylalanine-N-(3,4-dioxymethylene)-anilide;

17.26: [(2R,3S)-3-Hydroxy-4-hydroxyamino-3-hydroxymethyl-2-isobutylsuccinyl]-L-7-isoquinolylalanine-N-methylamide;

17.27: [(2R,3S)-3-Hydroxy-4-hydroxyamino-3-hydroxymethyl-2-isobutylsuccinyl]-L-2-quinolylalanine-N-methylamide;

17.28: [(2R,3S)-3-Hydroxy-4-hydroxyamino-3-hydroxymethyl-2-isobutylsuccinyl]-L-(4-fluoro)phenylalanine-N-methylamide;

17.29: [(2R,3S)-3-Hydroxy-4-hydroxyamino-3-hydroxymethyl-2-isobutylsuccinyl]-L-(4-fluoro)phenylalanine-N-(4-pyridyl)amide;

17.30: [(2R,3S)-3-Hydroxy-4-hydroxyamino-3-hydroxymethyl-2-isobutylsuccinyl]-L-(4-thiazolyl)alanine-N-(4-pyridyl)amide;

17.31: [(2R,3S)-3-Hydroxy-4-hydroxyamino-3-hydroxymethyl-2-isobutylsuccinyl]-L-(4-thiazolyl)alanine-N-tert-butylamide;

17.32: [(2R,3S)-3-Hydroxy-4-hydroxyamino-3-hydroxymethyl-2-isobutylsuccinyl]-L-(5,6,7,8-tetrahydro-7-isoquinolyl)alanine-N-methylamide;

17.33: [(2R,3S)-3-Hydroxy-4-hydroxyamino-3-hydroxymethyl-2-isobutylsuccinyl]-(1-adamantyl)glycine-N-methylamide;

17.34: [(2R,3S)-3-Hydroxy-4-hydroxyamino-3-hydroxymethyl-2-isobutylsuccinyl]-L-(2-methoxyethyl)alanine-N-tert-butylamide;

17.35: [(2R,3S)-3-Hydroxy-4-hydroxyamino-3-hydroxymethyl-2-isobutylsuccinyl]-L-tert-leucine-N-[1-phenyl-1-(3-pyridyl)]-methylamide;

17.36: [(2R,3S)-2-Cyclopentylmethyl-3-hydroxy-4-hydroxyamino-3-hydroxymethylsuccinyl]-L-tert-leucine-N-methylamide;

17.37: [(2R,3S)-2-Cyclopentylmethyl-3-hydroxy-4-hydroxyamino-3-hydroxymethylsuccinyl]-L-tert-leucine-N-tert-butylamide;

17.38: [(2R,3S)-2-Cyclopentylmethyl-3-hydroxy-4-hydroxyamino-3-hydroxymethylsuccinyl]-L-tert-leucine-carboxamide;

17.39: [(2R,3S)-2-Cyclopentylmethyl-3-hydroxy-4-hydroxyamino-3-hydroxymethylsuccinyl]-L-tert-leucine-N-(4-pyridyl)amide;

17.40: [(2R,3S)-2-Cyclopentylmethyl-3-hydroxy-4-hydroxyamino-3-hydroxymethylsuccinyl]-L-(S-methyl)penicillamine-N-methyl-amide;
17.41: [(2R,3S)-2-Cyclopentylmethyl-3-hydroxy-4-hydroxyamino-3-hydroxymethylsuccinyl]-L-cyclohexylalanine-N-methylamide;
17.42: [(2R,3S)-2-Cyclopentylmethyl-3-hydroxy-4-hydroxyamino-3-hydroxymethylsuccinyl]-L-cyclohexylalanine-N-2-(1-morpholino)-ethylamide;
17.43: [(2R,3S)-2-Cyclopentylmethyl-3-hydroxy-4-hydroxyamino-3-hydroxymethylsuccinyl]-L-cyclohexylalanine-N-2-(4-amino-sulfonylphenyl)ethylamide;
17.44: [(2R,3S)-2-Cyclopentylmethyl-3-hydroxy-4-hydroxyamino-3-hydroxymethylsuccinyl]-L-tert-leucine-N-2-(4-aminosulfonyl-phenyl)ethylamide;
17.45: [(2R,3S)-2-Cyclopentylmethyl-3-hydroxy-4-hydroxyamino-3-hydroxymethyisuccinyl]-L-cyclohexylglycine-N-(4-pyridyl)amide;
17.46: [(2R,3S)-2-Cyclopentylmethyl-3-hydroxy-4-hydroxyamino-3-hydroxymethylsuccinyl]-L-3-pyridylalanine-N-(3,4-dioxymethylene)anilide;
17.47: [(2R,3S)-2-Cyclopentylmethyl-3-hydroxy-4-hydroxyamino-3-hydroxymethylsuccinyl]-L-(4-fluoro)phenylalanine-N-methyl-amide;
17.48: [(2R,3S)-2-(3-(4-Chlorophenyl)propyl)-3-hydroxy-4-hydroxyamino-3-hydroxymethylsuccinyl]-L-tert-leucine-N-methylamide;
17.49: [(2R,3S)-3-Hydroxy-4-hydroxyamino-3-hydroxymethyl-2-(3-(4-methoxyphenyl)propyl)succinyl]-L-tert-leucine-N-methylamide;
17.50: [(2R,3S)-2-(3-(4-Diphenyl)propyl)-3-hydroxy-4-hydroxy-amino-3-hydroxymethylsuccinyl]-L-tert-leucine-N-(4-pyridyl)-amide;
17.51: [(2R,3S)-3-Hydroxy-4-hydroxyamino-3-hydroxymethyl-2-(3-(4-methoxyphenyl)oxypropyl)succinyl]-L-tert-leucine-N-methyl-amide;
17.52: [(2R,33)-3-Hydroxy-4-hydroxyamino-3-hydroxymethyl-2-(5-phenylpentyl)succinyl]-L-tert-leucine-N-methylamide;
17.53: [(2R,3S)-3-Hydroxy-4-hydroxyamino-3-hydroxymethyl-2-(4-phenoxybutyl)succinyl]-L-tert-leucine-N-methylamide;
17.54: [(2R,3S)-3-Hydroxy-4-hydroxyamino-3-hydroxymethyl-2-(5-(4-propylphenyl)oxypentyl)succinyl]-L-tert-leucine-amide;
17.55: [(2R,3S)-2-(3-(Benzylaminocarbonyl)propyl)-3-hydroxy-4-hydroxyamino-3-hydroxymethylsuccinyl]-L-tert-leucine-N-methyl-amide;
17.56: [(2R,3S)-2-(3-(3,4-Difluorophenyl)aminocarbonyl)-propyl)-3-hydroxy-4-hydroxyamino-3-hydroxymethylsuccinyl]-L-tert-leucine-N-methylamide;
17.57: [(2R,33)-3-Hydroxy-4-hydroxyamino-3-hydroxymethyl-2-octylsuccinyl]-L-tert-leucine-N-methylamide;
17.58: [(2R,3S)-3-Hydroxy-4-hydroxyamino-3-hydroxymethyl-2-octylsuccinyl]-L-tert-leucine-N-(4-pyridyl)amide;
17.59: [(2R,3S)-3-Hydroxy-4-hydroxyamino-3-hydroxymethyl-2-(4-methoxyphenylsulfonyl)succinyl]-L-tert-leucine-N-methylamide;
17.60: [(2R,3S)-2-(4-Butoxyphenylsulfonyl)-3-hydroxy-4-hydroxyamino-3-hydroxymethylsuccinyl]-L-tert-leucine-N-methylamide;
17.61: [(2R,3S)-3-(N-Cyclohexylaminocarbonyl)oxymethyl-2-cyclopentylmethyl-3-hydroxy-4-hydroxyaminosuccinyl]-L-tert-leucine-N-methylamide;
17.62: [(2R,3S)-2-Cyclopentylmethyl-3-hydroxy-4-hydroxyamino-3-(N-piperidyl)carhonyloxymethyl-succinyl]-L-tert-leucine-N-methylamide;
17.63: [(2R,33)-3-Hydroxy-4-hydroxyamino-2-isobutyl-3-phenoxymethylsuccinyl]-L-tert-leucine-N-methylamide;
17.64: [(2R,3S)-3-(4-Aminophenyl)oxymethyl-3-hydroxy-4-hydroxyamino-2-isobutylsuccinyl]-L-tert-leucine-N-methylamide;
17.65: [(2R,3S)-2-Cyclopentylmethyl-3-(4-fluorophenyl)-oxymethyl-3-hydroxy-4-hydroxyaminosuccinyl]-L-tert-leucine-N-methylamide;
17.66: [(2R,3S)-2-Cyclopentylmethyl-3-(3,4-dioxymethylene)-phenoxymethyl-3-hydroxy-4-hydroxyaminosuccinyl]-L-tert-leucine-N-methylamide;
17.67: [(2R,3S)-3-Hydroxy-4-hydroxyamino-3-(4-hydroxymethyl-phenyl)oxymethyl-2-isobutylsuccinyl]-L-tert-leucine-N-methylamide;
17.68: [(2R,3S)-2-Cyclopentylmethyl-3-hydroxy-4-hydroxyamino-3-methoxymethylsuccinyl]-L-tert-leucine-N-methylamide;
17.69: [(2R,3S)-3-Hydroxy-4-hydroxyamino-2-isobutyl-3-(3-pyridyl)oxymethylsuccinyl]-L-tert-leucine-N-methylamide.

EXAMPLE 18

[(2R,3S)-3,4-Dihydroxy-2-isobutyl-3-(1-methyl-1,2,3,4-tetrazol-5-yl)thiomethyl)succinyl]-L-phenylalanine-N-methylamide

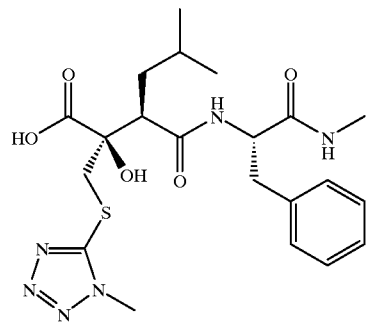

Step 1: [(2R,3S)-4-Benzhydryloxy-3-hydroxy-2-isobutyl-3-(1-methyltetrazol-5-yl)thiomethylsuccinyl]-L-phenylalanine-N-methylamide, and
[2R-[(2S)-2-Benzhydryloxycarbonyl-2-oxiranyl]-4-methylpentanoyl]-L-phenylalanine-N-methylamide A solution in dichloromethane (10 mL) of (2R,3S)-(4-benzhydryloxy-3-hydroxy-3-hydroxymethyl-2-isobutylsuccinyl)-L-phenylalanine-N-methylamide (100 mg; 0.183 mmol), prepared as described in Example 4, Step 3, was treated with triphenylphosphine (140 mg, 0.53 mmol), 5-mercapto-1-methyltetrazole (50 mg, 0.43 mmol), and diethyl azodicarboxylate (0.09 mL, 0.57 mmol). After stirring for 2 h at room temperature, the reaction mixture was partitioned between ethyl acetate and water. The organic layer was washed, in this order, with 2% aqueous HCl, saturated aqueous sodium bicarbonate and brine, then—dried over sodium sulfate and evaporated to dryness. Fractionation by flash chromatography over silica (n-hexane and ethyl acetate gradient elution) afforded, in this order:
[2R-[(2S)-2-Benzhydryloxycarbonyl-2-oxiranyl]-4-methylpentanoyl]-L-phenylalanine-N-methylamide, white foam (30 mg, 0.056 mmol; 31%). IR (film), $v_{max}$ 3296, 2957, 2870, 1736, and 1645 cm$^{-1}$, $^1$H NMR (400 MHz, DMSO-d$_6$): 0.71 and 0.72 (each d, J=7.0 Hz, 6H, 2×Me), 1.05 and 1.55 (each m, 2H, C$\underline{H}_2$CHMe$_2$), 1.30 (m, 1H, C$\underline{H}$Me$_2$), 2.12 and 2.57 (each d, J=5.6 Hz, 2H, oxirane methylene), 2.54 (d, J=4.4 Hz, 3H, CONHC$\underline{H}_3$), 2.73–3.21 (m, 3H, Phe methylene and C$\underline{H}$-iBu), 4.41 (m, 1H, CONHC$\underline{H}$), 6.81 (s, 1H, C$\underline{H}$Ph$_2$), 7.0–7.6 (m, 15H, 3×Ph), 7.85 (q, J=4.4 Hz, 1H, CON$\underline{H}$CH$_3$), and 8.23 ppm (d, J=8.5 Hz, 1H, CON$\underline{H}$CH); and [(2R,3S)-4-Benzhydryloxy-3-hydroxy-2-isobutyl-3-(1-methyl-tetrazol-5-yl)thiomethylsuccinyl]-L-phenylalanine-N-methylamide, (32 mg, 0.054 mmol; 30%), white foam, slightly impure from triphenylphosphine oxide.

Step 2: [(2R,3S)-3,4-Dihydroxy-2-isobutyl-3-(1-methyltetrazol-5-yl)thioethyisuccinyl]-L-phenylalanine-N-methylamide

[(2R,3S)-4-Benzhydryloxy-3-hydroxy-2-isobutyl-3-(1-methyl-tetrazol-5-yl)thiomethylsuccinyl]-L-phenylalanine-N-methylamide (20 mg, 0.031 mmol), as obtained from Step 1 above, was dissolved in dichloromethane (5 mL). Anisole (5 mL) and trifluoroacetic acid (1.5 mL) were added and the mixture left aside for 3 h. Concentration under reduced pressure left a waxy residue, which was triturated in ethyl ether. The title product was collected as a white solid by filtration (10 mg, 0.021 mmol; 68%). $^1$H NMR (400 MHz, DMSO-d$_6$): 0.68 and 0.70 (each d, J=8.8 Hz, 6H, 2×Me), 0.76 and 1.62 (each m, 2H, C$\underline{H}_2$CHMe$_2$), 1.14 (m, 1H, C$\underline{H}$Me$_2$), 2.51 (d, J=4.7 Hz, 3H, CONHC$\underline{H}_3$), 2.66 (dd, J=3.0 and 12.0 Hz, 1H, C$\underline{H}$-iBu), 2.75 and 2.92 (each m, 2H, Phe methylene), 2.97 and 3.46 (each d, J=13.2 Hz, 2H, C$\underline{H}_2$S), 3.86 (s, 3H, tetrazole N—C$\underline{H}_3$), 4.48 (m, 1H, CONHC$\underline{H}$), 5.38 (broad s, 1H, tertiary OH), 7.0–7.2 (m, 5 H, Ph), 7.84 (q, J=4.7 Hz, 1H, CON$\underline{H}$CH$_3$), 8.19 (d, J=8.1 Hz, 1H, CON$\underline{H}$CH), and 13.0 ppm (broad s, 1H, COOH).

EXAMPLE 19

Similarly, the following compounds may be prepared:

19.1: [(2R,3S)-3-Hydroxy-4-hydroxyamino-2-isobutyl-3-(1-methyl-1,2,3,4-tetrazol-5-yl)thiomethylsuccinyl]-L-tert-leucine-N-methylamide;

19.2: [(2R,3S)-2-Cyclopentylmethyl-3-hydroxy-4-hydroxyamino-3-(2-thienyl)thiomethylsuccinyl]-L-tert-leucine-N methylamide;

19.3: [(2R,3S)-3-Hydroxy-4-hydroxyamino-2-isobutyl-3-(2-pyridyl)thiomethylsuccinyl]-L-tert-leucine-N-methylamide;

19.4: [(2R,3S)-3-Hydroxy-4-hydroxyamino-2-isobutyl-3-(4-pyridyl)thiomethylsuccinyl]-L-tert-leucine-N-methylamide;

19.5: [(2R,3S)-2-Cyclopentylmethyl-3-hydroxy-4-hydroxyamino-3-(4-hydroxyphenyl)thiomethyl-2-isobutylsuccinyl]-L-tert-leucine-N-methylamide;

19.6: [(2R,3S)-2-Cyclopentylmethyl-3-hydroxy-4-hydroxyamino-3-methyl-thiomethylsuccinyl]-L-tert-leucine-N-methylamide;

19.7: [(2R,3S)-2-Cyclopentylmethyl-3-(4-fluorobenzenesulfonyl)methyl-3-hydroxy-4-hydroxyaminosuccinyl]-L-tert-leucine-N-methylamide;

19.8: [(2R,3S)-2-Cyclopentylmethyl-3-hydroxy-4-hydroxyamino-3-(4-methoxybenzenesulfonyl)methylsuccinyl]-L-tert-leucine-N-methylamide;

19.9: [(2R,3S)-2-Cyclopentylmethyl-3-hydroxy-4-hydroxyamino-3-mercaptomethylsuccinyl]-L-tert-leucine-N-methylamide;

19.10: [(2R,3S)-3-Acetylthiomethyl-2-cyclopentylmethyl-3-hydroxy-4-hydroxyaminosuccinyl]-L-tert-leucine-N-methylamide.

EXAMPLE 20

[2R-(1-Hydroxyaminocarbonyl)cyclopropyl-4-methylpentanoyl]-L-phenylalanine-N-methylamide

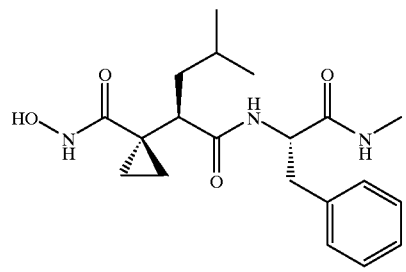

Step 1: (4-Benzhydryloxy-2R-isobutyl-3-methylenesuccinyl)-L-phenylalanine-N-methylamide (4-Hydroxy-2R-isobutyl-3-methylenesuccinyl)-L-phenylalanine-N-methylamide (2.0 g, 5.76 mmol), prepared as described in Example 4, Step 2, was dissolved in a mixture of acetonitrile (66 mL) and dichloromethane (34 mL). A solution of diphenyldiazomethane (DDM; 1.17 g, 6 mmol) in dichloromethane (20 mL) was added dropwise under stirring, and the mixture left at room temperature for 1 h. Acetic acid (0.5 mL) was added to discharge the color of excess DDM. Evaporation under reduced pressure left a residue, which was treated with diisopropyl ether. The white precipitate was collected by filtration (2.5 g, 4.88 mmol; 85%). IR (KBr), $v_{max}$ 3317, 3035, 2953, 2368, 1715, 1648, 1538 and 1455 cm$^{-1}$.

Step 2: [2R-(1-Benzhydryloxycarbonyl) cyclopropyl-4-methyl-pentanoyl]-L-phenylalanine-N-methylamide The compound from Step 1 above (500 mg, 0.976 mmol) was taken up in dichloromethane (2 mL) and ethyl ether (150 mL). To this solution, an ethereal solution of diazomethane (prepared from N-methyl-N-nitroso-p-toluenesulfonamide, 2 g, by Aldrich R Diazald$^R$ Kit) was added dropwise. The mixture was left standing overnight, then evaporated and taken up in acetonitrile (150 mL). This solution was irradiated (λ>300 nm) until complete conversion into a new product was monitored by HPLC. The solvent was evaporated under reduced pressure and the residue was purified by flash chromatography (n-hexane and ethyl acetate gradient elution) to afford the title compound as a white foam (250 mg, 0.486 mmol; 50%). IR (KBr), $v_{max}$ 3326, 3063, 3022, 2957, 1740, and 1652 cm$^{-1}$.

Step 3: [2R-(1-Carboxy)cyclopropyl-4-methylpentanoyl]-L-phenyl-alanine-N-methylamide The compound from Step 2 above (250 mg, 0.486 mmol) was taken up in ethanol (20 mL) and exposed to a hydrogen atmosphere in the presence of 10% Pd on charcoal (100 mg) for 2 h. The catalyst was removed by filtration (Celite$^R$ filter aid), washed with additional ethanol, and the combined ethanol solution was evaporated to dryness to obtain the crude title compound as a white solid.

Step 4: [2R-(1-Benzyloxyaminocarbonyl)cyclopropyl-4-methyl-pentanayl]-L-phenylalanine-N-methylamide The crude compound from Step 3 above was dissolved in a mixture of DMF (3 mL) and acetonitrile (12 mL). To this solution, O-benzylhydroxylamine hydrochloride (90 mg, 0.55 mmol), N-methylmorpholine (0.12 mL, 1.1 mmol), and O-benzotriazol-yl-N,N,N',N'-tetramethyluronium tetrafluoroborate (TBTU; 193 mg, 0.6 mmol) were added in this order. After stirring for 15 h at room temperature, the solvent was removed under reduced pressure and the residue was taken up in ethyl acetate. Sequential washing with 2N aqueous HCl, saturated aqueous sodium bicarbonate and water, followed by drying over Na$_2$SO$_4$ and evaporation, left a residue which was purified by flash chromatography over silica (n-hexane and ethyl acetate gradient elution), thereby obtaining the title compound as a white solid (55 mg, 0.12 mmol; 25% over the two steps).

Step 5: [2R-(1-Hydroxyaminocarbonyl) cyclopropyl-4-methyl-pentanoyl]-L-phenylalanine-N-methylamide A solution of the compound from Step 4 above (55 mg, 0.12 mmol) in ethanol (5 mL) was exposed to a hydrogen atmosphere in the presence of 5% Pd on barium sulfate (30 mg) for 2.5 h. The catalyst was removed by filtration (Celite$^R$ filter aid), washed with additional ethanol, and the combined ethanol solution was evaporated to dryness. The residue was triturated with ethyl ether, and the resulting white powder was collected by filtration (20 mg; 0.053 mmol; 44%). IR (KBr), $v_{max}$ 3380, 2958, 1654, and 1660 cm$^{-1}$. $^1$H NMR (400 MHz, DMSO-d$_6$): 0.18, 0.43, 0.54 and 0.98 (each m, 4H, cyclopropyl —CH$_2$—CH$_2$), 0.77 and 0.78 (each d, J=6.8 Hz, 6H, 2×Me), 1.16 and 1.68 (each m, 2H, CH$_2$CHMe$_2$), 1.33 (m, 1H, CH$_2$CHMe$_2$), 2.09 (dd, J=4.7 and 10.3 Hz, 1H, CH-iBu), 2.55 (d, J=4.7 Hz, 3H, CONHCH$_3$), 2.75 and 2.94 (each m, 2H, Phe methylene), 4.50 (m, 1H, CONHCH), 7.1–7.3 (m, 5H, Ph), 7.97 (q, J=4.7 Hz, 1H, CONHCH$_3$), 8.47 (d, J=9.0 Hz, 1H, CONHCH), 8.62 (5, 1H, CONHOH), and 10.97 ppm (s, 1H, CONHOH).

EXAMPLE 21

[2R-[(2S)-2-Carboxy-2-oxiranyl]-4-methylpentanoyl]-L-phenyl-alanine-N-methylamide

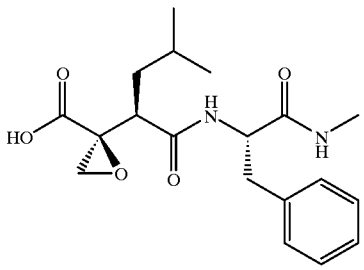

[2R-[(2S)-2-Benzhydryloxycarbonyl-2-oxiranyl]-4-methyl-pentanoyl]-L-phenylalanine-N-methylamide (25 mg, 0.047 mmol), prepared as described in Example 18, Step 1, was dissolved in ethanol (5 mL) and exposed to a hydrogen atmosphere in the presence of 10% Pd on charcoal (10 mg) for 2 h. The catalyst was removed by filtration (Celite$^R$ filter aid), washed with additional ethanol, and the combined ethanol solution was evaporated to dryness. The residue was triturated with ethyl ether, and the resulting white solid was collected by filtration (15 mg, 0.041 mmol; 87%). $^1$H NMR (400 MHz, DMSO-d$_6$): 0.67 and 0.70 (each d, J=6.4 Hz, 6H, 2×Me), 0.95–1.30 (m, 3H, CH$_2$CHMe$_2$), 2.21 and 2.55 (each d, J=6.0 Hz, 2H, oxirane methylene), 2.51 (d, J=4.7 Hz, 3H, CONHCH$_3$), 2.74 (dd, J=13.6 and 10.0 Hz, 1H, CH—CHH—Ph), 2.82 (m, 1H, CH-iBu), 2.96 (dd, J=13.6 and 4.7 Hz, 1H, CH—CHH—Ph), 4.30 (m, 1H, CONHCH), 7.1–7.3 (m, 5H, Ph), 7.90 (m, 1H, CONHCH$_3$), and 8.60 ppm (m, 1H, CONHCH).

EXAMPLE 22

1-[(2R,3S)-3-Benzoyoloxymethyl-3-hydroxy-4-hydroxyamino-2-isobutylsuccinyl]morpholine

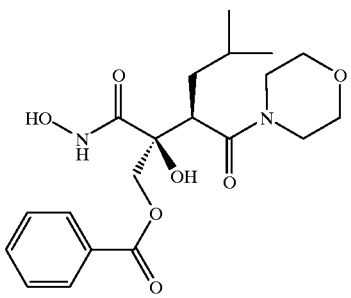

Step 2: 1-[(2R,3S)-4-Benzyloxy-3-benzoyloxymethyl-3-hydroxy-2-isobutylsuccinyl]morpholine (2R,3S)-(4-Benzyloxy-3-benzoyloxymethyl-3-hydroxy-2-isobutyl)-succinic acid (1.15 g, 2.77 mmol), obtained as described in Preparation 5, was dissolved in a mixture of dry DMF (8 mL) and dichloromethane (12 mL). To this solution, N-methyl-morpholine (0.39 mL), HOBT (1-hydroxybenzotriazole hydrate; 478 mg), and 1-(3-dimethylaminopropyl)-3-ethylcarbodiimide hydrochloride (670 mg) were added at 0° C. After 75 min, morpholine (0.15 mL) was added, and the reaction mixture was left for 20 hr at room temperature. The solution was taken up in ethyl acetate, and sequentially washed with 2% aqueous HCl, saturated aqueous sodium bicarbonate, and brine. After drying over Na$_2$SO$_4$, the solvent was removed and the residue was purified by flash-chromatography, thereby obtaining the title product as an oil (960 mg, 1.99 mmol; 72%).

Step 2: 1-[(2R,3S)-3-Benzoyloxymethyl-1,4-dihydroxy-2-isobutyl-succinyl]morpholine A solution of the compound from Step 1 above (957 mg; 1.98 mmol) in ethanol (35 mL) was exposed to a hydrogen atmosphere in the presence of 5% Pd on charcoal (450 mg) for 2 hr. The catalyst was filtered off, washed with ethanol, and the combined solution was evaporated to dryness. The residue was taken up in ethyl ether and concentrated to obtain the title product as a white powder (750 mg, 96%).

Step 3: 1-[(2R,3S)-4-Benzyloxyamino-3-benzoyloxymethyl-3-hydroxy-2-isobutylsuccinyl]morpholine A solution in acetonitrile (30 mL) of the compound from Step 2 above (750 mg, 1.91 mmol) was allowed to react with O-benzylhydroxylamine hydrochloride (335 mg, 2.01 mmol), N-methylmorpholine (0.46 mL, 4.2 mmol), and O-benzotriazolyl-N,N,N',N'-tetramethyluronium tetrafluoroborate (TBTU; 735 mg, 2.3 mmol). After 16 hr at room temperature, the solvent was removed under reduced pressure and the residue was taken up in ethyl acetate. Sequential washing with 2N aqueous HCl, saturated aqueous sodium bicarbonate and water, followed by drying over Na$_2$SO$_4$ and evaporation, left a residue (800 mg) which was purified by flash chromatography over silica (n-hexane and ethyl acetate gradient elution), thereby obtaining the pure title product (504 mg, 1.01 mmol; 53%).

Step 4: 1-[(2R,3S)-3-Benzoyloxymethyl-3-hydroxy-4-hydroxyamino -2-isobutylsuccinyl]morpholine A solution of the compound from Step 3 above (500 mg; 1 mmol) in ethanol (40 mL) was exposed to a hydrogen atmosphere in the presence of 5% Pd on charcoal (167 mg) for 3 hr. The catalyst was filtered off, washed with ethanol, and the combined solution was filtered through a Millipore$^R$ membrane. After evaporation to dryness, the residue was taken up in ethyl ether and concentrated to obtain the title product as a white solid (340 mg, 0.83 mmol; 83%). $^1$H NMR (400 MHz, DMSO-d$_6$): 0.81 and 0.82 (each d, J=6.0 Hz, 6H, 2×Me), 1.22 and 1.78 (each m, 2H, C$\underline{H}_2$CHMe$_2$), 1.30 (m, 1H, CH$_2$C$\underline{H}$Me$_2$), 3.30 (obscured by water, 1H, C$\underline{H}$-iBu), 3.40–3.60 (m, 8H, morpholino), 4.29 and 4.33 (each d, J=10.7 Hz, CH$_2$OCOPh), 5.73 (s, 1H, tertiary OH), 7.51 (m, 2H, meta-benzoyl protons), 7.65 (m, 1H, para-benzoyl proton), 7.92 (m, 2H, ortho-benzoyl protons), 8.85 (s, 1H, NHO$\underline{H}$), and 10.65 ppm (s, 1H, N$\underline{H}$OH).

EXAMPLE 23
1-[(2R,3S)-3-Acetoxymethyl-3-hydroxy-4-hydroxyamino-2-isobutylsuccinyl]piperidine

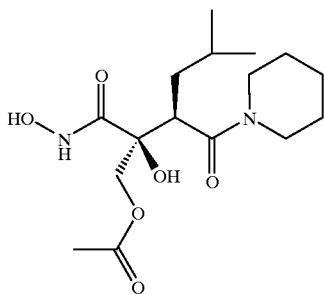

The title compound was obtained obtained starting from (2R,3S)-(3-acetoxymethyl-4-benzyloxy-3-hydroxy-2-isobutyl) succinic acid (see Preparation 4), by following the procedure described in Example 22 above but replacing morpholine with piperidine. $^1$H NMR (400 MHz, DMSO-d$_6$): 0.77 and 0.78 (each d, J=6.8 Hz, 6H, 2×Me), 1.05 and 1.65 (each m, 2H, C$\underline{H}_2$CHMe$_2$), 1.23 (m, 1H, CH$_2$C$\underline{H}$Me$_2$), 1.3–1.6 (m, 6H, piperidine 3,4,5-methylene protons), 1.92 (s, 3H, COCH$_3$), 3.21 (dd, J=3.0 and 11.1 Hz, 1H, C$\underline{H}$-iBu), 3.50 (m, 4H, piperidine 2,6-methylene protons), 3.92 and 4.00 (each d, J=11.1 Hz, 2H, CH$_2$OCO), 5.65 (s, 1H, tertiary OH), 8.75 (s, 1H, NHO$\underline{H}$), and 10.48 ppm (s, 1H, N$\underline{H}$OH).

EXAMPLE 24
1-[(2R,3S)-3-Hydroxy-4-hydroxyamino-3-hydroxymethyl-2-isobutyl-succinyl]piperidine

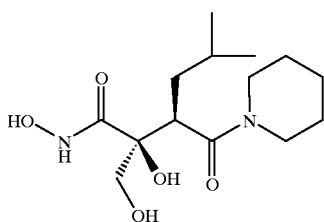

ROUTE A
Steps 1–3: 1-[(2R,3S)-(3-Acetoxymethyl-4-benzyloxyamino-3-hydroxy-2-isobutyl)succinyl]piperidine The title compound was obtained starting from (2R,3S)-(3-acetoxymethyl-4-benzyloxy-3-hydroxy-2-isobutyl) succinic acid (see Preparation 4), and following the first 3 steps of the preparation of Example 23.

Step 4: 1-[(2R,3S)-4-Benzyloxyamino-3-hydroxy-3-hydroxymethyl -2-isobutyl)succinyl]piperidine A solution of the compound from Step 3 above (600 mg) in methanol (40 mL) was allowed to react with sodium methoxide (112 mg) for 2 hr at room temperature. After quenching with acetic acid (0.16 mL), the reaction mixture was partitioned between ethyl acetate and water. Drying of the organic extract with sodium sulfate and evaporation left the crude title compound as a white solid (540 mg).

Step 5: 1-[(2R,3S)-3-Hydroxy-4-hydroxyamino-3-hydroxymethyl-2-isobutyl-succinyl]piperidine A solution of the compound from Step 4 above (540 mg) in ethanol (40 mL) was exposed to a hydrogen atmosphere in the presence of 5% Pd/C (175 mg) for 90 min at room temperature. Filtration of the catalyst and evaporation to dryness afforded the title compound as a gummy solid (350 mg). $^1$H NMR (400 MHz, DMSO-d$_6$): 0.76 and 0.77 (each d, J=6.4 Hz, 6H, 2×Me), 1.02 and 1.65 (each m, 2H, C$\underline{H}_2$CHMe$_2$), 1.20 (m, 1H, CH$_2$C$\underline{H}$Me$_2$), 1.3–1.6 (m, 6H, piperidine 3,4,5-methylene protons), 3.20 (m, 2 H, C$\underline{H}$-iBu and C$\underline{H}$(H)OH), 3.3–3.5 (m, 5H, piperidine 2,6-methylene protons and CH($\underline{H}$)OH), 4.63 (broad s, 1H, CH$_2$O$\underline{H}$), 5.38 (s, 1H, tertiary OH), 8.63 (broad s, 1H, NHO$\underline{H}$), and 10.20 ppm (brod s, 1H, N$\underline{H}$OH).

ROUTE B

A solution in dry DMF of (2R,3S)-(3-benzyloxyaminocarbonyl-3-hydroxy-2-isobutyl) butyrolactone (400 mg, obtained as described in Preparation 8) was allowed to react with piperidine (0.5 mL) for 2 days. The reaction mixture was partitioned between ethyl acetate and 4% aqueous HCl. After washing with saturated sodiun hydrogen carbonate and drying over sodium sulfate, the solvent was removed in vacuo and the residue purified by flash-chromatography over silica, thereby obtaining 1-[(2R,3S)-(4-benzyloxyamino-3-hydroxy-3-hydroxy methyl-2-isobutyl) succinyl]piperidine, identical with the material obtained by Route A, Step 4. Hydrogenolysis of this compound, as described in Step 5, Route A, afforded the title compound.

EXAMPLE 25
1-[(2R,3S)-3-Hydroxy-4-hydroxyamino-2-isobutyl-3-(trimethyl-acetoxy)methylsuccinyl]morpholine

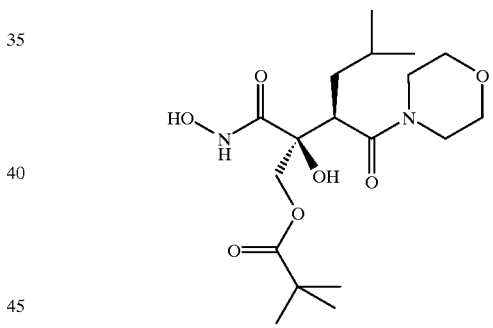

Step 1: 1-[(2R,3S)-4-Benzyloxy-3-hydroxy-2-isobutyl-3-(tri-methylacetoxy)methylsuccinyl]morpholine N-Methylmorpholine (0.382 mL) and HOBT (465 mg) were added to a solution in dichloromethane (12 mL) of (2R,3S)-[4-benzyloxy-3-hydroxy-2-isobutyl-3-(trimethylacetoxy)methyl]succinic acid (1.13 g), obtained as described in Example 13, Step 1. After cooling to 0° C., N,N-dimethylaminopropyl-N'-ethylcarbodiimide hydrochloride (660 mg) was added, followed after 75 min at 0° C. by morpholine (0.5 mL). The reaction mixture was left standing for 2 days at room temperature. The solution was taken up in ethyl acetate, and sequentially washed with 2% aqueous HCl, saturated aqueous sodium bicarbonate, and brine. After drying over Na$_2$SO$_4$, the solvent was removed and the residue was purified by flash-chromatography, thereby obtaining the title product as a yellowish oil (1.28 g).

Step 2: 1-[(2R,3S)-3,4-Dihydroxy-2-isobutyl-3-(trimethyl-acetoxy)methylsuccinyl]morpholine A solution of the compound from Step 1 above (1.25 g) in ethanol (40 mL) was exposed to a hydrogen atmosphere in the presence of 5% Pd on charcoal (0.5 g) for 2 hr. The catalyst was filtered off, washed with ethanol, and the combined solution was evaporated to dryness. The residue was taken up in ethyl ether and concentrated to obtain the title product as a gummy solid (970 mg).

Step 3: 1-[(2R,3S)-4-Benzyloxyamino-3-hydroxy-2-isobutyl-3-(trimethyl) acetoxymethylsuccinyl]morpholine A solution in acetonitrile (30 mL) of the compound from Step 2 above (950 mg) was allowed to react with O-benzylhydroxylamine hydrochloride (456 mg), N-methylmorpholine (0.62 mL), and TBTU (735 mg). After 40 hr at room temperature, the solution was concentrated under reduced pressure to a small volume and partitioned between ethyl acetate and water. Sequential washing with 2N aqueous HCl, saturated aqueous sodium bicarbonate and water, followed by drying over $Na_2SO_4$ and evaporation, left a residue (800 mg) which was purified by flash chromatography over silica (n-hexane and ethyl acetate gradient elution), thereby obtaining the pure title product (580 mg) as a white powder.

Step 4: 1-[(2R,3S)-3-Hydroxy-4-hydroxyamino-2-isobutyl-3-(trimethylacetoxy)methylsuccinyl]morpholine A solution of the compound from Step 3 above (580 mg) in ethanol (40 mL) was exposed to a hydrogen atmosphere in the presence of 5% Pd on charcoal (275 mg) for 2 hr. The catalyst was filtered off, washed with ethanol, and the combined solution was evaporated to dryness. The residue was triturated in a small volume of ethyl ether to obtain the title product as a white solid (460 mg). H NMR (400 MHz, DMSO-$d_6$): 0.78 and 0.80 (each d, J=6.5 Hz, 6H, 2×Me), 1.09 (s, 9H, t-Bu), 1.0–1.8 (m, 3H, C$\underline{H}_2$CHMe$_2$), 3.3 (obscured by water, 1H, C$\underline{H}$-iBu), 3.57 (m, 8H, morpholino), 4.00 and 4.08 (each d, J=11.0 Hz, CH$_2$OCO), 5.43 (s, 1H, tertiary OH), 8.75 (s, 1H, NHO$\underline{H}$), and 10.43 ppm (s, 1H, N$\underline{H}$OH).

EXAMPLE 26

Similarly, the following compounds may be prepared:

26.1: 1-[2(2(R)-Cyclopentylmethyl-3-hydroxy-4-hydroxyamino-3-hydroxymethylsuccinyl]piperidine;

26.2: 1-[2(R)-Cyclopentylmethyl-3-hydroxy-4-hydroxyamino-3-mercaptomethylsuccinyl]piperidine;

26.3: 1-[(2R,3S)-3-Hydroxy-4-hydroxyamino-3-hydroxymethyl-2-octysuccinyl]pyridazine;

26.4: 1-[(2R,3S)-2-(3-(4-Biphenyl)propyl)-3-hydroxy-4-hydroxy-amino-3-hydroxymethylsuccinyl]-6-(N-methylcarbamoyl)-hexahydropyridazine;

26.5: 1-[(2R,3S)-3-Hydroxy-4-hydroxyamino-2-isobutyl-3-(1-methyl-1,2,3,4-tetrazol-5-yl) thiomethylsuccinyl] piperidine;

26.6: 1-[(2R,3S)-2-Cyclopentylmethyl-3-hydroxy-4-hydroxyamino-3-(4-hydroxyphenyl)thiomethylsuccinyl] piperidine;

26.7: 1-[(2R,3S)-2-Cyclopentylmethyl-3-(4-fluorobenzene-sulfonyl)methyl-3-hydroxy-4-hydroxyaminosuccinyl]piperidine;

26.8: 1-[(2R,3S)-2-Cyclopentylmethyl-3-hydroxy-4-hydroxyamino-3-(4-methoxybenzenesulfonyl) methylsuccinyl]-6-(N-methyl-carbamoyl) hexahydropyridazine;

26.9: 1-[(2R,3S)-3-(N-Cyclohexylaminocarbonyl) oxymethyl-2-cyclopentylmethyl-3-hydroxy-4-hydroxyaminosuccinyl]piperidine;

26.10: 1-[(2R,3S)-3-(N-Cyclohexylaminocarbonyl) oxymethyl-2-cyclopentylmethyl-3-hydroxy-4-hydroxyaminosuccinyl]-6-(N-methyl-carbamoyl) hexahydropyridazine;

26.11: N-[(2R,3S)-3-(N-Cyclohexylaminocarbonyl) oxymethyl-2-cyclopentylmethyl-3-hydroxy-4-hydroxyaminosuccinyl]-2-cyclohexylethylamine;

26.12: (R)-N-[(2R,3S)-3-(N-Cyclohexylaminocarbonyl) oxymethyl-2-cyclopentylmethyl-3-hydroxy-4-hydroxyaminosuccinyl]-1-cyclo-hexylethylamine;

26.13: (R)-N-[(2R,3S)-3-(N-Cyclohexylaminocarbonyl) oxymethyl-2-cyclopentylmethyl-3-hydroxy-4-hydroxyaminosuccinyl]-1-phenyl-ethylamine;

26.14: (R)-N-[(2R,3S)-3-(N-Cyclohexylaminocarbonyl) oxymethyl-2-cyclopentylmethyl-3-hydroxy-4-hydroxyaminosuccinyl]-1-benzyl-ethylamine;

26.15: (S)-N-[(2R,3S)-3-(N-Cyclohexylaminocarbonyl) oxymethyl-2-cyclopentylmethyl-3-hydroxy-4-hydroxyaminosuccinyl]-1-benzyl-2-hydroxyethylamine;

26.16: (S)-N-[(2R,3S)-2-(3-(4-Chlorophenyl)propyl)-3-(N-cyclohexylaminocarbonyl)oxymethyl-3-hydroxy-4-hydroxyamino-succinyl]-1-benzyl-2-hydroxyethylamine;

26.17: (S)-N-[(2R,3S)-3-(N-Cyclohexylaminocarbonyl) oxymethyl-2-cyclopentylmethyl-3-hydroxy-4-hydroxyaminosuccinyl]-1-(1H-imidazol-5-yl)methyl-2-hydroxyethylamine;

26.18: (S)-N-[(2R,3S)-2-(3-(4-Biphenyl)propyl)-3-hydroxy-4-hydroxyamino-3-hydroxymethylsuccinyl]-1-(1H-imidazol-5-yl)-methyl-2-hydroxyethylamine;

26.19: (S)-N-[(2R,3S)-2-(3-(4-Biphenyl)propyl)-3-(N-cyclo-hexylaminocarbonyl)oxymethyl-3-hydroxy-4-hydroxyaminosuccinyl]-1-(1H-imidazol-5-yl)methyl-2-hydroxyethylamine;

26.20: (S)-N-[(2R,3S)-2-Cyclopentylmethyl-3-hydroxy-4-hydroxy-amino-3-hydroxymethylsuccinyl]-(3,4-dihydro) carbostyril-3-amine;

26.21: (S)-N-[(2R,3S)-2-Cyclopentylmethyl-3-hydroxy-4-hydroxy-amino-3-hydroxymethylsuccinyl]-(N-methyl-3,4-dihydro)-carbostyril-3-amine;

26.22: (S)-N-[(2R,3S)-2-Cyclopentylmethyl-3-hydroxy-4-hydroxy-amino-3-hydroxymethylsuccinyl]-(6,7-dioxymethylene-N-ethyl-3,4-dihydro)carbostyril-3-amine;

26.23: (S)-N-[(2R,3S)-3-(N-Cyclohexylaminocarbonyl) oxymethyl-2-cyclopentylmethyl-3-hydroxy-4-hydroxyaminosuccinyl]-(6,7-dioxymethylene-N-ethyl-3,4-dihydro)carbostyril-3-amine.

EXAMPLE 27

Tablets containing the following ingredients may be produced in a conventional manner:

| Ingredient | Per Tablet |
| --- | --- |
| Compound of formula (I) | 25.0 mg |
| Lactose | 125.0 mg |
| Maize starch | 75.0 mg |
| Talc | 4.0 mg |
| Magnesium stearate | 1.0 mg |
| Total weight | 230.0 mg |

EXAMPLE 28

Capsules containing the following ingredients may be produced in a conventional manner:

| Ingredient | Per capsule |
| --- | --- |
| Compound of formula (I) | 50.0 mg |
| Lactose | 165.0 mg |
| Maize starch | 20.0 mg |
| Talc | 5.0 mg |
| Capsule fill weight | 240.0 mg |

Preparation of benzyl (3R)-(2-benzyloxycarbonyl-3-carboxy-5-methyl)hexanoate by optical resolution.

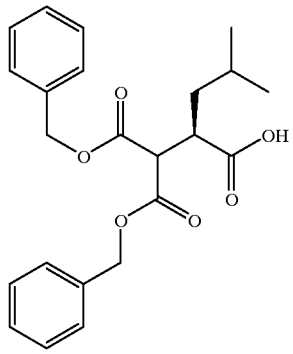

Step 1: 2-Bromo-4-methylpentanoic acid

D,L-Leucine (50 g, 0.38 mol) and potassium bromide (158.7 g, 1.33 mol) were dissolved in aqueous sulfuric acid (from 75 mL of $H_2SO_4$ and 250 mL of water), and sodium nitrite (34.8 g, 0.5 mol) was added portionwise wile keeping the temperature below –1° C. The mixture was kept at 0° C. for 1 h, then dichloromethane was added under stirring. The dichlomethane layer was collected and the aqueous phase was extracted twice with further portions of dichloromethane. The combined dichloromethane extracts were dried ($Na_2SO_4$) and evaporated to give the title compound as a pale yellow oil (63.4 g, 0.32 mol; 85.5%).

Step 2: tert-Butyl 2-bromo-4-methylpentanoate

The product from Step 1 above (63.3 g, 0.32 mol) was dissolved in dichloromethane (250 mL), concentrated sulfuric acid (2 mL) was added, and cooled to –40° C. in a pressure bottle. Isobutene was condensed into the solution to roughly double the volume, and the mixture was then allowed to warm to room temperature overnight. Following evaporation to half of the volume under reduced pressure, the solution was washed with 10% aqueous sodium bicarbonate, dried over $Na_2SO_4$, and thoroughly evaporated under reduced pressure at room temperature to leave the title compound as a yellow oil (79.9 g, 0.314 mol; 98%).

Step 3: Benzyl (2-benzyloxycarbonyl-3-tert-butoxycarbonyl-5-methyl)hexanoate

Potassium tert-butoxide (26.9 g, 0.24 mol) was added portionwise under stirring to a cooled (–5° C.) solution of dibenzyl malonate (59.3 mL, 0.24 mol) in dry DMF (100 mL). After further 10 min stirring between –5° C. and 0° C., a solution of tert-butyl 2-bromo-4-methylpentanoate (60.7 g, 0.24 mol) from Step 2 above in dry DMF (100 mL) was added dropwise over 1 h while keeping the temperature at 0° C. After the addition was complete, the reaction mixture was kept for 4 days in a cold room (4° C.), then partitioned between ethyl acetate and saturated aqueous ammonium chloride. The aqueous layer was extracted twice with further ethyl acetate before being discarded. The combined organic extracts were dried ($Na_2SO_4$) and evaporated, to left a residue which was purified by flash chromatography over silica (95:5 n-hexane and ethyl acetate). The title compound was obtained as a colourless oil (79.9 g, 0.175 mol; 73.1%). $^1$H NMR (200 MHz, $CDCl_3$): 0.83 and 0.84 (each d, J=6.5 Hz, 6H, 2×Me), 1.0–1.6 (m, 3H, $CH_2CHMe_2$), 1.39 (s, 9H, tert-Bu), 3.06 (m, 1H, $CH$-iBu), 3.74 (d, J=10.1 Hz, 1H, C$H(CO_2Bn)_2$), 5.12 (m, 4H, 2×$CO_2CH_2Ph$), and 7.30 ppm (m, 10H, 2×Ph).

Step 4: Benzyl (2-benzyloxycarbonyl-3-carboxy-5-methyl)-hexanoate

The compound from Step 3 above (72 g, 0.16 mol) was added to a solution of trifluoroacetic acid (100 mL) and water (5 mL) and allowed to stand at 4° C. overnight. After evaporation under reduced pressure, the residue was partitioned between dichloromethane (250 mL) and brine (250 mL). The organic layer was dried ($Na_2SO_4$) and evaporated to give the crude title product as a colourless oil (63.7 g, 0.16 mol; quantitative yield).

Step 5: optical resolution of Benzyl (3R)-(2-benzyloxycarbonyl-3-carboxy-5-methyl)hexanoate The racemic crude compound from Step 4 above (63.7 g, 0.16 mol) was taken up in diisopropyl ether (300 mL) and the mixture heated to reflux temperature until a homogeneous solution formed, which while hot was treated dropwise with S(–)-1-phenylethylamine (10.3 mL, 0.08 mol). The mixture was then allowed to cool to room temperature; filtration gave the phenylethylammonium salt of the title (3R) acid (36.4 g, 0.07 mol). This salt was added under stirring to a mixture of ethyl ether (250 mL) and 2N aqueous HCl (35 mL, 0.07 mol). The aqeous layer was extracted with further portions of ethyl ether, and the combined ethereal layers were dried ($Na_2SO_4$) and evaporated to give the title compound as a colourless oil which crystallized on standing (27.9 g, 0.07 mol, 87.5%). $^1$H NMR (200 MHz, DMSO-$d_6$): 0.76 (d, J=6.4 Hz, 6H, 2×Me), 1.0–1.6 (m, 3H, $CH_2CHMe_2$), 2.92 (m, 1H, $CH$-iBu), 3.70 (d, J=10.1 Hz, 1H, C$H(CO_2Bn)_2$), 5.11 (s, 2H, $CO_2CH_2Ph$), 5.12 and 5.17 (each d, J=12.3 Hz, 2H, $CO_2CH_2Ph$), 7.32 (m, 10H, 2×Ph), and 12.59 ppm (broad s, 1H, $CO_2H$).

PREPARATION 2 tert-Butyl (2R,3S)-(3,4-dihydroxy-3-hydroxymethyl-2-isobutyl)-succinate

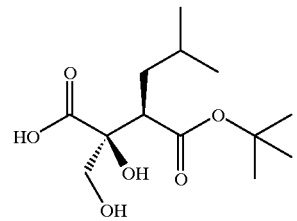

Step 1: tert-Butyl (2R)-(4-hydroxy-2-isobutyl-3-methylene)-succinate

A solution in ethanol (250 mL) of benzyl (3R)-(2-benzyloxycarbonyl-3-carboxy-5-methyl)hexanoate (60 g; 0.13 mol), obtained as described in Preparation 1, was exposed to a hydrogen atmosphere in the presence of 5% Pd on charcoal (20 g) overnight. The catalyst was filtered off, washed with ethanol, and piperidine (15 mL) and 37% aqueous formaldehyde (91 mL) were added the combined ethanol solution. After standing at 4° C. for 3 days, the reaction mixture was concentrated in vacuo, taken up with ethyl acetate, and washed with 4% aqueous HCl. After drying over $Na_2SO_4$ and evaporation, the crude title product was obtained (32 g, 0.13 mol; quantitative yield).

Step 2: tert-Butyl (2R,3S)-(3,4-dihydroxy-3-hydroxymethyl-2-isobutyl)succinate

N-Methylmorpholine—N-oxide (18.5 g, 0.159 mol) was dissolved in a mixture of water (10 mL) and acetone (5 mL), and osmium tetroxide (2.5% in tert-butanol; 13 mL, 1.32 mmol) was added. After stirring for 15 min, a solution of the crude compound from Step 1 above (32 g, 0.13 mol) in tert-butanol (300 mL) was added. After stirring for 18 h at room temperature, the solution was concentrated and the residue was taken up in ethyl acetate, washed with 4% aqueous HCl, dried over $Na_2SO_4$ and evaporated to dryness to leave a brownish oil. Addition of ethyl ether and stirring caused the separation of the pure title product, which was collected as a white powder by filtration (8.6 g). Removal of the solvent from the mother liquors gave a further crop of the title compound as a syrup (23.25; total 31.85 g, 0.116 mol; 87.9%). $^1H$ NMR (400 MHz, DMSO-$d_6$): 0.79 and 0.82 (each d, J=6.4 Hz, 6H, 2×Me), 0.95 and 1.77 (each m, 2H, C$\underline{H}_2$CHMe$_2$), 1.36 (s, 9H, t-Bu), 1.36 (m, 1H, CH$_2$C$\underline{H}$Me$_2$), 2.57 (dd, J=2.9 and 12.0 Hz, 1H, CH-iBu), 3.39 and 3.65 ppm (each d, J=10.8 Hz, 2H, C$\underline{H}_2$OH).

PREPARATION 3
tert-Butyl (2R,3S)-(4-benzyloxy-3-hydroxy-3-hydroxymethyl-2-isobutyl)succinate

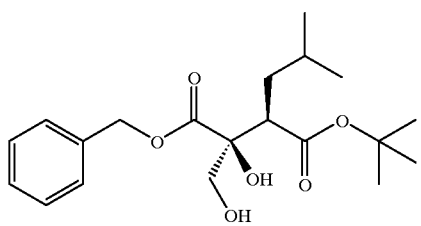

A solution) in dry DMF (210 mL) of tert-butyl (2R,3S)-(3,4-dihydroxy-3-hydroxymethyl-2-isobutyl)succinate (23.2 g, 96 mmol), obtained as described in Preparation 2, was treated at 0° C. with benzyl bromide (12.5 mL, 106 mmol) and triethylamine (14.7 mL, 106 mmol). After 15 min at 0° C., the cooling bath was removed and the mixture was stirred for 20 hr. Partition between water and ethyl acetate, followed by separation of the organic layer, sequential washing with 4% aqueous HCl, saturated aqueous sodium bicarbonate and water, drying (Na$_2$SO$_4$) and evaporation, left a residue, which was fractionated by flash chromatography over silica (4:1 hexane-ethyl acetate). The title product was obtained as the slower-eluting compound (13.5 g, 37 mmol; 38.5%). A second crop, consisting of a mixture of the same compound with the 2R,3R isomer, was also obtained (7.54 g, 20.6 mmol; 21.5%; total yield 60%). IR (CHCl$_3$ film), $v_{max}$ 2959, 2872, and 1738 cm$^{-1}$. $^1H$ NMR (400 MHz, DMSO-$d_6$): 0.67 and 0.75 (each d, J=6.6 Hz, 6H, 2×Me), 0.81 and 1.74 (each m, 2H, C$\underline{H}_2$CHMe$_2$), 1. 31 (m, 1H, CH$_2$C$\underline{H}$Me$_2$), 1.35 (s, 9H, t-Bu), 2.58 (dd, J=2.6 and 11.9 Hz, 1H, CH-iBu), 3.45 (dd, J=4.8 and 11.0 Hz, 1H, C$\underline{H}$(H)OH), 3.70 (dd, J=6.8 and 11.0 Hz, 1H, CH($\underline{H}$)OH), 4.90 (dd, J=4.8 and 6.8 Hz, 1H, primary OH), 5.01 (s, 1H, tertiary OH), 5.11 and 5.16 (each d, J=12.5 Hz, 2H, COOC$\underline{H}_2$Ph), and 7.36 ppm (m, 5H, Ph).

PREPARATION 4
(2R,3S)-(3-Acetoxymethyl-4-benzyloxy-3-hydroxy-2-isobutyl)-succinic acid

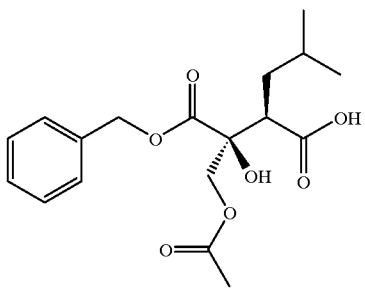

Step 1: tert-Butyl (2R,3S)-(3-acetoxymethyl-4-benzyloxy-3-hydroxy-2-isobutyl)succinate tert-Butyl (2R,3S)-(4-benzyloxy-3-hydroxy-3-hydroxymethyl-2-isobutyl)succinate (2.1 g, 5.75 mmol), obtained as described in Preparation 3, was dissolved in dichloromethane (80 mL). Pyridine (0.92 mL, 11.5 mmol) and then acetyl chloride (0.81 mL, 11.5 mmol) was added dropwise at 0° C. The cooling bath was removed and the solution was left for 5 hr under stirring. Sequential washing with 4% aqueous HCl, saturated aqueous sodium bicarbonate and water, drying (Na$_2$SO$_4$) and evaporation, left the title product (essentially pure by HPLC; 2.16 g, 5.3 mmol; 92.2%).

Step 2: (2R, 3S)-(3-Acetoxymethyl-4-benzyloxy-3-hydroxy-2-isobutyl)succinic acid Trifluoroacetic acid (2.3 mL) was added to a cooled (0° C.) solution of the compound from Step 1 above (2.16 g, 5.3 mmol) in dichloromethane (5 mL). The cooling bath was removed, and the mixture was stirred overnight. The solution was repeatedly evaporated in vacuo after repeated addition of ethyl ether, thereby obtaining the crude title compound as an oil (1.87 g, 5.3 mmol; quantitative yield).

PREPARATION 5
(2R,3S)-(4-Benzyloxy-3-benzoyloxymethyl-3-hydroxy-2-isobutyl)-succinic acid

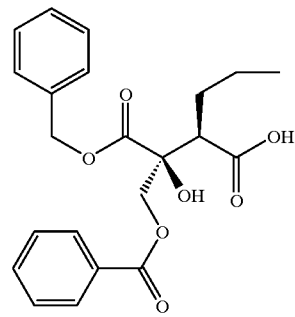

Step 1: tert-Butyl (2R,3S)-(4-benzyloxy-3-benzoyloxymethyl-3-hydroxy-2-isobutyl)succinate A solution in dry dichloromethane (30 mL) of tert-butyl (2R,3S)-(4-benzyloxy-3-hydroxy-3-hydroxymethyl-2-isobutyl)-succinate (1.83 g, 5 mmol), obtained as described in Preparation 3, was sequentially treated at 0° C. with benzoyl chloride (0.7 mL, 6 mmol) and triethylamine (0.84 mL, 6 mmol). The solution was left aside for 20 hr at room temperature. Aqueous work-up (washing with sodium bicarbonate and diluted HCl) and flash chromatography afforded the title compound as a white powder (1.4 9, 3 mmol; 60%).

Step 2: (2R,3S)-(4-Benzyloxy-3-benzoyloxymethyl-3-hydroxy-2-isobutyl)succinic acid The compound from Step 1 above (1.4 g, 3 mmol) was dissolved in dichloromethane (10 mL) and treated with trifluoroacetic acid (4 mL). After 2 hr at room temperature, the reaction mixture was evaporated to dryness, and the residue was triturated with isopropyl ether and filtered, thereby obtaining the title compound as a white powder (550 mg). A second crop (600 mg) was recovered from the mother liquors by evaporation and flash-chromatography over silica (n-hexane and ethyl acetate as eluants). Total yield 1.15 g (2.8 mmol; 92%). $^1$H NMR (200 MHz, CDCl$_3$): 0.77 and 0.84 (each d, J=6.4 Hz, 6 H, 2×Me), 0.92 and 1.90 (each m, 2H, C$\underline{H}_2$CHMe$_2$), 1.51 (m, 1H, CH$_2$C$\underline{H}$Me$_2$), 3.03 (dd, J=3.2 and 11.9 Hz, 1H, CH-iBu), 4.58 (s, 2H, C$\underline{H}_2$OCOPh), 5.23 and 5.30 (each d, J=11.7 Hz, 2H, COOC$\underline{H}_2$Ph), and 7.2–7.9 ppm (m, 10H, Ph).

PREPARATION 6
(2R,3S)-(2-Benzyl-3-carboxy-3-hydroxy)butyrolactone

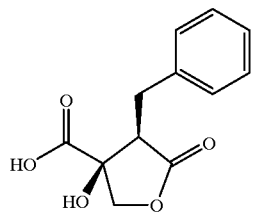

Trifluoroacetic acid (2 mL) was added to a solution of tert-butyl (2R,3S)-(2-benzyl-3,4-dihydroxy-3-hydroxymethyl) succinate (300 mg; 1.02 mmol) in dichloromethane (6 mL). After 3 hr at room temperature, the mixture was concentrated in vacuo to leave a residue. Trituration with isopropyl ether and filtration gave the title product as a white powder (180 mg, 0.76 mmol; 75%). $^1$H NMR (200 MHz, DMSO-d$_6$): 2.82 (m, 2H, C$\underline{H}_2$Ph), 3.30 (m, 1H, C$\underline{H}$CH$_2$Ph), 4.11 and 4.28 (each d, J=9.4 Hz, 2H, lactone methylene), 6.10 (broad s, 1H, OH), 7.17 (m, 5H, Ph), and 13.00 ppm (broad s, 1H, COOH).

PREPARATION 7
(2R,3S)-(2-Benzyl-3-benzyloxyaminocarbonyl-3-hydroxy)-butyrolactone

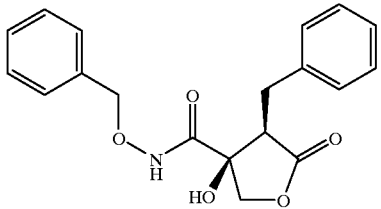

By following a procedure analogous to that described in Example 2, Step 1, a solution in acetonitrile (10 mL) of (2R,3S)-(2-benzyl-3-carboxy-3-hydroxy)butyrolactone (110 mg, 0.46 mmol), obtained as described in Preparation 6, was allowed to react with O-benzylhydroxylamine hydrochloride (88 mg), N-methylmorpholine (0.12 mL), and O-benzotriazolyl-N,N,N',N'-tetramethyluronium tetrafluoroborate (TBTU; 190 mg). After 2 days at room temperature, work-up and flash chromatography over silica afforded the title product as a white powder (85 mg, 0.25 mmol; 54%). $^1$H NMR (400 MHz, DMSO-d$_6$): 2.77 (dd, J=9.0 and 14.5 Hz, 1H, C$\underline{H}$(H)Ph), 2.86 (dd, J=4.7 and 14.5 Hz, 1H, CH(H)Ph), 3.38 (dd, J=4.7 and 9.0 Hz, 1 H, C$\underline{H}$CH$_2$Ph), 4.18 and 4.31 (each d, J=9.8 Hz, 2H, lactone methylene), 4.15 and 4.23 (each d, J=10.2 Hx, 2H, OC$\underline{H}_2$Ph), 6.53 (s, 1H, OH), 7.0–7.3 (m, 10H, 2×Ph), and 11.31 ppm (s, 1H, CONHO).

PREPARATION 8
(2R,3S)-(3-Benzyloxyaminocarbonyl-3-hydroxy-2-isobutyl)-butyrolactone

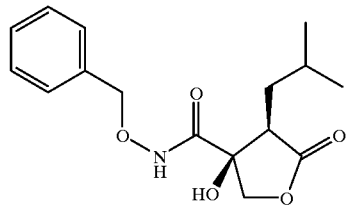

Starting from tert-butyl (2R,3S)-(3,4-dihydroxy-3-hydroxy-methyl-2-isobutyl)succinate (0.6 g), obtained as described in Preparation 2, and using identical procedures to those described in Preparation 6 and Preparation 7, in this order, the title compound was obtained as a white powder (0.3 g).

PREPARATION 9

(2R,3S)-(3-Acetoxymethyl-3-benzyloxycarbonyl-2-isobutyl)-propiolactone

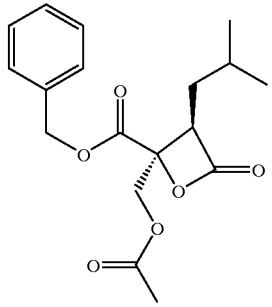

A solution in dichloromethane (10 mL) of (2R,3S)-(3-acetoxymethyl-4-benzyloxy-3-hydroxy-2-isobutyl)succinic acid, (210 mg), obtained as described in Preparation 4, was allowed to react with N,N-dimethylaminopropyl-N'-ethylcarbodiimide hydrochloride (120 mg) for 15 hr at room temperature. The i reaction mixture was washed with water and evaporated to leave the crude title product as a waxy solid in quantitative yield. An analytical sample was obtained by flash chromatography over silica. IR (CHCl$_3$ film), $v_{max}$ 1831, 1772, and 1713 cm$^{-1}$. $^1$H NMR (400 MHz, DMSO-d$_6$): 0.74 and 0.78 (each d, J=6.7 Hz, 6H, 2×Me), 1.26 (m, 2H, C$\underline{H}_2$CHMe$_2$), 1.56 (m, 1H, CH$_2$C$\underline{H}$Me$_2$), 1.95 (s, 3H, COMe), 4.15 (dd, J=6.3 and 9.0 Hz, 1H, CH-iBu), 4.54 and 4.69 (each d, J=12.8 Hz, 2H, C$\underline{H}_2$OAc), 5.27 and 5.32 (each d, J=12.1 Hz, 2H, COOCH$_2$Ph), and 7.38 ppm (m, 5H, Ph).

What is claimed is:

1. A compound of formula (I)

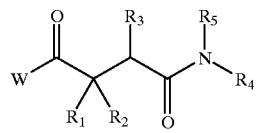

(I)

wherein

W is —NHOH or —OH;

R₁ is hydroxymethyl or a hydroxymethyl derivative which is an ether, an ester, a carbonate or a carbamate; or R₁ is mercaptomethyl or a mercaptomethyl derivative which is a sulfide, a sulfoxide, a sulfone or a thioester;

R₂ is hydroxy or protected hydroxy; or

R₁ and R₂, taken together with the carbon atom to which they are attached, represent an optionally substituted cyclopropane, oxirane, 1,3-dioxolane or 2-oxo-1,3-dioxolane ring of the following formulae (B1)–(B4):

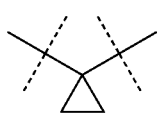

(B1)

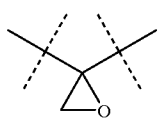

(B2)

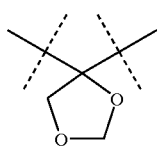

(B3)

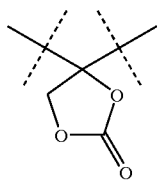

(B4)

R₃ is a group —A^I—X—(CH₂)ₙ—A, wherein A is C₁–C₁₀ alkyl, C₂–C₁₀ alkenyl, C₃–C₇ cycloalkyl, aryl, or heterocyclyl, the said alkyl, alkenyl, cycloalkyl, aryl and heterocyclyl groups being unsubstituted or substituted; n is either zero or an integer from 1 to 5; —X— is either a direct bond or a group —O—, —S—, —SO—, —SO₂—, —SO₂NH—, —CO—, —CONH—, —NHCO—, —OCONH—, NHCONH or —NHSO₂—, and —A^I— is C₁–C₁₀ alkylene, C₂–C₆ alkenylene, or phenylene;

R₄ is a group of formula (C):

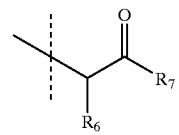

(C)

wherein R₆ is hydrogen or the side chain of a natural or non-natural alpha-amino acid, and R₇ is amino or a group —NH—A, —NH—CH₂—A or —NH—CH₂CH₂—A wherein A is as defined above; or R₄ is a group A as defined above or a group —A^I—X—A wherein A, —X— and —A^I— are as defined above;

or R₄ is a group of formula (D):

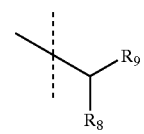

(D)

wherein R₈ is methyl, ethyl, phenyl, pyridyl, isopropyl, sec-butyl, tert-butyl, adamantyl, cylclopentyl, cyclohexyl, cyclohexylmethyl, phenylmethyl, 3,4-(methylenedioxy)phenyl, piperonyl, pyridylmethyl, thienylmethyl, 3-indolylmethyl, 3-(N-methyl)indolylmethyl, 1,1-diphenylmethyl, naphthyl, naphthylmethyl, quinolylmethyl, isoquinolylmethyl, thiazolyl, thiazolylmethyl, imidazolyl, imidazolylmethyl, or a derivative thereof optionally substituted, or R₈ is —C(CH₃)₂SCH₃ or a sulfoxide or sulfone thereof, —C(CH₃)₂OCH₃, —CH₂CH₂CH₂—OCH₃, or —CH(CH₃)OH or a tert-butyl ether thereof; R₉ is either hydrogen or a group selected from methyl, ethyl, phenyl, 3,4-(methylenedioxy)phenyl, piperonyl, pyridyl, benzimidazolyl and 4-tetrazolyl, which group is optionally substituted; or R₈ and R₉, taken together with the nitrogen atom to which they are attached, constitute a dihydrocarbostyril ring (D'):

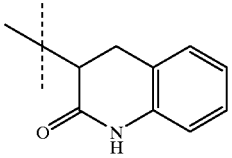

(D')

wherein the nitrogen atom and the phenyl ring may be optionally substituted;

R₅ is hydrogen or methyl; or

R₄ and R₅, taken together with the nitrogen atom to which they are attached, form an optionally substituted aza-heterocyclyl ring;

and the solvates, hydrates and pharmaceutically acceptable salts thereof.

2. A compound according to claim 1 wherein the absolute stereochemistry of the succinic amide carbon atoms is the one of the formula (I'):

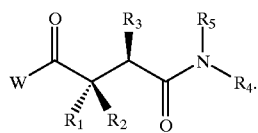

(I')

3. A compound according to claim 2 wherein:

W is —NHOH or —OH;

$R_1$ is hydroxymethyl or the ether, ester, carbonate and carbamate derivates thereof, as defined above; or $R_1$ is a mercaptomethyl or the sulfide, sulfone and thioester derivatives thereof, as defined above;

$R_2$ is hydroxy or a protected derivative thereof; or $R_1$ and $R_2$, taken together with the carbon atom to which they are attached, form a cyclopropane or oxirane ring, optionally substituted by phenyl or benzyl; and:

$R_3$ is —$CH_2$-alkyl, —$CH_2$-cycloalkyl, —$(CH_2)_n$—O-alkyl, —$(CH_2)_n$—O-cycloalkyl, —$(CH_2)_n$—O—$(CH_2)_{n'}$-aryl, —$(CH_2)_n$—O—$(CH_2)_{n'}$-heterocyclyl, —$(CH_2)_n$—S-alkyl, —$(CH_2)_n$—S-cycloalkyl, —$(CH_2)_n$—S—$(CH_2)_{n'}$-aryl, —$(CH_2)_n$—S—$(CH_2)_{n'}$-heterocyclyl, —$(CH_2)_n$—S(O)-alkyl, —$(CH_2)_n$—S(O)-cycloalkyl, —$(CH_2)_n$—$SO_2$-alkyl, —$(CH_2)_n$—$SO_2$-cycloalkyl, —$(CH_2)_n$—$SO_2$—$(CH_2)_{n'}$-aryl, —$(CH_2)_n$—$SO_2$—$(CH_2)_{n'}$-heterocyclyl, —$(CH_2)_n$—$SO_2$NH-alkyl, —$(CH_2)_n$—$SO_2$NH-cycloalkyl, —$(CH_2)_n$—$SO_2$NH—$(CH_2)_{n'}$-aryl, —$(CH_2)_n$—$SO_2$NH—$(CH_2)_{n'}$-heterocyclyl, —$(CH_2)_n$—CO-alkyl, —$(CH_2)_n$—CO-cycloalkyl, —$(CH_2)_n$—CO—$(CH_2)_{n'}$-aryl, —$(CH_2)_n$—CO—$(CH_2)_{n'}$-heterocyclyl, —$(CH_2)_n$—CONH-alkyl, —$(CH_2)_n$—CONH-cycloalkyl, —$(CH_2)_n$—CONH—$(CH_2)_{n'}$-aryl, —$(CH_2)_n$—CONH—$(CH_2)_{n'}$-heterocyclyl, —$(CH_2)_n$—NHCO-alkyl, —$(CH_2)_n$—NHCO-cycloalkyl, —$(CH_2)_n$—NHCO—$(CH_2)_{n'}$-aryl, —$(CH_2)_n$—NHCO—$(CH_2)_{n'}$-heterocyclyl, —$(CH_2)_n$—$NHSO_2$-alkyl, —$(CH_2)_n$—$NHSO_2$-cycloalkyl, —$(CH_2)_n$—$NHSO_2$—$(CH_2)_{n'}$-aryl or —$(CH_2)_n$—$NHSO_2$—$(CH_2)_{n'}$-heterocyclyl, wherein the said alkyl, cycloalkyl, aryl and heterocyclyl groups are unsubstituted or substituted by one to three substituents selected from chloro, fluoro, hydroxy, methoxy, and $C_1$–$C_4$ alkyl; and n and n, being the same or different, are zero or an integer from 1 to 5, and $R_4$, $R_5$ are as defined above.

4. A compound according to claim 2 wherein W, $R_1$, $R_2$ and $R_3$ are as defined above;

$R_4$ is a group of formula (C):

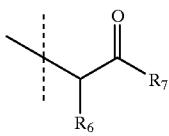

(C)

wherein $R_6$ is phenyl, pyridyl, isopropyl, sec-butyl, tert-butyl, adamantyl, cylclopentyl, cyclohexyl, cyclohexylmethyl, phenylmethyl, -pyridylmethyl, 3-pyridylmethyl, 4-pyridylmethyl, 2-thienylmethyl, 3-indolylmethyl, 3-(N-methyl)indolylmethyl, 1,1-diphenylmethyl, 1-naphthyl, 2-naphthyl, 1-naphthylmethyl, 2-naphthylmethyl, quinolylmethyl or isoquinolylmethyl, or a derivative thereof substituted by one to three substituents selected from chloro, fluoro, hydroxy, methoxy, carbamoyl and $C_1$–$C_4$ alkyl; or $R_6$ is —$C(CH_3)_2SCH_3$ or a sulfoxide or sulfone thereof, —$C(CH_3)_2OCH_3$, —$CH_2CH_2CH_2$—$OCH_3$, or —$CH(CH_3)OH$ or the tert-butyl ether thereof; and wherein $R_7$ is —$NH_2$ or a group —NH—A—, NH—$CH_2$—A or NH—$CH_2CH_2$—A, wherein A, being as defined above, is selected from methyl, isopropyl, tert-butyl, phenyl, 4-methoxyphenyl, 4-fluorophenyl, 4-(aminosulfonyl)phenyl, 4-(dimethylamino-sulfonylmethyl)phenyl, (3,4-methylenedioxy)phenyl, 2-pyridyl, 3-pyridyl, 4-pyridyl, 4-piperidyl, 2-thiazolyl, 1-naphthyl, 2-naphthyl, 3-quinolyl, 5-quinolyl, 3-isoquinolinyl, 5-isoquinolyl, 3-quinuclidinyl, 2-benzimidazolyl, 5-tetrazolyl, cyclopropyl, cyclobutyl, cyclopentyl, cyclohexyl, 1-morpholino, 1-piperidino, or 1-pyrrolidino; and $R_5$ is hydrogen or methyl.

5. A compound according to claim 2 wherein:

wherein W, $R_1$, $R_2$ and $R_3$ are as defined above, $R_4$ is a group of formula (D):

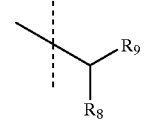

(D)

wherein $R_8$ is methyl, ethyl, phenyl, pyridyl, isopropyl, sec-butyl, tert-butyl, adamantyl, cyclopentyl, cyclohexyl, cyclohexylmethyl, phenylmethyl, 3,4-(methylenedioxy)phenyl, piperonyl, pyridylmethyl, thienylmethyl, 3-indolylmethyl, 3-(N-methyl) indolylmethyl, 1,1-diphenylmethyl, naphthyl, naphthylmethyl, quinolylmethyl, isoquinolylmethyl, thiazolyl, thiazolylmethyl, imidazolyl, imidazolylmethyl, or a derivative thereof substituted by one to three substituents selected from chloro, fluoro, hydroxy, methoxy, and $C_1$–$C_4$ alkyl; or $R_8$ is —$C(CH_3)_2SCH_3$ or a sulfoxide or sulfone thereof, —$C(CH_3)_2OCH_3$, —$CH_2CH_2CH_2$—$OCH_3$, or —$CH(CH_3)OH$ or a tert-butyl ether thereof; and $R_9$ is either hydrogen or a group selected from methyl, ethyl, phenyl, 3,4-(methylenedioxy)phenyl, piperonyl, pyridyl, benzimidazolyl and 4-tetrazolyl, which group is unsubstituted or substituted by one to three substituents selected from chloro, fluoro, hydroxy, methoxy, methoxycarbonyl, ethoxycarbonyl and $C_1$–$C_4$ alkyl; and $R_5$ is hydrogen or methyl group.

6. A compound according to claim 2 wherein:

W, $R_1$, $R_2$ and $R_3$ are as defined above, $R_4$ is a 3,4-dihydrocarbostyril derivative of formula (D'):

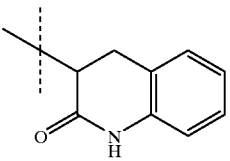

(D')

wherein the nitrogen atom may be substituted by methyl, ethyl, propyl, methoxycarbonyl or ethoxycarbonyl, and the phenyl ring may be substituted by one or two substituents selected from chloro, fluoro, methyl, methoxy or 3,4-methylenedioxy; and $R_5$ is hydrogen or methyl group.

7. A compound according to claim 2 wherein W, $R_1$, $R_2$ and $R_3$ are as defined above, $R_4$ and $R_5$, taken together with the nitrogen atom to which they are attached, constitute an azaheterocyclic ring selected from morpholine, thiomorpholine, pyrrolidine, piperidine, piperazine, pyridazine, thiazolidine, tetrahydroisoquinoline, hexamethyleneimmine and hexahydropyridazine, either unsubstituted or substituted by one or more substituents selected from methyl, ethyl, phenyl, 4-fluorophenyl, benzyl, alpha-methylbenzyl, hydroxy, hydroxymethyl, and carbamoyl, or by a group —CONH—A wherein A is selected from methyl, isopropyl, tert-butyl, cyclopropyl cyclobutyl, cyclopentyl, cyclohexyl, phenyl, 4-fluorophenyl, 4-chlorophenyl, 4-methoxyphenyl, 2-pyridyl, 3-pyridyl, 4-pyridyl, 4-piperidyl, 2-thiazolyl, 1-naphthyl, 2-naphthyl, 3-quinolyl, 5-quinolyl, 3-isoquinolinyl, 5-isoquinolyl, 3-quinuclidinyl, 3,4-(methylenedioxy)phenyl and piperonyl.

8. A compound according to claim 2 wherein:

W is either —NHOH or OH;

$R_2$ is hydroxy;

$R_3$ is —$CH_2$alkyl, —$CH_2$-cycloalkyl, —$(CH_2)_n$—O-alkyl, —$(CH_2)_n$—O-cycloalkyl, —$(CH_2)_n$—O—$(CH_2)_{n'}$-aryl, —$(CH_2)_n$—O—$(CH_2)_{n'}$-heterocyclyl, —$(CH_2)_n$—S-alkyl, —$(CH_2)_n$—S-cycloalkyl, —$(CH_2)_n$—S$(CH_2)_{n'}$-aryl, —$(CH_2)_n$—S—$(CH_2)_{n'}$-heterocyclyl, —$(CH_2)_n$—S(O)-alkyl, —$(CH_2)_n$—S(O)-cycloalkyl, —$(CH_2)_n$—$SO_2$-alkyl, —$(CH_2)_n$—$SO_2$-cycloalkyl, —$(CH_2)_n$—$SO_2$—$(CH_2)_{n'}$-aryl, —$(CH_2)_n$—$SO_2$—$(CH_2)_{n'}$-heterocyclyl, —$(CH_2)_n$—$SO_2$NH-alkyl, —$(CH_2)_n$—$SO_2$NH-cycloalkyl, —$(CH_2)_n$—$SO_2$NH—$(CH_2)_{n'}$-aryl, —$(CH_2)_n$—$SO_2$NH—$(CH_2)_{n'}$-heterocyclyl, —$(CH_2)_n$—CO-alkyl, —$(CH_2)_n$—CO-cycloalkyl, —$(CH_2)_n$—CO—$(CH_2)_{n'}$-aryl, —$(CH_2)_n$—CO—$(CH_2)_{n'}$-heterocyclyl, —$(CH_2)_n$—CONH-alkyl, —$(CH_2)_n$—CONH-cycloalkyl, —$(CH_2)_n$—CONH—$(CH_2)_{n'}$-aryl, —$(CH_2)_{n'}$—CONH—$(CH_2)_{n'}$-heterocyclyl, —$(CH_2)_n$—NHCO-alkyl, —$(CH_2)_n$—NHCO-cycloalkyl, —$(CH_2)_n$—NHCO—$(CH_2)_{n'}$-aryl, —$(CH_2)_n$—NHCO—$(CH_2)_{n'}$-heterocyclyl, —$(CH_{2n}$—$NHCO_2$-alkyl, —$(CH_2)_n$—$NHSO_2$-cycloalkyl, —$(CH_2)_n$—$NHSO_2$—$(CH_2)_{n'}$-aryl, or —$(CH_2)_n$—$NHSO_2$—$(CH_2)_{n'}$-heterocyclyl wherein said alkyl, cycloalkyl, aryl and heterocyclyl groups are unsubstituted or substituted by one to three substituents selected from the group consisting of chloro, fluoro, hydroxy, methoxy, and $C_1$–$C_4$ alkyl; and n and n', being the same or different, are zero or an integer from 1 to 5;

$R_4$ and $R_5$ are;

$R_1$ is a hydroxymethyl derivative which is —$CH_2OCH_3$, —$CH_2$—O—(tetrahydropyranyl), —$CH_2OCOCH_3$, —$CH_2OCOC(CH_3)_3$, —$CH_2OCONH_2$, —$CH_2OCONHCH_3$, —$CH_2OCON(CH_3)_2$, —$CH_2OCONH$-cyclohexyl, —$CH_2OCON(CH_3)$-cyclohexyl, —$CH_2$—O—CO-morpholino, —$CH_2$—O—CO-pyrrolidino, —$CH_2$—O—CO-piperidino; or it is —$CH_2OCH_2Ph$, —$CH_2OCOPh$, —$CH_2OCOCH_2Ph$, —$CH_2OCONHCH_2Ph$ or a derivative thereof wherein the Ph group is substituted by one, two or three substituents selected from chloro, fluoro, hydroxy, $C_1$–$C_4$ alkoxy, methyl and carbamoyl, or by 3,4-dioxymethylene.

9. A compound according to claim 2 wherein: W is either —NHOH or OH:

$R_2$ is hydroxy;

$R_3$ is —$CH_2$-alkyl, —$CH_2$-cycloalkyl, —$(CH_2)_n$—O-alkyl, —$(CH_2)_n$—O-cycloalkyl, —$(CH_2)_n$—O—$(CH_2)_{n'}$-aryl, —$(CH_2)_n$—O—$(CH_2)_{n'}$-heterocyclyl, —$(CH_2)_n$—S-alkyl, —$(CH_2)_n$—S-cycloalkyl, —$(CH_2)_n$—S$(CH_2)_{n'}$-aryl, —$(CH_2)_n$—S—$(CH_2)_{n'}$-heterocyclyl, —$(CH_2)_n$—S(O)-alkyl, —$(CH_2)_n$—S(O)-cycloalkyl, —$(CH_2)_n$—$SO_2$-alkyl, —$(CH_2)_n$—$SO_2$-cycloalkyl, —$(CH_2)_n$—$SO_2$—$(CH_2)_{n'}$-aryl, —$(CH_2)_n$—$SO_2$—$(CH_2)_{n'}$-heterocyclyl, —$(CH_2)_n$—$SO_2$NH-alkyl, —$(CH_2)_n$—$SO_2$NH-cycloalkyl, —$(CH_2)_n$—$SO_2$NH—$(CH_2)_{n'}$-aryl, —$(CH_2)_n$—$SO_2$NH—$(CH_2)_{n'}$-heterocyclyl, —$(CH_2)_n$—CO-alkyl, —$(CH_2)_n$—CO-cycloalkyl, —$(CH_2)_n$—CO—$(CH_2)_{n'}$-aryl, —$(CH_2)_n$—CO—$(CH_2)_{n'}$-heterocyclyl, —$(CH_2)_n$—CONH-alkyl, —$(CH_2)_n$—CONH-cycloalkyl, —$(CH_2)_n$—CONH—$(CH_2)_{n'}$-aryl, —$(CH_2)_{n'}$—CONH—$(CH_2)_{n'}$-heterocyclyl, —$(CH_2)_n$—NHCO-alkyl, —$(CH_2)_n$—NHCO-cycloalkyl, —$(CH_2)_n$—NHCO—$(CH_2)_{n'}$-aryl, —$(CH_2)_n$—NHCO—$(CH_2)_{n'}$-heterocyclyl, —$(CH_2)_n$—$NHSO_2$-alkyl, —$(CH_2)_n$—$NHSO_2$-cycloalkyl, —$(CH_2)_n$—$NHSO_2$—$(CH_2)_{n'}$-aryl or —$(CH_2)_n$—$NHSO_2$—$(CH_2)_{n'}$-heterocyclyl wherein said alkyl, cycloalkyl, aryl and heterocyclyl groups are unsubstituted or substituted by one to three substituents selected from the group consisting of chloro, fluoro, hydroxy, methoxy, and $C_1$–$C_4$ alkyl; and n and n', being the same or different, are zero or an integer from 1 to 5;

$R_4$ is a group of formula (C):

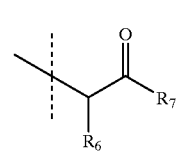

(C)

wherein $R_6$ is phenyl, pyridyl, isopropyl, sec-butyl, tertbutyl, adamantyl, cyclopentyl, cyclohexyl, cyclohexylmethyl, phenylmethyl, -pyridylmethyl, 3-pyridylmethyl, 4-pyridylmethyl, 2-thienylmethyl, 3-indolylmethyl, 3-(N-methyl)indolylmethyl, 1,1-diphenylmethyl, 1-naphthyl, 2-naphthyl, 1-naphthylmethyl, 2-naphthylmethyl, quinolylmethyl or isoquinolymethyl, or a derivative thereof substituted by one to three substituents selected from chloro, fluoro, hydroxy, methoxy, carbamoyl and $C_1$–$C_4$ alkyl; or $R_6$ is —$C(CH_3)_2SCH_3$ or a sulfoxide or sulfone thereof, —$C(CH_3)_2OCH_3$, —$CH_2CH_2CH_2$—$OCH_3$, or —$CH(CH_3)OH$ or the tert-butyl ether thereof; and wherein $R_7$ is —$NH_2$ or a group —NH—A—, NH—$CH_2$—A or $NHCH_2CH_2$—A, wherein A, being as defined above, is selected from methyl, Isopropyl, tert-butyl, phenyl, 4-methoxyphenyl, 4-fluorophenyl, 4-(aminosulfonyl)phenyl, 4-(dimethylaminosulfonylmethyl)phenyl, (3,4-methylenedioxy)phenyl, 2-pyridyl, 3-pyridyl, 4-pyridyl, 4-piperidyl, 2-thiazolyl, 1-naphthyl, 2-naphthyl, 3-quinolyl, 5-quinolyl, 3-isoquinolinyl, 5-isoquinolyl, 3-quinuclidinyl, 2-benzimidazolyl, 5-tetrazolyl, cyclopropyl, cyclobutyl, cyclopentyl, cyclohexyl, 1-morpholino, 1-piperidino, or 1-pyrrolidino;

$R_5$ is hydrogen or a methyl group;

$R_1$ is a mercaptomethyl derivative which is a group —$CH_2SCOCH_3$, —$CH_2S$—$COPh$, —$CH_2S$—$CH_3$, —CH$_2$S—Ph, —CH$_2$S—CH$_2$Ph, —CH$_2$SO$_2$—CH$_3$, —CH$_2$SO$_2$—Ph, —CH$_2$SO$_2$—CH$_2$Ph, —CH$_2$S-thienyl, —CH$_2$S—(1-methyl 1,2,3,4-tetrazol-5-yl), or a derivative thereof wherein the Ph group is substituted by one or two substituents selected from chloro, fluoro, hydroxy, C$_1$–C$_4$ alkoxy, methyl and carbamoyl, or by 3,4-dioxymethylene.

10. A compound according to claim 2 wherein:

W is either —NHOH or OH;

R$_1$ is either hydroxymethyl or mercaptomethyl, or it is the hydroxymethyl derivative, or it is the mercaptomethyl derivative;

R$_2$ is hydroxy;

R$_3$ is isobutyl, cyclopentylmethyl, 3-(4-chlorophenyl)propyl, 3-(4-methoxyphenyl)propyl, 3-(4-biphenyl)propyl, 3-[4-(4fluorophenyl)phenyl]propyl, 3-[4-(4-chlorophenyl)phenyl]propyl, 3-[4-(4-methoxyphenyl)phenyl]propyl, 3-(4-phenoxyphenyl)propyl, 3-(4-pyridoxyphenyl)propyl, (4-methoxybenzene)sulfonylmethyl, and (4-butoxybenzene)sulfonylmethyl; and R$_4$ is a group of formula (C):

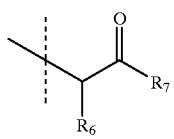

(C)

wherein R$_6$ is phenyl, pyridyl, isopropyl, sec-butyl, tertbutyl, adamantyl, cylalopentyl, cyclohexyl, cyclohexylmethyl, phenylmethyl, -pyridylmethyl, 3-pyridylmethyl, 4-pyridylmethyl, 2-thienylmethyl, 3-indolylmethyl, 3-(Nmethyl)indolylmethyl, 1,1-diphenylmethyl, 1-naphthyl, 2-naphthyl, 1-naphthylmethyl, 2-naphthylmethyl, quinolylmethyl or isoquinolylmethyl, or a derivative thereof substituted by one to three substituents selected from chloro, fluoro, hydroxy, methoxy, carbamoyl and C$_1$–C$_4$ alkyl; or R$_6$ is —C(CH$_3$)$_2$SCH$_3$ or a sulfoxide or sulfone thereof, —C(CH$_3$)$_2$OCH$_3$, —CH$_2$CH$_2$CH$_2$—OCH$_3$, or —CH(CH$_3$)OH or the tert-butyl ether thereof; and wherein R$_7$ is —NH$_2$ or a group —NH—A—, NH—CH$_2$—A or NHCH$_2$CH$_2$—A, wherein A, being as defined above, is selected from methyl, Isopropyl, tert-butyl, phenyl, 4-methoxyphenyl, 4-fluorophenyl, 4-(aminosulfonyl)phenyl, 4-(dimethylaminosulfonylmethyl)phenyl, (3,4-methylenedioxy)phenyl, 2-pyridyl, 3-pyridyl, 4-pyridyl, 4-piperidyl, 2-thiazolyl, 1-naphthyl, 2-naphthyl, 3-quinolyl, 5-quinolyl, 3-isoquinolinyl, 5-isoquinolyl, 3-quinuclidinyl, 2-benzimidazolyl, 5-tetrazolyl, cyclopropyl, cyclobutyl, cyclopentyl, cyclohexyl, 1-morpholino, 1-piperidino, or 1-pyrrolidino;

R$_5$ is hydrogen or a methyl group.

11. A process for producing a compound as defined in claim 1, which process comprises:

(a) coupling an acid of formula (II), or a salt thereof:

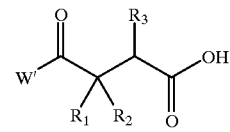

(II)

wherein R$_1$, R$_2$ and R$_3$ are as defined in claim 1 and W' is protected —OH or protected —NHOH, with an amine of formula (III) or a salt thereof:

(III)

wherein R$_4$ and R$_5$ are as defined in claim 1, to obtain a compound of formula (Ia):

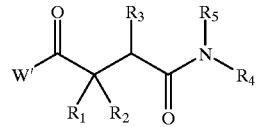

(Ia)

wherein W', R$_1$, R$_2$, R$_3$, R$_4$ and R$_5$ are as defined above, and then removing the protecting group from this compound to yield a compound of formula (I) wherein W is —OH or —NHOH or a salt thereof; or (b) converting a compound of formula (IV)

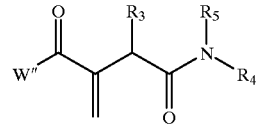

(IV)

wherein W" is OH or W', and R$_3$, R$_4$, R$_5$ and W' are as defined above, into a compound of formula (I) or (Ia) as defined above, and then, when a compound of formula (Ia) is obtained, removing the protecting group from this compound to yield a compound of formula (I) wherein w is —OH or —NHOH, or a salt thereof; or (c) condensing a lactone of formula (V)

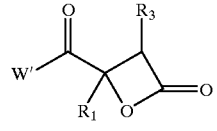

(V)

wherein W', R$_1$ and R$_3$ are as defined above, with an amine of formula (III) as defined above, to obtain a compound of formula (Ia) as defined above wherein R$_2$ is hydroxy, and then removing the protecting group from this compound to yield a compound of formula (I) wherein W is —OH or —NHOH and R$_2$ is hydroxy; or (d) condensing a lactone of formula (VI):

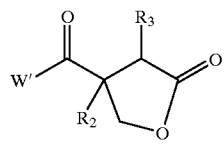
(VI)

wherein W', $R_2$ and $R_3$ are as defined above, with an amine of formula (III) as defined above, to obtain a compound of formula (Ia) above wherein $R_1$ is hydroxymethyl, and then removing the protecting group from this compound to yield a compound of formula (I) wherein W is —OH or —NHOH and $R_1$ is hydroxymethyl, and, if desired, (e) converting one compound of formula (I) or (Ia) into another compound of formula (I) or (Ia) and/or converting a compound of formula (I) into a pharmaceutically acceptable salt thereof, and/or converting a salt of a compound of formula (I) into the free compound.

12. A pharmaceutical composition which comprises, as active ingredient, a compound as defined in claim 1 and a pharmaceutically acceptable carrier, diluent or excipient.

13. A compound as defined in claim 1 for use in a method of treatment or prophylaxis of a disease mediated in a mammal by a matrix metalloproteinase.

14. A compound according to claim 13 for use in a method of treatment or prophylaxis of a tumoral disease in man, in particular for the control of local spread of established tumors, and for the inhibition of the growth of established or occult metastases, either alone or in combination with cytotoxic or cytostatic drugs, or with inhibitors of angiogenesis.

15. A compound according to claim 13 for use in a method of treatment or prophylaxis of rheumatoid arthritis or osteoarthritis in man, alone or in combination with non-steroidal or steroidal antiinflammatory drugs, or with immunosuppressive drugs.

16. A compound as defined in claim 1 for use in a method of treatment or prophylaxis of an inflammatory, infectious or immunological disease promoted by local or systemic release of soluble TNF.

17. An acid of formula (II), or an ester thereof:

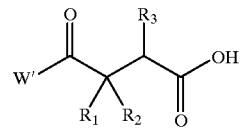
(II)

wherein W' is protected —OH or protected —NHOH, and $R_1$ to $R_3$ are as defined in claim 1.

18. A propiolactone of formula (V):

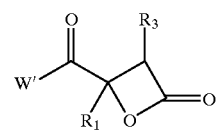
(V)

wherein W' is either free or protected —OH or —NHOH, and $R_1$ and $R_3$ are as defined in claim 1.

19. A butyrolactone of formula (VI):

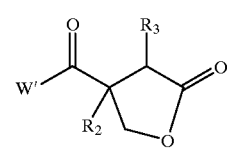
(VI)

wherein W' is either free or protected —OH or —NHOH, and $R_2$ and $R_3$ are as defined in claim 1.

* * * * *

UNITED STATES PATENT AND TRADEMARK OFFICE
CERTIFICATE OF CORRECTION

PATENT NO. : 6,194,451B1  Page 1 of 1
DATED : Feb 27, 2001
INVENTOR(S) : Marco Alpegiani, et al.

It is certified that error appears in the above-identified patent and that said Letters Patent is hereby corrected as shown below:

-- (86) PCT No.: PCT/EP98/00531

§ 371 Date: Jul. 30, 1999

§ 102(e) Date: Jul. 30, 1999 --

Signed and Sealed this

Twenty-first Day of August, 2001

*Attest:*

*Nicholas P. Godici*

*Attesting Officer*

NICHOLAS P. GODICI
*Acting Director of the United States Patent and Trademark Office*